(12) United States Patent
Luk et al.

(10) Patent No.: US 7,576,082 B2
(45) Date of Patent: Aug. 18, 2009

(54) OXINDOLE DERIVATIVES

(75) Inventors: Kin-Chun Luk, North Caldwell, NJ (US); Sung-Sau So, Nutley, NJ (US); Jing Zhang, Parsippany, NJ (US); Zhuming Zhang, Hillsborough, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 382 days.

(21) Appl. No.: 11/471,363

(22) Filed: Jun. 20, 2006

(65) Prior Publication Data

US 2006/0293319 A1 Dec. 28, 2006

Related U.S. Application Data

(60) Provisional application No. 60/795,616, filed on Apr. 27, 2006, provisional application No. 60/693,752, filed on Jun. 24, 2005.

(51) Int. Cl.
| | |
|---|---|
| *A61K 31/535* | (2006.01) |
| *A61K 31/445* | (2006.01) |
| *A61K 31/415* | (2006.01) |
| *A61K 31/40* | (2006.01) |
| *C07D 413/00* | (2006.01) |
| *C07D 401/00* | (2006.01) |
| *C07D 403/02* | (2006.01) |
| *C07D 487/00* | (2006.01) |
| *C07D 209/04* | (2006.01) |

(52) U.S. Cl. ............. 514/235.2; 514/323; 514/406; 514/418; 544/144; 546/201; 546/256; 548/364.7; 548/466; 548/469; 548/492

(58) Field of Classification Search .......... 546/184, 546/192, 195, 196, 200, 201, 256; 548/400, 548/416, 452, 465, 469, 484, 492, 517, 364.7, 548/466; 544/144; 514/235.21, 323, 406, 514/418

See application file for complete search history.

(56) References Cited

U.S. PATENT DOCUMENTS

| 2,759,935 A | 8/1956 | Speeter et al. |
|---|---|---|
| 3,441,570 A | 4/1969 | Meyer |
| 3,686,210 A | 8/1972 | Bell et al. |
| 4,020,179 A | 4/1977 | Irvine |
| 6,511,974 B1 | 1/2003 | Dusza et al. |

FOREIGN PATENT DOCUMENTS

| JP | 55 129284 | 6/1980 |
|---|---|---|
| JP | 2000 191661 | 7/2000 |
| WO | WO 98/02432 | 1/1998 |
| WO | WO 98/54167 A1 | 12/1998 |
| WO | WO 00/71129 A1 | 11/2000 |
| WO | WO 03/008407 | 1/2003 |
| WO | WO 03/078394 A1 | 9/2003 |
| WO | WO 2006/080574 A1 | 8/2006 |

OTHER PUBLICATIONS

Christopher Hulme, et al., Bioorganic & Medicinal Chemistry Letters, vol. 8, pp. 175-178 (1998), XP002405133.
F.D. Dopp, et al., J. Heterocyclic Chem., vol. 17, No. 9, pp. 1329-1330 (1980), XP002405134.
Gordon N. Walker, et al., J. Med. Chem., vol. 8, pp. 626-637 (1965), XP002405135.
Stanislav Kafka, et al., J. Org. Chem., vol. 66, pp. 6394-6399 (2001), XP002405136.
Amarnath Natarajan, et al., J. Med. Chem., vol. 47, pp. 1882-1885 (2004), XP002405137.
James C. Powers, J. Org. Chem., vol. 30, pp. 2534-2540 (1965), XP002405138.
Sengodagounder Muthusamy, et al., Synlett, vol. 2002, No. 11, pp. 1783-1786 (2002), XP002405139.
Ward C. Sumpter, J. Am. Chem Soc., vol. 54, pp. 2917-2918 (1932), XP002405141.
H.E. Zaugg, et al., J. Am. Chem. Soc., vol. 84, pp. 4574-4578 (1962), XP002418406.
Steven P. Govek, et al., J. Am. Chem. Soc., vol. 123, pp. 9468-9469 (2001), XP002418407.
Rita Kapiller-Dezofi, et al., New J. Chem., vol. 28, pp. 1214-1220 (2004), XP002418408.
David W. Robertson, et al., J. Med. Chem., vol. 29, pp. 1832-1840 (1986), XP002418409.
Kazuo Takayama, et al., Tetrahedron Letters, vol. 5, pp. 365-368 (1973), XP002418410.
Audris Huang, et al., J. Am. Chem. Soc., vol. 126, pp. 14043-14053 (2004), XP002418411.
Masaru Ogata, et al., Eur. J. Med. Chem.—Chimica Therapeutica, vol. 16, No. 4, pp. 373-379 (1981), XP00907847.
Istvan Moldvai, et al., Arch. Pharm. Pharm. Med. Chem., vol. 329, pp. 541-549 (1996), XP009078456.
Hossein Pajouheish, et al., J. Pharm. Sci., vol. 72, No. 3, pp. 318-321 (1983), XP009078411.
Krishna C. Joshi, et al., Journal of Fluorine Chemistry, vol. 44, pp. 59-72 (1989), XP002418412.

(Continued)

*Primary Examiner*—Kamal A Saeed
*Assistant Examiner*—Samantha L Shterengarts
(74) *Attorney, Agent, or Firm*—George W. Johnston; Patricia S. Rocha-Tramaloni

(57) ABSTRACT

The invention describes compounds of the general formula I

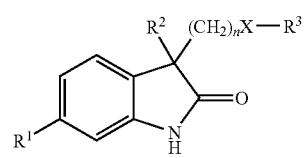

or the pharmaceutically acceptable salts thereof,
wherein $R^1$, $R^2$, $R^3$ and X are herein described,
a process for their manufacture, medicaments containing them as well as the use of these compounds as pharmaceutically active agents. The compounds show activity as antiproliferative agents and may be especially useful for the treatment of cancer.

12 Claims, No Drawings

OTHER PUBLICATIONS

Piyasena Hewawasam, et al., Bioorganic & Medicinal Chemistry Letters, vol. 12, pp. 1023-1026 (2002), XP002418413.

Santiago Barroso, et al., J. Org., Chem., vol. 69, pp. 6821-6829 (2004), XP002418416.

Paul Aeberli, et al., J. Org. Chem., vol. 33, No. 4 pp. 1640-1643 (1968), XP002418417.

A. Walser, et al., J. Org. Chem., vol. 38, No. 3, pp. 449-456 (1973), XP002418418.

Javad Azizian, et al., Synthesis, vol. 2005, No. 7, pp. 1095-1098 (2005), XP 002418427.

Andrew Fensome, et al., Bioorganic & Medicinal Chemistry Letters, vol. 12, pp. 3487-3490 (2002), XP002418428.

T.V. Rajanbabu, et al., J. Org. Chem., vol. 51, pp. 1704-1712 (1986), XP002418429.

Karnail S. Atwal, et al., J. Med. Chem., vol. 39, pp. 304-313 (1996), XP002418430.

Balazs Volk, et al., Eur. J. Org. Chem., pp. 3991-3996 (2003), XP002418431.

Keith Smith, et al., J. Chem. Soc. Perkin Trans. 1, vol. 1999, pp. 2299-2303 (1999), XP002418432.

R.L. Hinman, et al., J. Org. Chem., vol. 29, pp. 2431-2437 (1964), XP002418433.

Ansel et al., Pharmaceutical Dosage Forms and Drug Delivery Systems (6th Ed. 1995) at pp. 196.

Ansel et al., Pharmaceutical Dosage Forms and Drug Delivery Systems (6th Ed. 1995) at p. 1456-1457.

Kraynack, E. A.; Dalgard, J. E.; Gaeta, F. C. A. *Tetrahedron Letters*, 1998, 39, 7679-7682.

P.; Erway, et al., *J. Med. Chem*. 2002, 45, 1487-1499.

Elliott, I. W.; Rivers, P. *J. Org. Chem*. 1964, 29, 2438-2440.

Andreani, A.; et al., *Eur. J. Med. Chem*. 1990, 25, 187-190.

US 7,576,082 B2

OXINDOLE DERIVATIVES

This application claims the benefit of U.S. Provisional Application No. 60/693,752, filed Jun. 24, 2005 and U.S. Provisional Application No. 60/795,616, filed Apr. 27, 2006. The entire contents of the above-identified applications are hereby incorporated by reference.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

SUMMARY OF THE INVENTION

The present invention provides oxindole derivatives which are small molecule inhibitors of the MDM2-p53 interaction. In cell-free and cell-based assays, compounds of the present invention are shown to inhibit the interaction of MDM2 protein with a p53-like peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

The present invention provides at least one compound of formula I

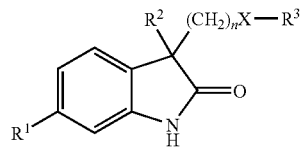

or the pharmaceutically acceptable salts thereof wherein $R^1$, $R^2$, $R^3$, X and n are as herein defined.

DETAILED DESCRIPTION OF THE INVENTION

There are provided oxindole derivatives of the formula

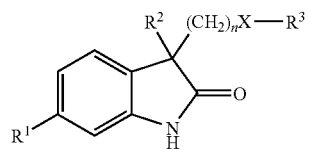

or the pharmaceutically acceptable salts thereof
wherein
X is a bond, O or N;
$R^1$ is selected from the group consisting of hydrogen, halogen, cyano, lower alkyl, lower alkenyl, lower alkynyl, lower alkoxy, $NO_2$, methyl sulfonyl and sulfonamide;
$R^2$ and $R^3$ are selected from the group consisting of aryl, substituted aryl, heteroaryl, substituted heteroaryl, cycloalkyl, substituted cycloalkyl, heterocycle, substituted heterocycle, heterocycloalkenyl and lower alkyl; and
n is 1-3.

Preferred are compounds wherein $R^1$ is halogen, $R^2$ is substituted aryl, substituted heteroaryl, substituted cycloalkyl or substituted heterocycle, $R^3$ is substituted aryl, substituted heteroaryl, substituted cycloalkyl or substituted heterocycle, n is 1 and X is a bond.

Also preferred are compounds wherein $R^1$ is halogen, $R^2$ is substituted aryl, substituted heteroaryl, substituted cycloalkyl or substituted heterocycle, $R^3$ is a meta halogen substituted phenyl, n is 1 and X is a bond.

Especially preferred are compounds of the formula:
rac-6-Chloro-3-(3-chloro-benzyl)-3-(1-methyl-1H-pyrazol-4-yl)-1,3-dihydro-indol-2-one;
rac-3-(1-Acetyl-piperidin-4-yl)-6-chloro-3-(3-chloro-benzyl)-1,3-dihydro-indol-2-one;
rac-4-[6-Chloro-3-(3-chloro-benzyl)-2-oxo-2,3-dihydro-1H-indol-3-yl]-piperidine-1-carboxylic acid methylamide;
rac-3-(3-Bromo-benzyl)-6-chloro-3-(3-methoxy-phenyl)-1,3-dihydro-indol-2-one;
rac-6-Chloro-3-(3-fluoro-benzyl)-3-(3-methoxy-phenyl)-1,3-dihydro-indol-2-one;
rac-6-Chloro-3-(3-chloro-benzyl)-3-cyclohexyl-1,3-dihydro-indol-2-one;
rac-5-[6-Chloro-3-(3-chloro-benzyl)-2-oxo-2,3-dihydro-1H-indol-3-yl]-3,4-dihydro-2H-pyridine-1-carboxylic acid tert-butyl ester;
rac-6-Chloro-3-(2,6-dichloro-pyridin-4-ylmethyl)-3-(3-methoxy-phenyl)-1,3-dihydro-indol-2-one;

3-[6-Chloro-3-(3-chloro-benzyl)-2-oxo-2,3-dihydro-1H-indol-3-yl]-piperidine-1-carboxylic acid tert-butyl ester;
rac-5-[6-Chloro-3-(2,6-dichloro-pyridin-4-ylmethyl)-2-oxo-2,3-dihydro-1H-indol-3-yl]-3,4-dihydro-2H-pyridine-1-carboxylic acid tert-butyl ester;
3-(1-Acetyl-piperidin-3-yl)-6-chloro-3-(3-chloro-benzyl)-1,3-dihydro-indol-2-one;
6-Chloro-3-(3-chloro-benzyl)-3-[1-(pyrrolidine-1-carbonyl)-piperidin-3-yl]-1,3-dihydro-indol-2-one;
3-[6-Chloro-3-(3-chloro-benzyl)-2-oxo-2,3-dihydro-1H-indol-3-yl]-piperidine-1-carboxylic acid methylamide;
6-Chloro-3-(3-chloro-benzyl)-3-[1-(morpholine-4-carbonyl)-piperidin-3-yl]-1,3-dihydro-indol-2-one;
rac-6-Chloro-3-(3-chloro-benzyl)-3-(2,6-dimethoxy-pyrimidin-4-yl)-1,3-dihydro-indol-2-one, rac-6-Chloro-3-(3-chloro-benzyl)-3-(3-oxo-cyclohexyl)-1,3-dihydro-indol-2-one,
3-[6-Chloro-3-(3-chloro-benzyl)-2-oxo-2,3-dihydro-1H-indol-3-yl]-piperidine-1-carboxylic acid ethylamide,
3-[6-Chloro-3-(3-chloro-benzyl)-2-oxo-2,3-dihydro-1H-indol-3-yl]-piperidine-1-carboxylic acid propylamide,
3-[6-Chloro-3-(3-chloro-benzyl)-2-oxo-2,3-dihydro-1H-indol-3-yl]-piperidine-1-carboxylic acid tert-butylamide,
3-[6-Chloro-3-(3-chloro-benzyl)-2-oxo-2,3-dihydro-1H-indol-3-yl]-piperidine-1-carboxylic acid (2-chloro-ethyl)-amide,
3-[6-Chloro-3-(3-chloro-benzyl)-2-oxo-2,3-dihydro-1H-indol-3-yl]-piperidine-1-carboxylic acid phenylamide,
3-[6-Chloro-3-(3-chloro-benzyl)-2-oxo-2,3-dihydro-1H-indol-3-yl]-piperidine-1-carboxylic acid isopropylamide,
rac-6-Chloro-3-(3-chloro-4-fluoro-benzyl)-3-(3-methoxy-phenyl)-1,3-dihydro-indol-2-one,
3-[6-Chloro-3-(3-chloro-benzyl)-2-oxo-2,3-dihydro-1H-indol-3-yl]-piperidine-1-carboxylic acid cyclohexylamide,
rac-6-Chloro-3-(3-chloro-benzyl)-3-pyridin-3-yl-1,3-dihydro-indol-2-one,
rac-6-Chloro-3-(3-chloro-benzyl)-3-(3,5-dimethoxy-phenyl)-1,3-dihydro-indol-2-one,
rac-3-[6-Chloro-3-(3-chloro-benzyl)-2-oxo-2,3-dihydro-1H-indol-3-yl]-piperidine-1-carboxylic acid (3-methoxy-phenyl)-amide,
rac-3-[6-Chloro-3-(3-chloro-benzyl)-2-oxo-2,3-dihydro-1H-indol-3-yl]-piperidine-1-carboxylic acid (4-methoxy-phenyl)-amide,
rac-3-[6-Chloro-3-(3-chloro-benzyl)-2-oxo-2,3-dihydro-1H-indol-3-yl]-piperidine-1-carboxylic acid (2-methoxy-phenyl)-amide,
rac-3-[6-Chloro-3-(3-chloro-benzyl)-2-oxo-2,3-dihydro-1H-indol-3-yl]-piperidine-1-carboxylic acid (4-chloro-phenyl)-amide,
rac-3-[6-Chloro-3-(3-chloro-benzyl)-2-oxo-2,3-dihydro-1H-indol-3-yl]-piperidine-1-carboxylic acid (3-chloro-phenyl)-amide,
rac-3-[6-Chloro-3-(3-chloro-benzyl)-2-oxo-2,3-dihydro-1H-indol-3-yl]-piperidine-1-carboxylic acid pyridine-3-yl-amide,
rac-6-Chloro-3-(3-chloro-benzyl)-3-naphthalen-2-yl-1,3-dihydro-indol-2-one,
rac-6-Chloro-3-(3-chloro-benzyl)-3-{1-[4-(2-Morpholin-4-yl-2-oxo-ethyl)-piperazine-1-carbonyl]-piperidine-3-yl}-1,3-dihydro-indol-2-one,
rac-3-(1-Butyl-piperidin-4-yl)-6-Chloro-3-(3-chloro-benzyl)-1,3-dihydro-indol-2-one,
rac-6-Chloro-3-(3-chloro-benzyl)-3-{1-[4-(2-Morpholin-4-yl-2-oxo-ethyl)-piperazine-1-carbonyl]-piperidine-4-yl}-1,3-dihydro-indol-2-one,
rac-3-[6-Chloro-3-(3-chloro-benzyl)-2-oxo-2,3-dihydro-1H-indol-3-yl]-piperidine-1-carboxylic acid (3,4,5-trimethoxy-phenyl)-amide,
rac-6-Chloro-3-(3-chloro-benzyl)-3-(3,4-dimethyl-phenyl)-1,3-dihydro-indol-2-one,
rac-6-Chloro-3-(3-chloro-benzyl)-3-(4-isopropyl-phenyl)-1,3-dihydro-indol-2-one,
rac-3-[6-Chloro-3-(3-chloro-benzyl)-2-oxo-2,3-dihydro-1H-indol-3-yl]-piperidine-1-carboxylic acid (4-diomethylamino-phenyl)-amide,
rac-4-({3-[6-Chloro-3-(3-chloro-benzyl)-2-oxo-2,3-dihydro-1H-indol-3-yl]-piperidine-1-carbonyl}-amino)-benzoic acid ethyl ester,
rac-3-[6-Chloro-3-(3-chloro-benzyl)-2-oxo-2,3-dihydro-1H-indol-3-yl]-piperidine-1-carboxylic acid (4-butoxy-phenyl)-amide,
rac-3-[6-Chloro-3-(3-chloro-benzyl)-2-oxo-2,3-dihydro-1H-indol-3-yl]-piperidine-1-carboxylic acid (4-trifluoromethoxy-phenyl)-amide,
rac-3-[6-Chloro-3-(3-chloro-benzyl)-2-oxo-2,3-dihydro-1H-indol-3-yl]-piperidine-1-carboxylic acid pyridine-4-ylamide,
rac-3-[6-Chloro-3-(3-chloro-benzyl)-2-oxo-2,3-dihydro-1H-indol-3-yl]-piperidine-1-carboxylic acid (2,6-dichloro-pyridin-4-yl)-amide,
rac-6-chloro-3-(3-chloro-benzyl)-3-(4-dimethylamino-phenyl)-1,3-dihydro-indol-2-one,
rac-4-[6-Chloro-3-(3-chloro-benzyl)-2-oxo-2,3-dihydro-1H-indol-3-yl]-azepane-1-carboxylic acid tert-butyl ester,
rac-3-[6-Chloro-3-(3-chloro-benzyl)-2-oxo-2,3-dihydro-1H-indol-3-yl]-piperidine-1-carboxylic acid (6-methoxy-pyridin-3-yl)-amide,
rac-4-({3-[6-Chloro-3-(3-chloro-benzyl)-2-oxo-2,3-dihydro-1H-indol-3-yl]-piperidine-1-carbonyl}-amino)-benzoic acid methyl ester,
rac-4-({3-[6-Chloro-3-(3-chloro-benzyl)-2-oxo-2,3-dihydro-1H-indol-3-yl]-piperidine-1-carbonyl}-amino)-benzoic acid,
rac-3-Azepan-1-yl-6-chloro-3-(3-chloro-benzyl)-1,3-dihydro-indol-2-one,
rac-3-(1-Benzyl-piperidin-3-yl)-6-chloro-3-(3-chloro-benzyl)-1,3-dihydro-indol-2-one,
rac-3-[6-Chloro-3-(3-chloro-benzyl)-2-oxo-2,3-dihydro-1H-indol-3-yl]-piperidine-1-carboxylic acid (6-chloro-pyridin-3-yl)-amide,
rac-3-[6-Chloro-3-(3-chloro-benzyl)-2-oxo-2,3-dihydro-1H-indol-3-yl]-piperidine-1-carboxylic acid (4-carbamoyl-phenyl)-amide,
3-[6-Chloro-3-(3-chloro-benzyl)-2-oxo-2,3-dihydro-1H-indol-3-yl]-piperidine-1-carboxylic acid phenylamide,
rac-3-({3-[6-Chloro-3-(3-chloro-benzyl)-2-oxo-2,3-dihydro-1H-indol-3-yl]-piperidine-1-carbonyl}-amino)-benzoic acid methyl ester,
rac-3-({3-[6-Chloro-3-(3-chloro-benzyl)-2-oxo-2,3-dihydro-1H-indol-3-yl]-piperidine-1-carbonyl}-amino)-benzoic acid,
rac-3-[6-Chloro-3-(3-chloro-benzyl)-2-oxo-2,3-dihydro-1H-indol-3-yl]-piperidine-1-carboxylic acid (4-fluoro-phenyl)-amide,
rac-3-[6-Chloro-3-(3-chloro-benzyl)-2-oxo-2,3-dihydro-1H-indol-3-yl]-piperidine-1-carboxylic acid (6-methyl-pyridine-3-yl)-amide,
rac-6-Chloro-3-(3-chloro-benzyl)-3-{1-(pyridine-4-carbonyl)-piperidin-4-yl}-1,3-dihydro-indol-2-one,
rac-6-Chloro-3-(3-chloro-benzyl)-3-{1-(pyridazine-4-carbonyl)-piperidin-4-yl}-1,3-dihydro-indol-2-one, rac-3-[6-Chloro-3-(3-chloro-benzyl)-2-oxo-2,3-dihydro-1H-indol-3-yl]-piperidine-1-carboxylic acid pyridazin-4-ylamide,
3-[6-Chloro-3-(3-chloro-benzyl)-2-oxo-2,3-dihydro-1H-indol-3-yl]-piperidine-1-carboxylic acid tert-butyl ester,
rac-3-[6-Chloro-3-(3-chloro-benzyl)-2-oxo-2,3-dihydro-1H-indol-3-yl]-piperidine-1-carboxylic acid (4-cyano-phenyl)-amide,
rac-3-[6-Chloro-3-(3-chloro-benzyl)-2-oxo-2,3-dihydro-1H-indol-3-yl]-piperidine-1-carboxylic acid (4-nitro-phenyl)-amide,
rac-3-[6-Chloro-3-(3-chloro-benzyl)-2-oxo-2,3-dihydro-1H-indol-3-yl]-piperidine-1-carboxylic acid (4-amino-phenyl)-amide,
rac-3-[6-Chloro-3-(3-chloro-benzyl)-2-oxo-2,3-dihydro-1H-indol-3-yl]-piperidine-1-carboxylic acid (4-acetylamino-phenyl)-amide,
rac-3-[6-Chloro-3-(3-chloro-benzyl)-2-oxo-2,3-dihydro-1H-indol-3-yl]-piperidine-1-carboxylic acid (4-hydroxy-phenyl)-amide,
rac-3-[6-Chloro-3-(3-chloro-benzyl)-2-oxo-2,3-dihydro-1H-indol-3-yl]-piperidine-1-carboxylic acid (4-acetyl-phenyl)-amide,
rac-3-[6-Chloro-3-(3-chloro-benzyl)-2-oxo-2,3-dihydro-1H-indol-3-yl]-piperidine-1-carboxylic acid (4-methylsulfanyl-phenyl)-amide,
rac-3-[6-Chloro-3-(3-chloro-benzyl)-2-oxo-2,3-dihydro-1H-indol-3-yl]-piperidine-1-carboxylic acid (4-methanesulfinyl-phenyl)-amide,
rac-3-[6-Chloro-3-(3-chloro-benzyl)-2-oxo-2,3-dihydro-1H-indol-3-yl]-piperidine-1-carboxylic acid (4-methanesulfonyl-phenyl)-amide,
rac-5-({3-[6-Chloro-3-(3-chloro-benzyl)-2-oxo-2,3-dihydro-1H-indol-3-yl]-piperidine-1-carbonyl}-amino)-pyridine-2-carboxylic acid methyl ester,
rac-5-({3-[6-Chloro-3-(3-chloro-benzyl)-2-oxo-2,3-dihydro-1H-indol-3-yl]-piperidine-1-carbonyl}-amino)-pyridine-2-carboxylic acid,
rac-3-[6-Chloro-3-(3-chloro-benzyl)-2-oxo-2,3-dihydro-1H-indol-3-yl]-piperidine-1-carboxylic acid [4-(2,5-dioxo-2,5-dihydro-pyrrol-1-yl)-phenyl)-amide,
4-({3-[6-Chloro-3-(3-chloro-benzyl)-2-oxo-2,3-dihydro-1H-indol-3-yl]-piperidine-1-carbonyl}-amino)-benzoic acid,
rac-5-{3-[6-Chloro-3-(3-chloro-benzyl)-2-oxo-2,3-dihydro-1H-indol-3-yl]-piperidine-1-carbonyl}-pyridine-2-carboxylic acid methyl ester,
3-[6-Chloro-3-(3-chloro-benzyl)-2-oxo-2,3-dihydro-1H-indol-3-yl]-piperidine-1-carboxylic acid (4-acetyl-phenyl)-amide,
3-[6-Chloro-3-(3-chloro-benzyl)-2-oxo-2,3-dihydro-1H-indol-3-yl]-piperidine-1-carboxylic acid (4-methanesulfonyl-phenyl)-amide,
rac-6-chloro-3-(3-chloro-benzyl)-3-(3-oxo-cycloheptyl)-1,3-dihydro-indol-2-one,
rac-6-chloro-3-(3-chloro-benzyl)-3-cyclopentylmethyl-1,3-dihydro-indol-2-one,
rac-6-chloro-3-(3-chloro-benzyl)-3-(3,3-dimethyl-butyl)-1,3-dihydro-indol-2-one and
rac-3-benzyl-6-chloro-3-(3-chloro-benzyl)-1,3-dihydro-indol-2-one.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I as well as their salts have at least one asymmetric carbon atom and therefore may be present as racemic mixtures or different stereoisomers. The various isomers can be isolated by known separation methods, e.g., chromatography.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

"Effective amount" means an amount that is effective to prevent, alleviate or ameliorate symptoms of disease or prolong the survival of the subject being treated.

"IC$_{50}$" refers to the concentration of a particular compound required to inhibit 50% of a specific measured activity. IC$_{50}$ can be measured, inter alia, as is described subsequently.

"Pharmaceutically acceptable ester" refers to a conventionally esterified compound of formula I having a carboxyl group or hydroxy group, which esters retain the biological effectiveness and properties of the compounds of formula I and are cleaved in vivo (in the organism) to the corresponding active carboxylic acid or alcohol respectively.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, lower-alkyl-aminocarbonyl, heterocyclocarbonyl, alkylamino-carbonyl, substituted alkylamino-carbonyl, arylamino-carbonyl, cycloalkylamino-carbonyl, substituted heterocyclocarbonyl, substituted arylamino-carbonyl, heteroarylamino-carbonyl, substituted heteroarylamino-carbonyl, benzyl, substituted benzyl, alkylthio, alkylsulfoxide, alkylsulfone, oxo, aminocarbonyl, carboxy, $NO_2$, lower-alkoxy, thio-lower-alkoxy, lower-alkylsufonyl, aminosulfonyl, lower-alkylcarbonyl, lower-alkylcarbonyloxy, lower-alkoxycarbonyl, lower-alkylcarbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$.

For aryl and heteroaryl the preferred substituents are halogen, lower-alkoxy, lower alkyl and amino.

"Alkyl" denotes a straight-chained, branched or cyclic saturated aliphatic hydrocarbon. Preferably, alkyl denotes a lower alkyl group i.e., a C1-C6 alkyl group and includes methyl, ethyl, propyl, isopropyl, butyl, t-butyl, 2-butyl, pentyl, hexyl, and the like. Generally, lower alkyl is preferably C1-C4 alkyl, and more preferably C1-C3 alkyl. Examples of cycloalkyl groups are moieties having 3 to 10, preferably 3 to 7 carbon atoms including cyclopropyl, cyclopentyl and cyclohexyl groups.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

As used herein, the terms "heterocycloalkyl" or "heterocycloalkenyl", are intended to refer to any stable monocyclic or polycyclic ring system, which consists of carbon atoms and at least one heteroatom, particular at least one heteroatom independently selected from the group consisting of N, O and S, any ring of which is fully saturated or partially unsaturated, respectively. Heterocycloalkyl and heterocycloalkenyl groups may be linked via a ring atom being a carbon atom ("C-linked heterocycloalkyl" and "C-linked heterocycloalkenyl", respectively), or via a ring atom being a nitrogen atom ("N-linked heterocycloalkyl" and "N-linked heterocycloalkenyl", respectively). Heteroatoms such as nitrogen and sulfur may optionally be oxidized to form N-oxides or sulfoxides and sulfones, respectively. In certain embodiments, a nitrogen in the heterocycle may be quaternized. In certain embodiments, when the total number of S and O atoms in the heterocycle exceeds 1, then these heteroatoms need not be adjacent to one another. In particular embodiments, the total number of S atoms in the heterocycle is not more than 1.

Examples of heterocycloalkyls and heterocycloalkenyls (including substituted variants thereof) include, but are not limited to, 2-pyrrolidonyl, 2H,6H dithiazinyl, 4-piperidonyl, decahydroquinolinyl, dihydrofuro[2,3-b]tetrahydrofuran, imidazolidinyl, imidazolinyl, indolenyl, indolinyl, morpholinyl, octahydroisoquinolinyl, piperazinyl, piperidinyl, piperidonyl, 4-piperidonyl, pyrrolidinyl, pyrrolinyl, tetrahydrofuranyl, tetrahydroisoquinolinyl, or tetrahydroquinolinyl.

The term "alkylsulfonyl" as used herein means an alkyl-S(O)$_2$— group wherein the alkyl is defined as above.

The term "halogen" as used in the definitions means fluorine, chlorine or bromine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Hetero atom" means an atom selected from N, O and S.

"Heteroaryl" means an aromatic heterocyclic ring system containing up to two rings. Preferred heteroaryl groups include, but are not limited to, thienyl, furyl, indolyl, pyrrolyl, pyridinyl, pyridine, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, aromatic or non-aromatic hydrocarbon, wherein 1 to 3 carbon atoms are replaced by a hetero atom selected from nitrogen, oxygen or sulfur atom. Examples include pyrrolidin-2-yl; pyrollidin-3-yl; imidazol-4-yl; pyrazol-3-yl; morpholin-4-yl and the like.

"Alkoxy or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

Synthesis

Compounds of this invention can be synthesized according to the following schemes.

The 6-substituted oxindole and isatin starting materials were either commercially available or prepared from the corresponding 4-substituted 2-nitro-fluoro or chlorobenzene according to Kraynack, E. A.; Dalgard, J. E.; Gaeta, F. C. A. *Tetrahedron Letters*, 1998, 39, 7679-7682.

3-Mono-substituted 1,3-dihydro-indol-2-one can be synthesized by multiple methods. These include, among others, the methods of Hewawasam, P.; Erway, M.; Moon, S. L.; Knipe, J.; Weiner, H.; Boissard, C. G.; Post-Munson, D. J.; Gao, Q.; Huang, S.; Gribkoff, V. K.; Meanwell, N. A. *J. Med. Chem.* 2002, 45, 1487-1499 (Scheme 1) or Elliott, I. W.; Rivers, P. *J. Org. Chem.* 1964, 29, 2438-2440 and Andreani, A.; Rambaldi, M.; Locatelli, A.; Bossa, R.; Galatulas, I.; Ninci, M. *Eur. J. Med. Chem.* 1990, 25, 187-190 (Scheme 2).

Conversion of the corresponding mono-substituted 1,3-dihydro-indol-2-one to compounds of this invention can be achieved via reaction with the appropriate alkylating agents. One such alkylation is exemplified by the procedure of Dimalta, A.; Garcia, G.; Roux, R.; Schoentjes, B.; Serradeil-Le Gal, C.; Tonnerre, B.; Wagnon, J. WO 03/008407 A2, published Jan. 30, 2003. These alkylated products can be further modified by known procedures to form additional compounds of this invention.

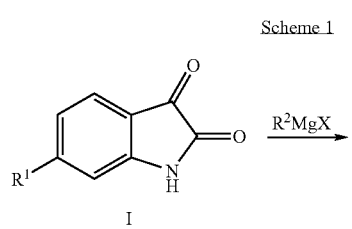

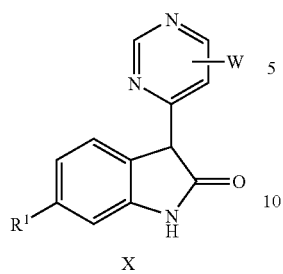

X where Y is an appropriate leaving group and W is a substituent value as defined above.

Scheme 6

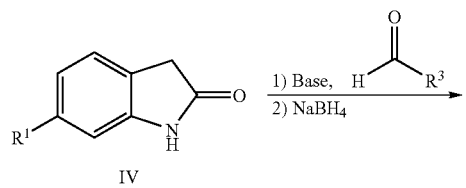

IV

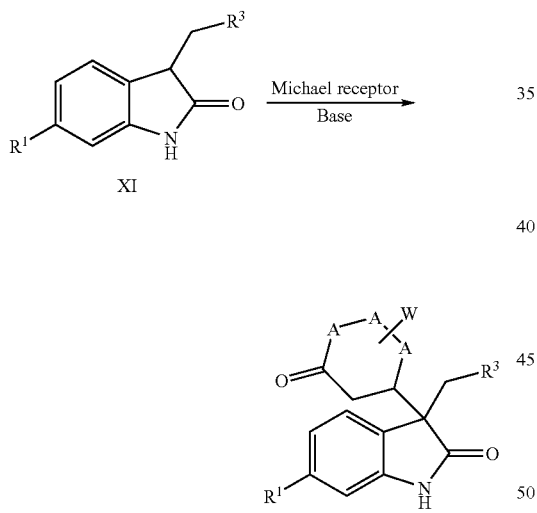

XI

Scheme 7

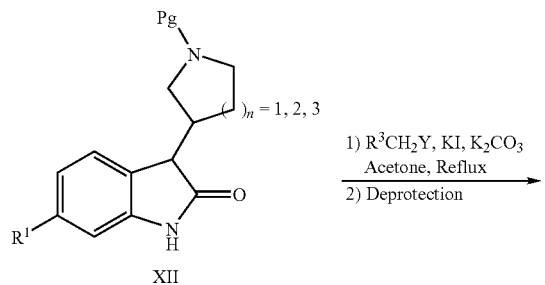

XII

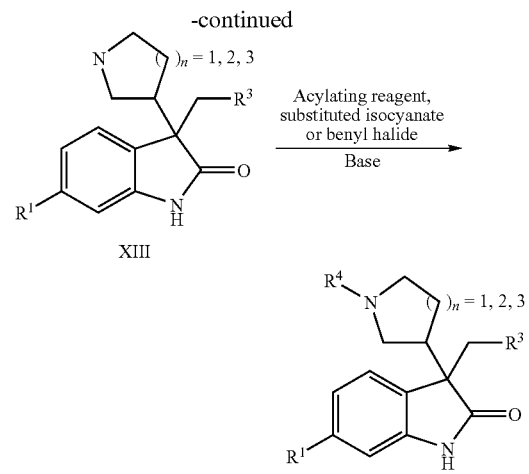

XIII wherein Pg is a protecting group such as Boc, acetyl, etc.

The following examples are provided to aid the understanding of the present invention, the true scope of which is set forth in the appended claims.

EXAMPLE 1a rac-5-Chloro-3-hydroxy-3-(4-methoxy-phenyl)-1,3-dihydro-indol-2-one

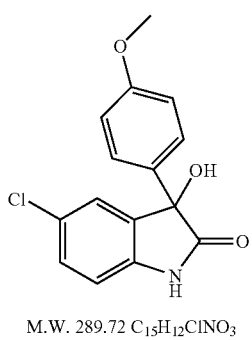

M.W. 289.72 $C_{15}H_{12}ClNO_3$

A solution of 4-methoxyphenyl magnesium bromide in tetrahydrofuran (0.5 M, 50 mL, 25 mmol) (Aldrich) was added dropwise to a suspension of 5-chloroisatin (1.82 g, 10 mmol) (Avocado) in tetrahydrofuran (20 mL) under argon with cooling in a −25° C. bath and magnetic stirring at such a rate that reaction temperature was kept below −10° C. (approximately 30 minutes). Cooling bath was then removed and mixture allowed to warm to room temperature. After stirring for an additional 1 hour, 15% aqueous ammonium chloride solution (50 mL) was added and mixture extracted with ethyl acetate (2×75 mL). Ethyl acetate layers were then washed with water (75 mL), brine (75 mL), combined, dried (MgSO$_4$), filtered and concentrated. Residue was stirred in dichloromethane (100 mL) at room temperature for 30 minutes and filtered to give crude rac-5-chloro-3-hydroxy-3-(4-methoxy-phenyl)-1,3-dihydro-indol-2-one as a white powder. (Yield 2.57 g, 88.7%).

HRMS(ES$^-$) m/z Calcd for $C_{15}H_{12}ClNO_3$—H [(M−H)$^-$]: 288.0433. Found: 288.0432.

EXAMPLE 1b rac-5-Chloro-3-(4-methoxy-phenyl)-1,3-dihydro-indol-2-one

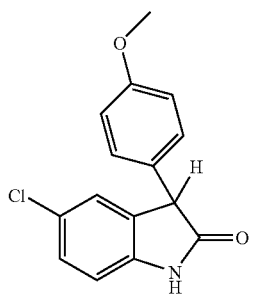

M.W. 273.72 $C_{15}H_{12}ClNO_2$

A suspension of rac-5-chloro-3-hydroxy-3-(4-methoxy-phenyl)-1,3-dihydro-indol-2-one (1.0 g, 3.45 mmol) (from Example 1a supra) in a mixture of triethylsilane (2 mL, 12.5 mmol) (Aldrich) and trifluoroacetic acid (5 mL, 65 mmol) was heated at 100° C. for 24 hours. After cooling, mixture was diluted with toluene and concentrated to almost dryness. Residue was dissolved in dichloromethane and purified by flash chromatography (Biotage 40M, 5% then 10% ethyl acetate in dichloromethane as solvent). Fractions containing product were combined and concentrated. Residue was recrystallized from dichloromethane-hexanes in two crops to give rac-5-chloro-3-(4-methoxy-phenyl)-1,3-dihydro-indol-2-one as white needles. (Yield 0.60 g, 63.5%).

HRMS(EI$^+$) m/z Calcd for $C_{15}H_{12}ClNO_2$ [M$^+$]: 273.0557. Found: 273.0555.

EXAMPLE 1c rac-3-Benzyl-5-chloro-3-(4-methoxy-phenyl)-1,3-dihydro-indol-2-one

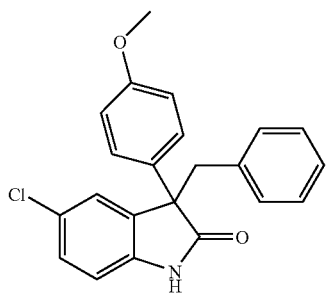

M.W. 363.85 $C_{22}H_{18}ClNO_2$

A mixture of rac-5-chloro-3-(4-methoxy-phenyl)-1,3-dihydro-indol-2-one (0.15 g, 0.55 mmol) (from Example 1b supra), benzyl bromide (113 mg, 0.65 mmol), potassium iodide (108 mg, 0.65 mmol) and potassium carbonate (163 mg, 1.18 mmol) in acetone (5 mL) was heated at 60° C. for 20 hours. After cooling, mixture was diluted with ethyl acetate (50 mL) and extracted with water (50 mL) and brine (50 mL). Aqueous layers were back washed with ethyl acetate (50 mL). Organic layers were combined, dried (MgSO$_4$), filtered and concentrated. Residue was purified by flash chromatography (Biotage 40S, dichloro-methane as solvent) to give two products. Lower Rf sample was recrystallized from ethyl acetate-hexanes to give rac-3-benzyl-5-chloro-3-(4-methoxy-phenyl)-1,3-dihydro-indol-2-one as white crystals. (Yield 58 mg, 29.1%).

HRMS(EI$^+$) m/z Calcd for $C_{22}H_{18}ClNO_2$ [M$^+$]: 363.1026. Found: 363.1020.

EXAMPLE 1d rac-1,3-Dibenzyl-5-chloro-3-(4-methoxy-phenyl)-1,3-dihydro-indol-2-one

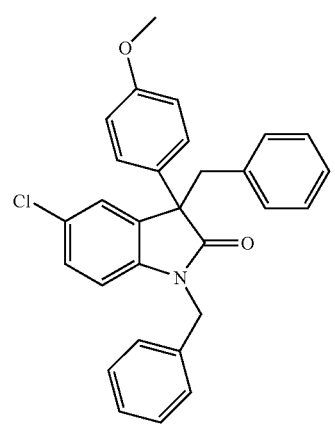

M.W. 453.97 $C_{29}H_{24}ClNO_2$

Faster eluting fraction from above example (Example 1c supra) was recrystallized from dichloromethane—hexanes to give rac-1,3-dibenzyl-5-chloro-3-(4-methoxy-phenyl)-1,3-dihydro-indol-2-one as white prisms. (Yield 40 mg, 16.1%).

HRMS(ES$^+$) m/z Calcd for $C_{29}H_{24}ClNO_2$+H [(M+H)$^+$]: 454.1569. Found: 454.1569.

EXAMPLE 2

6-Chloro-3,3-bis-(3-chloro-benzyl)-1,3-dihydro-indol-2-one

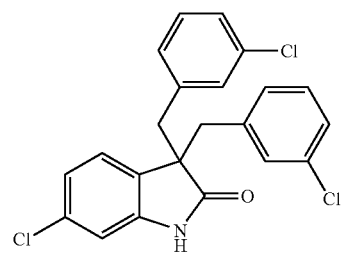

M.W. 416.74 $C_{22}H_{16}Cl_3NO$

A mixture of 6-chlorooxindole (0.42 g, 2.5 mmol) (Crescent), 3-chlorobenzyl bromide (1.13 g, 5.5 mmol) (Aldrich), potassium iodide (1.04 g, 6.25 mmol) and potassium carbonate (1.04 g, 7.5 mmol) in acetone (10 mL) was heated at 60° C. for 20 hours in a sealed tube. After cooling, mixture was diluted with ethyl acetate (50 mL) and extracted with water (50 mL) and brine (50 mL). Aqueous layers were back washed with ethyl acetate (50 mL). Organic layers were combined, dried (MgSO$_4$), filtered and concentrated. Residue was recrystallized from ethyl acetate-hexanes to give 6-chloro-3,3-bis-(3-chlorobenzyl)-1,3-dihydro-indol-2-one as white needles. (Yield 0.31 g, 29.8%).

HRMS(ES$^+$) m/z Calcd for C$_{22}$H$_{16}$Cl$_3$NO+H [(M+H)$^+$]: 416.0370. Found: 416.0370.

EXAMPLE 3a rac-6-Chloro-3-cyclopentyl-3-hydroxy-1,3-dihydro-indol-2-one

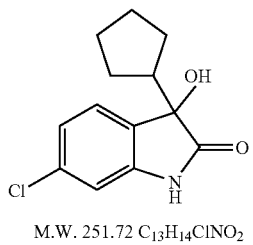

M.W. 251.72 C$_{13}$H$_{14}$ClNO$_2$

A solution of cyclopentyl magnesium bromide in ether (2.0 M, 12.5 mL, 25 mmol) (Aldrich) was added dropwise to a suspension of 6-chloroisatin (1.82 g, 10 mmol) (prepared according to the procedure of Kraynack, E. A. et al., supra) in tetrahydrofuran (40 mL) under argon with cooling in a −25° C. bath and magnetic stirring at such a rate that reaction temperature was kept below −10° C. (approximately 30 minutes). Cooling bath was then removed and mixture allowed to warm to room temperature. After stirring for an additional 1 hour, 15% aqueous ammonium chloride solution (50 mL) was added and mixture extracted with ethyl acetate (2×75 mL). Ethyl acetate layers were then washed with water (75 mL), brine (75 mL), combined, dried (MgSO$_4$), filtered and concentrated. Residue was stirred in dichloromethane (100 mL) at room temperature for 30 minutes and filtered to give crude rac-6-chloro-3-cyclopentyl-3-hydroxy-1,3-dihydro-indol-2-one as a white powder. (Yield 0.62 g, 24.6%).

EXAMPLE 3b rac-6-Chloro-3-cyclopentyl-1,3-dihydro-indol-2-one

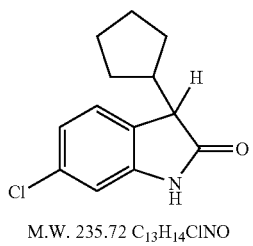

M.W. 235.72 C$_{13}$H$_{14}$ClNO

A suspension of rac-6-chloro-3-cyclopentyl-3-hydroxy-1,3-dihydro-indol-2-one (1.0 g, 4 mmol) (from Example 3a, supra) in a mixture of triethylsilane (2 mL, 12.5 mmol) (Aldrich) and trifluoroacetic acid (5 mL, 65 mmol) was heated in a 100° C. bath for 48 hours. After cooling to room temperature, mixture was diluted with ethyl acetate (50 mL). Solid potassium carbonate was added and mixture stirred at room temperature for 1 hour. Mixture was filtered and concentrated. Residue was redissolved in ethyl acetate and adsorbed onto silica gel (10 g). Solvent was evaporated off. Material was purified by flash chromatography (Biotage 40 M, 5% then 10% ethyl acetate in dichloromethane as solvent). Main product fractions were collected and concentrated to give rac-6-chloro-3-cyclopentyl-1,3-dihydro-indol-2-one as a dark purple solid. (Yield 0.24 g, 25.6%).

HRMS(EI$^+$) m/z Calcd for C$_{13}$H$_{14}$ClNO [M$^+$]: 235.0764. Found: 235.0764.

EXAMPLE 3c rac-3-Benzyl-6-chloro-3-cyclopentyl-1,3-dihydro-indol-2-one

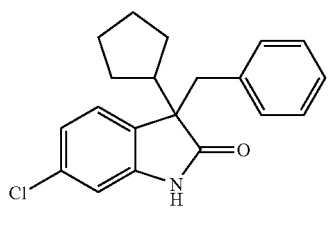

M.W. 325.84 C$_{20}$H$_{20}$ClNO

A mixture of rac-6-chloro-3-cyclopentyl-1,3-dihydro-indol-2-one (0.24 g, 1 mmol) (from Example 3b, supra), benzyl bromide (0.21 g, 1.2 mmol), potassium iodide (0.20 g, 1.2 mmol) and potassium carbonate (0.3 g, 2.2 mmol) in acetone (6 mL) was heated at 60° C. for 13 days in a capped pressure tube. After cooling, mixture was diluted with ethyl acetate (50 mL) and extracted with water (2×50 mL) and brine (50 mL). Aqueous layers were back washed with ethyl acetate (50 mL). Organic layers were combined, dried (MgSO$_4$), filtered and concentrated. Residue was purified by flash chromatography (Biotage 40S, dichloromethane, then 3% ethyl acetate in dichloromethane as solvent) to give two products. Lower Rf sample was recrystallized from dichloromethane-hexanes to give rac-3-benzyl-6-chloro-3-cyclopentyl-1,3-dihydro-indol-2-one as white prisms. (Yield 0.13 g, 39.2%).

HRMS(ES$^+$) m/z Calcd for C$_{20}$H$_{20}$ClNO+H [(M+H)$^+$]: 326.1306. Found: 326.1307.

EXAMPLE 3d rac-1,3-Dibenzyl-6-chloro-3-cyclopentyl-1,3-dihydro-indol-2-one

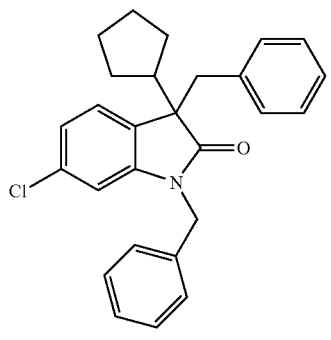

M.W. 415.97 C$_{27}$H$_{26}$ClNO

Faster eluting fraction from above example (from Example 3c supra) was recrystallized from dichloromethane-hexanes to give rac-1,3-dibenzyl-6-chloro-3-cyclopentyl-1,3-dihydro-indol-2-one as white prisms. (Yield 0.05 g, 11.8%).

HRMS(ES$^+$) m/z Calcd for $C_{27}H_{26}ClNO+H$ [(M+H)$^+$]: 416.1776. Found: 416.1778.

EXAMPLE 4a rac-6-Chloro-3-hydroxy-3-(4-methoxy-phenyl)-1,3-dihydro-indol-2-one

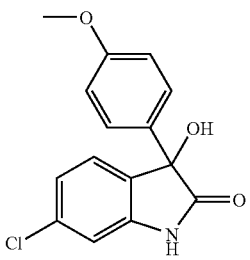

M.W. 289.72 $C_{15}H_{12}ClNO_3$

Sodium hydride (60% in oil, 0.3 g, 7.5 mmol) (Aldrich) was added to a suspension of 6-chloroisatin (1.82 g, 10 mmol) in tetrahydrofuran (30 mL) under argon with cooling in a −25° C. bath and magnetic stirring. After 10 minutes, a solution of 4-methoxyphenyl magnesium bromide in tetrahydrofuran (0.5 M, 40 mL, 20 mmol) (Aldrich) was added dropwise at such a rate that reaction temperature was kept below −10° C. (approximately 30 minutes). Cooling bath was then removed and mixture allowed to warm to room temperature. After stirring for an additional 2 hour, 15% aqueous ammonium chloride solution (25 mL) and water (50 mL) were added and mixture extracted with ethyl acetate (2×75 mL). Ethyl acetate layers were then washed with water (75 mL), brine (75 mL), combined, dried (MgSO$_4$), filtered and concentrated. Residue was stirred in dichloromethane (100 mL) at room temperature for 15 minutes and filtered to give crude rac-6-chloro-3-hydroxy-3-(4-methoxy-phenyl)-1,3-dihydro-indol-2-one as an off-white powder. This was used in the next step without further purification.

EXAMPLE 4b rac-6-Chloro-3-(4-methoxy-phenyl)-1,3-dihydro-indol-2-one

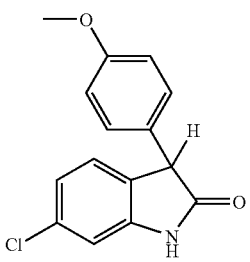

M.W. 273.72 $C_{15}H_{12}ClNO_2$ rac-6-Chloro-3-hydroxy-3-(4-methoxy-phenyl)-1,3-dihydro-indol-2-one (from Example 4a supra) was suspended in a mixture of triethylsilane (5 mL, 31.3 mmol) (Aldrich) and trifluoroacetic acid (12.5 mL) and heated in an 90° C. oil bath for 17 hours. After cooling to room temperature, mixture was diluted with ethyl acetate (100 mL) and treated with solid sodium carbonate (10.5 g). After stirring for 30 minutes, mixture was extracted with water (2×100 mL) and brine (100 mL). Aqueous layers were back washed with ethyl acetate (100 mL). Organic layers were combined, dried (MgSO$_4$), filtered and concentrated. Residue was purified by flash chromatography (Biotage 40M, dichloromethane then 10% ethyl acetate in dichloromethane as solvent). Fractions containing product were combined, concentrated and recrystallized from dichloromethane-hexanes to give rac-6-chloro-3-(4-methoxy-phenyl)-1,3-dihydro-indol-2-one as white needles. (Yield 2.26 g, 82.6% over two steps).

HRMS(ES$^+$) m/z Calcd for $C_{15}H_{12}ClNO_2+H$ [(M+H)$^+$]: 274.0630. Found: 274.0629.

EXAMPLE 4c rac-3-Benzyl-6-chloro-3-(4-methoxy-phenyl)-1,3-dihydro-indol-2-one

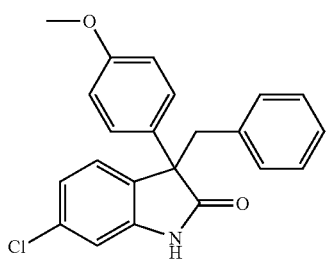

M.W. 363.85 $C_{22}H_{18}ClNO_2$

A mixture of rac-6-chloro-3-(4-methoxy-phenyl)-1,3-dihydro-indol-2-one (0.16 g, 0.6 mmol) (from Example 4b supra), benzyl bromide (0.12 g, 0.7 mmol) (Aldrich), potassium iodide (0.12 g, 0.71 mmol) and potassium carbonate (0.18 g, 1.3 mmol) in acetone (5 mL) was heated at 60° C. for 23 hours in a capped pressure tube. After cooling, mixture was diluted with ethyl acetate (50 mL) and extracted with water (2×50 mL) and brine (50 mL). Aqueous layers were back washed with ethyl acetate (50 mL). Organic layers were combined, dried (MgSO$_4$), filtered and concentrated. Residue was purified by flash chromatography (Biotage 40S, dichloromethane, then 5% ethyl acetate in dichloromethane as solvent) to give product. Attempts to recrystallize the product failed. Sample was concentrated to give rac-3-benzyl-6-chloro-3-(4-methoxy-phenyl)-1,3-dihydro-indol-2-one as a colorless glass. (Yield 0.17 g, 77.9%).

HRMS(ES$^+$) m/z Calcd for $C_{22}H_{18}ClNO_2+H$ [(M+H)$^+$]: 364.1099. Found: 364.1099.

EXAMPLE 5a rac-6-Chloro-3-(3-chloro-phenyl)-3-hydroxy-1,3-dihydro-indol-2-one

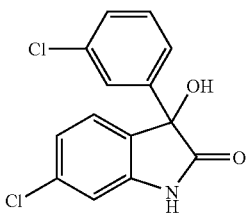

M.W. 294.14 C$_{14}$H$_9$C$_{12}$NO$_2$

A solution of 3-chlorophenyl magnesium bromide in tetrahydrofuran (0.5 M, 50 mL, 25 mmol) (Aldrich) was added dropwise with magnetic stirring to a suspension of 6-chloroisatin (1.82 g, 10 mmol) in tetrahydrofuran (20 mL) under argon with cooling in a −25° C. bath at such a rate that reaction temperature was kept below −10° C. (approximately 30 minutes). Cooling bath was then removed and mixture allowed to warm to room temperature. After stirring for an additional 2 hour, 15% aqueous ammonium chloride solution (25 mL) and water (50 mL) were added and mixture extracted with ethyl acetate (2×75 mL). Ethyl acetate layers were then washed with water (75 mL), brine (75 mL), combined, dried (MgSO$_4$), filtered and concentrated. Residue was stirred in dichloromethane (100 mL) at room temperature for 15 minutes and filtered to give crude rac-6-chloro-3-(3-chloro-phenyl)-3-hydroxy-1,3-dihydro-indol-2-one as an off-white powder. This was used in the next step without further purification.

EXAMPLE 5b rac-6-Chloro-3-(3-chloro-phenyl)-1,3-dihydro-indol-2-one

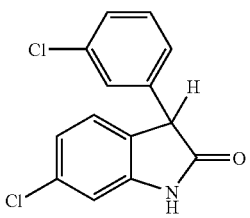

M.W. 278.14 C$_{14}$H$_9$Cl$_2$NO

Crude rac-6-chloro-3-(3-chloro-phenyl)-3-hydroxy-1,3-dihydro-indol-2-one (from Example 5a supra) was suspended in a mixture of triethylsilane (5 mL, 31.3 mmol) (Aldrich) and trifluoroacetic acid (12.5 mL) and heated in an 90° C. oil bath for 17 hours. After cooling to room temperature, mixture was diluted with ethyl acetate (100 mL) and treated with solid sodium carbonate (10.5 g). After stirring for 30 minutes, mixture was extracted with water (2×100 mL) and brine (100 mL). Aqueous layers were back washed with ethyl acetate (100 mL). Organic layers were combined, dried (MgSO$_4$), filtered and concentrated. Residue was purified by flash chromatography (Biotage 40M, dichloromethane then 7.5% ethyl acetate in dichloromethane as solvent). Fractions containing product were combined, concentrated and recrystallized from dichloromethane-hexanes to give rac-6-chloro-3-(3-chloro-phenyl)-1,3-dihydro-indol-2-one as white needles. (Yield 2.03 g, 73.0% over two steps).

HRMS(ES$^+$) m/z Calcd for C$_{14}$H$_9$Cl$_2$NO+H [(M+H)$^+$]: 278.0134. Found: 278.0134.

EXAMPLE 5c rac-3-Benzyl-6-chloro-3-(3-chloro-phenyl)-1,3-dihydro-indol-2-one

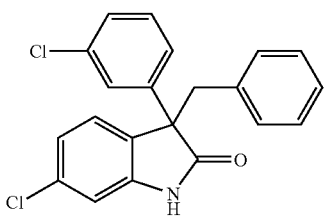

M.W. 368.27 C$_{21}$H$_{15}$Cl$_2$NO

A mixture of rac-6-chloro-3-(3-chloro-phenyl)-1,3-dihydro-indol-2-one (0.17 g, 0.6 mmol) (from Example 5b supra), benzyl bromide (0.12 g, 0.7 mmol) (Aldrich), potassium iodide (0.12 g, 0.71 mmol) and potassium carbonate (0.18 g, 1.3 mmol) in acetone (5 mL) was heated at 60° C. for 5 hours in a capped pressure tube. After cooling, mixture was diluted with ethyl acetate (50 mL) and extracted with water (2×50 mL) and brine (50 mL). Aqueous layers were back washed with ethyl acetate (50 mL). Organic layers were combined, dried (MgSO$_4$), filtered and concentrated. Residue was purified by flash chromatography (Biotage 40S, dichloromethane, then 5% ethyl acetate in dichloromethane as solvent) to give two products. Lower Rf sample was recrystallized from dichloromethane-hexanes to give rac-3-benzyl-6-chloro-3-(3-chloro-phenyl)-1,3-dihydro-indol-2-one as white needles. (Yield 0.17 g, 76.9%).

HRMS(ES$^+$) m/z Calcd for C$_{21}$H$_{15}$Cl$_2$NO+H [(M+H)$^+$]: 368.0604. Found: 368.0605.

EXAMPLE 6a rac-6-Chloro-3-hydroxy-3-(3-methoxy-phenyl)-1,3-dihydro-indol-2-one

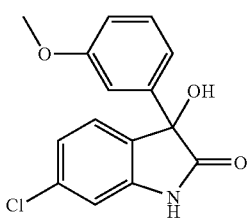

M.W. 289.72 C$_{15}$H$_{12}$ClNO$_3$

A solution of 3-methoxyphenyl magnesium bromide in tetrahydrofuran (1.0 M, 25 mL, 25 mmol) (Aldrich) was added dropwise with magnetic stirring to a suspension of 6-chloroisatin (1.82 g, 10 mmol) in tetrahydrofuran (40 mL) under argon with cooling in a −25° C. bath at such a rate that reaction temperature was kept below −10° C. (approximately 30 minutes). Cooling bath was then removed and mixture allowed to warm to room temperature. After stirring for an additional 2 hour, 15% aqueous ammonium chloride solution (25 mL) and water (50 mL) were added and mixture extracted with ethyl acetate (2×75 mL). Ethyl acetate layers were then washed with water (75 mL), brine (75 mL), combined, dried (MgSO$_4$), filtered and concentrated. Residue was stirred in dichloromethane (100 mL) at room temperature for 15 minutes and filtered to give crude rac-6-chloro-3-hydroxy-3-(3-methoxy-phenyl)-1,3-dihydro-indol-2-one as an off-white powder. This was used in the next step without further purification.

EXAMPLE 6b rac-6-Chloro-3-(3-methoxy-phenyl)-1,3-dihydro-indol-2-one

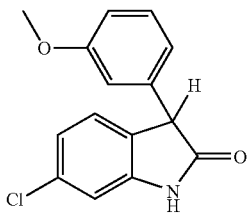

M.W. 273.72 C$_{15}$H$_{12}$ClNO$_2$

Crude rac-6-chloro-3-hydroxy-3-(3-methoxy-phenyl)-1,3-dihydro-indol-2-one (from Example 6a supra) was suspended in a mixture of triethylsilane (5 mL, 31.3 mmol) (Aldrich) and trifluoroacetic acid (12.5 mL) and heated in an 90° C. oil bath for 17 hours. After cooling to room temperature, mixture was diluted with ethyl acetate (100 mL) and treated with solid sodium carbonate (10.5 g). After stirring for 30 minutes, mixture was extracted with water (2×100 mL) and brine (100 mL). Aqueous layers were back washed with ethyl acetate (100 mL). Organic layers were combined, dried (MgSO$_4$), filtered and concentrated. Residue was recrystallized from dichloromethane-hexanes to give rac-6-chloro-3-(3-methoxy-phenyl)-1,3-dihydro-indol-2-one as off-white prisms. (Yield 2.12 g, 77.4% over two steps).

HRMS(ES$^+$) m/z Calcd for C$_{15}$H$_{12}$ClNO$_2$+H [(M+H)$^+$]: 274.0630. Found: 274.0629.

EXAMPLE 6c rac-3-Benzyl-6-chloro-3-(3-methoxy-phenyl)-1,3-dihydro-indol-2-one

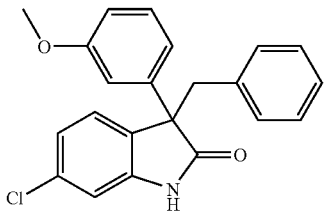

M.W. 363.85 C$_{22}$H$_{18}$ClNO$_2$

A mixture of rac-6-chloro-3-(3-methoxy-phenyl)-1,3-dihydro-indol-2-one (0.16 g, 0.6 mmol) (from Example 6b supra), benzyl bromide (0.12 g, 0.7 mmol) (Aldrich), potassium iodide (0.12 g, 0.71 mmol) and potassium carbonate (0.18 g, 1.3 mmol) in acetone (5 mL) was heated at 60° C. for 23 hours in a capped pressure tube. After cooling, mixture was diluted with ethyl acetate (50 mL) and extracted with water (2×50 mL) and brine (50 mL). Aqueous layers were back washed with ethyl acetate (50 mL). Organic layers were combined, dried (MgSO$_4$), filtered and concentrated. Residue was purified by flash chromatography (Biotage 40S, dichloromethane, then 5% ethyl acetate in dichloromethane as solvent) to give two products. Lower Rf sample was recrystallized from dichloromethane-hexanes to give rac-3-benzyl-6-chloro-3-(3-methoxy-phenyl)-1,3-dihydro-indol-2-one as white needles. (Yield 0.16 g, 73.3%).

HRMS(ES$^+$) m/z Calcd for C$_{22}$H$_{18}$ClNO$_2$+H [(M+H)$^+$]: 364.1099. Found: 364.1100.

EXAMPLE 7a rac-6-Chloro-3-(4-chloro-phenyl)-3-hydroxy-1,3-dihydro-indol-2-one

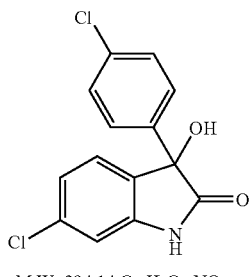

M.W. 294.14 C$_{14}$H$_9$C$_{12}$NO$_2$

A solution of 4-chlorophenyl magnesium bromide in diethyl ether (1.0 M, 25 mL, 25 mmol) (Aldrich) was added dropwise with magnetic stirring to a suspension of 6-chloroisatin (1.82 g, 10 mmol) in tetrahydrofuran (40 mL) under argon with cooling in a −25° C. bath at such a rate that reaction temperature was kept below −10° C. (approximately 30 minutes). Cooling bath was then removed and mixture allowed to warm to room temperature. After stirring for an additional 2 hour, 15% aqueous ammonium chloride solution (25 mL) and water (50 mL) were added and mixture extracted with ethyl acetate (2×75 mL). Ethyl acetate layers were then washed with water (75 mL), brine (75 mL), combined, dried (MgSO$_4$), filtered and concentrated. Residue was stirred in dichloromethane (100 mL) at room temperature for 15 minutes and filtered to give crude rac-6-chloro-3-(4-chloro-phenyl)-3-hydroxy-1,3-dihydro-indol-2-one as an off-white powder. This was used in the next step without further purification.

EXAMPLE 7b rac-6-Chloro-3-(4-chloro-phenyl)-1,3-dihydro-indol-2-one

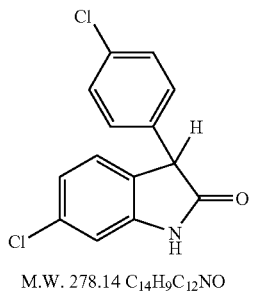

M.W. 278.14 C$_{14}$H$_9$Cl$_2$NO

Crude rac-6-chloro-3-(4-chloro-phenyl)-3-hydroxy-1,3-dihydro-indol-2-one (from Example 7a supra) was suspended in a mixture of triethylsilane (5 mL, 31.3 mmol) (Aldrich) and trifluoroacetic acid (12.5 mL) and heated in an 90° C. oil bath for 17 hours. After cooling to room temperature, mixture was diluted with ethyl acetate (100 mL) and treated with solid sodium carbonate (10.5 g). After stirring for 30 minutes, mixture was extracted with water (2×100 mL) and brine (100 mL). Aqueous layers were back washed with ethyl acetate (100 mL). Organic layers were combined, dried (MgSO$_4$), filtered and concentrated. Residue was recrystallized from ethyl acetate-hexanes to give rac-6-chloro-3-(4-chloro-phenyl)-1,3-dihydro-indol-2-one as white needles. (Yield 2.20 g, 79.1% over two steps).

HRMS(ES$^+$) m/z Calcd for C$_{14}$H$_9$Cl$_2$NO+H [(M+H)$^+$]: 278.0134. Found: 278.0134.

EXAMPLE 7c rac-3-Benzyl-6-chloro-3-(4-chloro-phenyl)-1,3-dihydro-indol-2-one

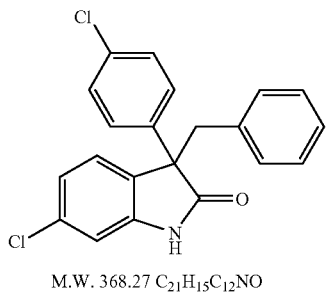

M.W. 368.27 C$_{21}$H$_{15}$Cl$_2$NO

A mixture of rac-6-chloro-3-(4-chloro-phenyl)-1,3-dihydro-indol-2-one (0.17 g, 0.6 mmol) (from Example 7b supra), benzyl bromide (0.12 g, 0.7 mmol) (Aldrich), potassium iodide (0.12 g, 0.71 mmol) and potassium carbonate (0.18 g, 1.3 mmol) in acetone (5 mL) was heated at 60° C. for 5 hours in a capped pressure tube. Mixture was then stirred at room temperature over night and then diluted with ethyl acetate (50 mL) and extracted with water (2×50 mL) and brine (50 mL). Aqueous layers were back washed with ethyl acetate (50 mL). Organic layers were combined, dried (MgSO$_4$), filtered and concentrated. Residue was purified by flash chromatography (Biotage 40S, dichloromethane, then 5% ethyl acetate in dichloromethane as solvent) to give two products. Lower Rf sample was recrystallized from ethyl acetate-hexanes to give rac-3-benzyl-6-chloro-3-(4-chloro-phenyl)-1,3-dihydro-indol-2-one as white plates. (Yield 0.16 g, 72.4%).

HRMS(ES$^+$) m/z Calcd for C$_{21}$H$_{15}$Cl$_2$NO+H [(M+H)$^+$]: 368.0604. Found: 368.0604.

EXAMPLE 8 rac-6-Chloro-3-(4-chloro-benzyl)-3-(3-methoxy-phenyl)-1,3-dihydro-indol-2-one

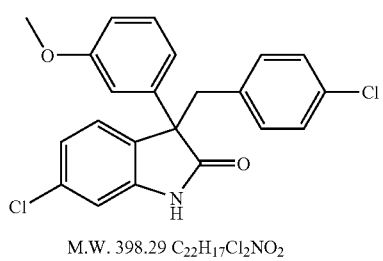

M.W. 398.29 C$_{22}$H$_{17}$Cl$_2$NO$_2$

A mixture of rac-6-chloro-3-(3-methoxy-phenyl)-1,3-dihydro-indol-2-one (0.16 g, 0.6 mmol) (from Example 6b supra), 4-chlorobenzyl bromide (0.15 g, 0.7 mmol) (Lancaster), potassium iodide (0.12 g, 0.71 mmol) and potassium carbonate (0.18 g, 1.3 mmol) in acetone (5 mL) was heated at 60° C. for 6 hours in a capped pressure tube. After cooling, mixture was diluted with ethyl acetate (50 mL) and extracted with water (2×50 mL) and brine (50 mL). Aqueous layers were back washed with ethyl acetate (50 mL). Organic layers were combined, dried (MgSO$_4$), filtered and concentrated. Residue was recrystallized from dichloromethane-hexanes to give rac-6-chloro-3-(4-chloro-benzyl)-3-(3-methoxy-phenyl)-1,3-dihydro-indol-2-one as white crystals. (Yield 0.18 g, 75.3%).

HRMS(ES$^+$) m/z Calcd for C$_{22}$H$_{17}$Cl$_2$NO$_2$+H [(M+H)$^+$]: 398.0709. Found: 398.0714.

EXAMPLE 9 rac-6-Chloro-3-(3-chloro-benzyl)-3-(3-methoxy-phenyl)-1,3-dihydro-indol-2-one

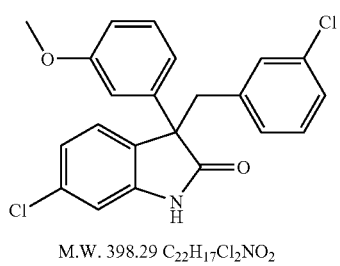

M.W. 398.29 C$_{22}$H$_{17}$Cl$_2$NO$_2$

A mixture of 6-chloro-3-(3-methoxy-phenyl)-1,3-dihydro-indol-2-one (0.16 g, 0.6 mmol) (from Example 6b supra), 3-chlorobenzyl bromide (0.15 g, 0.7 mmol)(Aldrich), potassium iodide (0.12 g, 0.71 mmol) and potassium carbonate (0.18 g, 1.3 mmol) in acetone (5 mL) was heated at 60° C. for 4 hours in a capped pressure tube. After cooling, mixture was diluted with ethyl acetate (50 mL) and extracted with water (2×50 mL) and brine (50 mL). Aqueous layers were back washed with ethyl acetate (50 mL). Organic layers were combined, dried (MgSO$_4$), filtered and concentrated. Residue was recrystallized from dichloromethane-hexanes to give rac-6-chloro-3-(3-chloro-benzyl)-3-(3-methoxy-phenyl)-1,3-dihydro-indol-2-one as white needles. (Yield 0.18 g, 75.3%).

HRMS(ES$^+$) m/z Calcd for C$_{22}$H$_{17}$Cl$_2$NO$_2$+H [(M+H)$^+$]: 398.0709. Found: 398.0709.

EXAMPLE 10 rac-6-Chloro-3-(4-methoxy-benzyl)-3-(3-methoxy-phenyl)-1,3-dihydro-indol-2-one

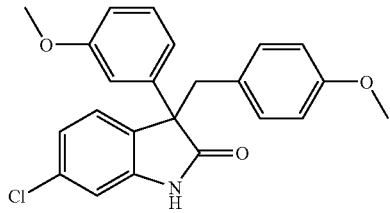

M.W. 393.87 C$_{23}$H$_{20}$ClNO$_3$

A mixture of rac-6-chloro-3-(3-methoxy-phenyl)-1,3-dihydro-indol-2-one (0.16 g, 0.6 mmol) (from Example 6b supra), 4-methoxybenzyl chloride (0.15 g, 0.7 mmol) (Aldrich), potassium iodide (0.12 g, 0.71 mmol) and potassium carbonate (0.18 g, 1.3 mmol) in acetone (5 mL) was heated at 60° C. for 4 hours in a capped pressure tube. After cooling, mixture was diluted with ethyl acetate (50 mL) and extracted with water (2×50 mL) and brine (50 mL). Aqueous layers were back washed with ethyl acetate (50 mL). Organic layers were combined, dried (MgSO$_4$), filtered and concentrated. Residue was recrystallized from dichloromethane-hexanes to give rac-6-chloro-3-(4-methoxy-benzyl)-3-(3-methoxy-phenyl)-1,3-dihydro-indol-2-one as white needles. (Yield 0.19 g, 80.4%).

HRMS(ES$^+$) m/z Calcd for C$_{23}$H$_{20}$ClNO$_3$+H [(M+H)$^+$]: 394.1205. Found: 394.1207.

EXAMPLE 11 rac-6-Chloro-3-(3-methoxy-benzyl)-3-(3-methoxy-phenyl)-1,3-dihydro-indol-2-one

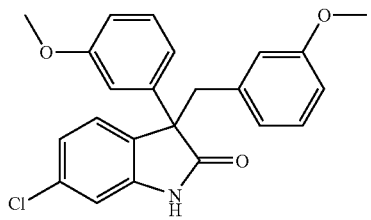

M.W. 393.87 C$_{23}$H$_{20}$ClNO$_3$

A mixture of rac-6-chloro-3-(3-methoxy-phenyl)-1,3-dihydro-indol-2-one (0.16 g, 0.6 mmol) (from Example 6b supra), 3-methoxybenzyl bromide (0.15 g, 0.7 mmol) (Aldrich), potassium iodide (0.12 g, 0.71 mmol) and potassium carbonate (0.18 g, 1.3 mmol) in acetone (5 mL) was heated at 60° C. for 4 hours in a capped pressure tube. After cooling, mixture was diluted with ethyl acetate (50 mL) and extracted with water (2×50 mL) and brine (50 mL). Aqueous layers were back washed with ethyl acetate (50 mL). Organic layers were combined, dried (MgSO$_4$), filtered and concentrated. Residue was recrystallized from dichloromethane-hexanes to give rac-6-chloro-3-(3-methoxy-benzyl)-3-(3-methoxy-phenyl)-1,3-dihydro-indol-2-one as orange plates. (Yield 0.19 g, 80.4%).

HRMS(ES$^+$) m/z Calcd for C$_{23}$H$_{20}$ClNO$_3$+H [(M+H)$^+$]: 394.1205. Found: 394.1204.

EXAMPLE 12a 4-(6-Chloro-2-oxo-1,2-dihydro-indol-3-ylidene)-piperidine-1-carboxylic acid tert-butyl ester

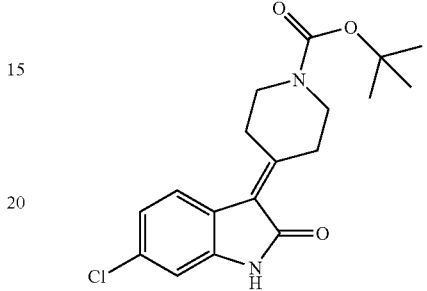

M.W. 348.83 C$_{18}$H$_{21}$ClN$_2$O$_3$

A suspension of 6-chlorooxindole (1.68 g, 10 mmol) (Cresent Chem.), 1-BOC-4-piperidone (2.20 g, 11.0 mmol) (Fluka), and piperidine (85 mg, 1 mmol) (Aldrich) in 2-propanol (30 mL) was heated at 100° C. for 2 days. Hot water (30 mL) was added to the hot reaction mixture and mixture allowed to cool to room temperature. After standing in refrigerator for 2 hours, crystalline material was collected and washed with cold aqueous methanol to give 4-(6-chloro-2-oxo-1,2-dihydro-indol-3-ylidene)-piperidine-1-carboxylic acid tert-butyl ester as a yellow crystalline material. (Yield 2.88 g, 82.4%).

HRMS(ES$^+$) m/z Calcd for C$_{18}$H$_{21}$ClN$_2$O$_3$+Na [(M+Na)$^+$]: 371.1133. Found: 371.1135.

EXAMPLE 12b rac-4-(6-Chloro-2-oxo-2,3-dihydro-1H-indol-3-yl)-piperidine-1-carboxylic acid tert-butyl ester

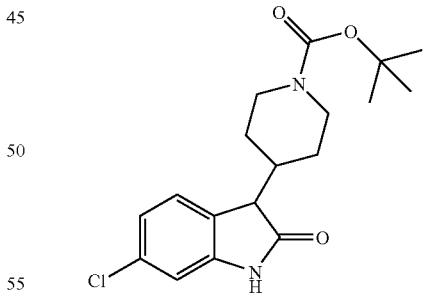

M.W. 350.85 C$_{18}$H$_{23}$ClN$_2$O$_3$

Sodium borohydride (0.38 g, 10 mmol) (Aldrich) was added in small portions to a solution of 4-(6-chloro-2-oxo-1,2-dihydro-indol-3-ylidene)-piperidine-1-carboxylic acid tert-butyl ester (0.35 g, 1 mmol) (from Example 12a supra) in methanol (25 mL) and water (3 mL) at such a rate that gas evolution was not too vigorous. When addition was complete, mixture was heated at 40° C. for 1 hour. After cooling, mixture was slowly diluted with water. Precipitate formed was collected by filtration and washed with cold aqueous methanol to give rac-4-(6-chloro-2-oxo-2,3-dihydro-1H-indol-3- yl)-piperidine-1-carboxylic acid tert-butyl ester as a white crystalline material. (Yield 0.33 g, 94.0%).

HRMS(ES$^+$) m/z Calcd for $C_{18}H_{23}ClN_2O_3$+Na [(M+Na)$^+$]: 373.1289. Found: 373.1290.

EXAMPLE 12c rac-4-[6-Chloro-3-(3-chloro-benzyl)-2-oxo-2,3-dihydro-1H-indol-3-yl]-piperidine-1-carboxylic acid tert-butyl ester

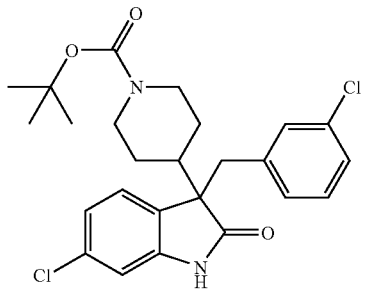

M.W. 475.42 $C_{25}H_{28}Cl_2N_2O_3$

A mixture of rac-4-(6-chloro-2-oxo-2,3-dihydro-1H-indol-3-yl)-piperidine-1-carboxylic acid tert-butyl ester (0.21 g, 0.6 mmol) (from Example 12b supra), 3-chlorobenzyl bromide (0.15 g, 0.7 mmol) (Aldrich), potassium iodide (0.12 g, 0.71 mmol) and potassium carbonate (0.18 g, 1.3 mmol) in acetone (5 mL) was heated at 60° C. for 8 hours in a capped pressure tube. After cooling, mixture was diluted with ethyl acetate (50 mL) and extracted with water (2×50 mL) and brine (50 mL). Aqueous layers were back washed with ethyl acetate (50 mL). Organic layers were combined, dried (MgSO$_4$), filtered and concentrated. Residue was purified by flash chromatography (Biotage 40S, 3% then 10% ethyl acetate in dichloromethane as solvent). Combined fractions were recrystallized from dichloromethane-hexanes to give rac-4-[6-chloro-3-(3-chloro-benzyl)-2-oxo-2,3-dihydro-1H-indol-3-yl]-piperidine-1-carboxylic acid tert-butyl ester as white crystals. (Yield 0.14 g, 49.1%).

HRMS(ES$^+$) m/z Calcd for $C_{25}H_{28}Cl_2N_2O_3$+Na [(M+Na)$^+$]: 497.1369. Found: 497.1371.

EXAMPLE 12d rac-4-[6-Chloro-1,3-bis-(3-chloro-benzyl)-2-oxo-2,3-dihydro-1H-indol-3-yl]-piperidine-1-carboxylic acid tert-butyl ester

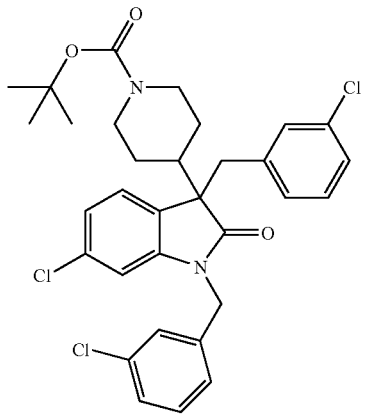

M.W. 599.99 $C_{32}H_{33}Cl_3N_2O_3$

Faster eluting fraction from above example (Example 12c supra) was recrystallized from dichloro-methane-hexanes to give rac-4-[6-chloro-1,3-bis-(3-chloro-benzyl)-2-oxo-2,3-dihydro-1H-indol-3-yl]-piperidine-1-carboxylic acid tert-butyl ester as white crystals. (Yield 0.09 g, 25.0%).

HRMS(ES$^+$) m/z Calcd for $C_{32}H_{33}Cl_3N_2O_3$+Na [(M+Na)$^+$]: 621.1449. Found: 621.1447.

EXAMPLE 13

(S)-6-Chloro-3-(3-chloro-benzyl)-3-(3-methoxy-phenyl)-1,3-dihydro-indol-2-one

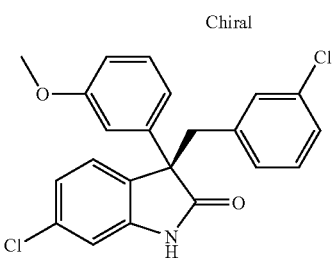

M.W. 398.29 $C_{22}H_{17}Cl_2NO_2$

A sample of rac-6-chloro-3-(3-chloro-benzyl)-3-(3-methoxy-phenyl)-1,3-dihydro-indol-2-one (100 mg) (from Example 9 supra) was separated by chiral column chromatography (Daicel OD column, hexanes-ethanol 4:6 as solvent) in three runs to give two components. Respective fractions of the two components in the three runs were combined and concentrated. Resulting materials were recrystallized from dichloromethane-hexanes to give (S)-6-chloro-3-(3-chloro-benzyl)-3-(3-methoxy-phenyl)-1,3-dihydro-indol-2-one as white crystals from the first eluted component. (Yield 34.6 mg, 34.6%).

HRMS(ES$^+$) m/z Calcd for $C_{22}H_{17}Cl_2NO_2$+H [(M+H)$^+$]: 398.0709. Found: 398.0710.

EXAMPLE 14a rac-6-Chloro-3-hydroxy-3-(1-methyl-1H-pyrazol-4-yl)-1,3-dihydro-indol-2-one

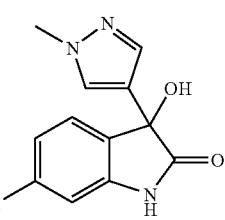

M.W. 263.69 $C_{12}H_{10}ClN_3O_2$

4-Bromo-1-methyl-1H-pyrazole was prepared according to the procedure of Dusza, J. P. et al., U.S. Pat. No. 6,511,974 B1, published Jan. 28, 2003.

To a solution of 4-bromo-1-methyl-1H-pyrazole (0.98 g, 6.0 mmol) in tetrahydrofuran (10 mL) at −78° C. was added n-butyllithium (2.5 M in hexanes, 2.76 mL, 6.90 mmol) (Aldrich) dropwisely. The mixture was stirred at −78° C. for 10 minutes. To the obtained brownish solution was added a solution of 6-chloroisatin (0.5 g, 2.76 mmol) (Crescent) in tetrahydrofuran (5 mL). The reaction mixture was warmed up to room temperature and stirred at room temperature for 3 hours. The reaction was quenched with saturated aqueous ammonium chloride solution. The mixture was extracted with ethyl acetate three times. The combined organic layers were washed with water, brine, dried over Na$_2$SO$_4$ and concentrated. The residue was purified by chromatography (ethyl acetate:dichloromethane, 1:1 V/V) to give rac-6-chloro-3-hydroxy-3-(1-methyl-1H-pyrazol-4-yl)-1,3-dihydro-indol-2-one as a yellow solid. (Yield 0.22 g, 30%).

EXAMPLE 14b rac-6-Chloro-3-(1-methyl-1H-pyrazol-4-yl)-1,3-dihydro-indol-2-one

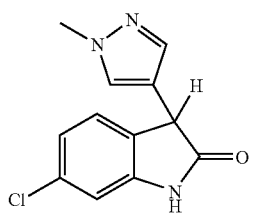

M.W. 247.69 C$_{12}$H$_{10}$ClN$_3$O rac-6-Chloro-3-hydroxy-3-(1-methyl-1H-pyrazol-4-yl)-1,3-dihydro-indol-2-one (0.22 g, 0.84 mmol) (from Example 14a supra) was suspended in a mixture of triethylsilane (0.40 mL, 2.52 mmol) (Aldrich) and trifluoroacetic acid (1.2 mL, 12.5 mmol) (Aldrich) and heated in an 90° C. oil bath for 17 hours. After cooling to room temperature, the mixture was diluted with ethyl acetate (10 mL) and treated with solid sodium carbonate (1.0 g). After stirring for 30 minutes, mixture was extracted with water and brine. Aqueous layers were back washed with ethyl acetate. Organic layers were combined, dried (Na$_2$SO$_4$), filtered and concentrated. Residue was triturated with dichloromethane-hexanes to give rac-6-chloro-3-(1-methyl-1H-pyrazol-4-yl)-1,3-dihydro-indol-2-one as a white solid. (Yield 0.1 g, 50%).

EXAMPLE 14c rac-6-Chloro-3-(3-chloro-benzyl)-3-(1-methyl-1H-pyrazol-4-yl)-1,3-dihydro-indol-2-one

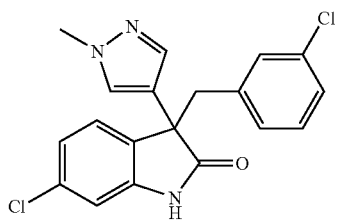

M.W. 372.257 C$_{19}$H$_{15}$Cl$_2$N$_3$O

A mixture of rac-6-chloro-3-(1-methyl-1H-pyrazol-4-yl)-1,3-dihydro-indol-2-one (0.1 g, 0.4 mmol) (from Example 14b supra), 3-chlorobenzyl bromide (0.098 g, 0.48 mmol) (Aldrich), potassium iodide (0.08 g, 0.481 mmol) and potassium carbonate (0.12 g, 0.87 mmol) in acetone (4 mL) was heated at 60° C. for 4 hours in a capped pressure tube. After cooling, the mixture was diluted with ethyl acetate and extracted with water and brine. Aqueous layers were back washed with ethyl acetate. Organic layers were combined, dried (Na$_2$SO$_4$), filtered and concentrated. The residue was purified by chromatography (ethyl acetate: dichloromethane, 1:1 V/V) to give rac-6-chloro-3-(3-chloro-benzyl)-3-[1-methyl-1H-pyrazol-4-yl]-1,3-dihydro-indol-2-one as a white solid. (Yield, 0.05 g, 33%).

HRMS(ES$^+$) m/z Calcd for C$_{19}$H$_{15}$Cl$_2$N$_3$O+H [(M+H)$^+$]: 372.0665. Found: 372.0665.

EXAMPLE 15a rac-6-Chloro-3-(3-chloro-benzyl)-3-piperidin-4-yl-1,3-dihydro-indol-2-one

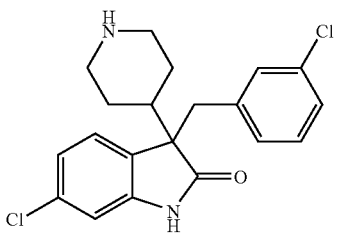

M.W. 375.301 C$_{20}$H$_{20}$Cl$_2$N$_2$O

Trifloroacetic Acid (5 mL) was added to a solution of rac-4-[6-chloro-3-(3-chloro-benzyl)-2-oxo-2,3-dihydro-1H-indol-3-yl]-piperidine-1-carboxylic acid tert-butyl ester (0.24 g, 0.5 mmol) (from Example 12c supra) in dichloromethane (5 mL). The mixture was stirred at room temperature for 30 minutes. The solvent was evaporated in vacuo. To the residue was added saturated aqueous sodium bicarbonate solution, and extracted three times with ethyl acetate. The organic layers were combined, washed with water and brine, dried over Na$_2$SO$_4$ and concentrated to give rac-6-chloro-3-(3-chlorobenzyl)-3-piperidin-4-yl-1,3-dihydro-indol-2-one as a white solid. (Yield 0.18 g, 95%).

HRMS(ES$^+$) m/z Calcd for C$_{20}$H$_{20}$Cl$_2$N$_2$O+H [(M+H)$^+$]: 375.1026. Found: 375.1025.

EXAMPLE 15b rac-3-(1-Acetyl-piperidin-4-yl)-6-chloro-3-(3-chloro-benzyl)-1,3-dihydro-indol-2-one

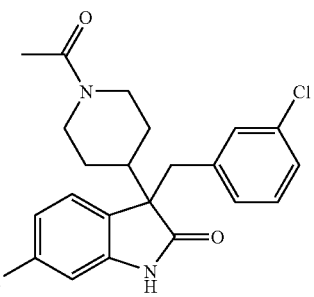

M.W. 417.339 C$_{22}$H$_{22}$Cl$_2$N$_2$O$_2$

To a solution of rac-6-chloro-3-(3-chloro-benzyl)-3-piperidin-4-yl-1,3-dihydro-indol-2-one (35 mg, 0.09 mmol) (from Example 15a supra) in tetrahydrofuran (3 mL) was added triethylamine (14.1 mg, 0.139 mmol), followed by the addition of acetyl chloride (8.7 mg, 0.11 mmol) (Aldrich). The mixture was stirred at room temperature for 30 minutes. The mixture was partitioned between ethyl acetate and water. The aqueous layer was extracted with another two portions of ethyl acetate. The combined organic layers were washed with water, brine, dried over $Na_2SO_4$ and concentrated to give rac-3-(1-acetyl-piperidin-4-yl)-6-chloro-3-(3-chloro-benzyl)-1,3-dihydro-indol-2-one as a white solid. (Yield 25 mg, 65%). Further purification by precipitation in a cosolvent of dichloromethane and hexanes gave the product as a white solid. (18 mg).

HRMS($ES^+$) m/z Calcd for $C_{22}H_{22}Cl_2N_2O_2$+H [$(M+H)^+$]: 417.1131. Found: 417.1129.

EXAMPLE 16 rac-4-[6-Chloro-3-(3-chloro-benzyl)-2-oxo-2,3-dihydro-1H-indol-3-yl]-piperidine-1-carboxylic acid methylamide

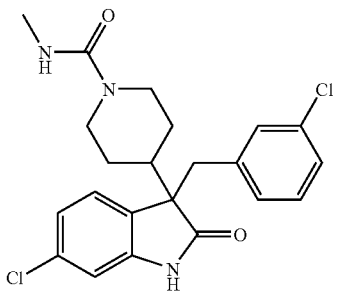

M.W. 432.354 $C_{22}H_{23}Cl_2N_3O_2$

To a solution of rac-6-chloro-3-(3-chloro-benzyl)-3-piperidin-4-yl-1,3-dihydro-indol-2-one (30 mg, 0.08 mmol) (from Example 15a supra) in chloroform (2 mL) was added isocyanatomethane (5.4 mg, 0.096 mmol) (Chem. Service). The mixture was stirred at room temperature for 16 hours. The solvent was evaporated and resulting material was recrystallized from dichloromethane-hexanes to give rac-4-[6-chloro-3-(3-chloro-benzyl)-2-oxo-2,3-dihydro-1H-indol-3-yl]-piperidine-1-carboxylic acid methylamide as a white solid. (Yield 5 mg, 14.5%).

HRMS($ES^+$) m/z Calcd for $C_{22}H_{23}Cl_2N_3O_2$+H [$(M+H)^+$]: 432.1240. Found: 432.1241.

EXAMPLE 17 rac-3-(3-Bromo-benzyl)-6-chloro-3-(3-methoxy-phenyl)-1,3-dihydro-indol-2-one

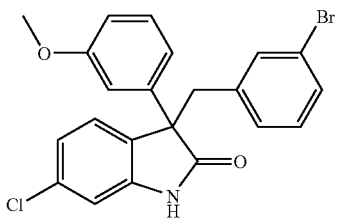

M.W. 442.743 $C_{22}H_{17}BrClNO_2$

A mixture of rac-6-chloro-3-(3-methoxy-phenyl)-1,3-dihydro-indol-2-one (40 mg, 0.15 mmol) (from Example 6b supra), 1-bromo-3-bromomethyl-benzene (43 mg, 0.17 mmol) (Aldrich), potassium iodide (29 mg, 0.17 mmol) and potassium carbonate (43 mg, 0.31 mmol) in acetone (2 mL) was heated at 60° C. for 16 hours in a capped pressure tube. After cooling, mixture was diluted with ethyl acetate and extracted with water and brine. Aqueous layers were back washed with ethyl acetate. Organic layers were combined, dried ($Na_2SO_4$), filtered and concentrated. Residue was recrystallized from dichloromethane-hexanes to give rac-3-(3-bromo-benzyl)-6-chloro-3-(3-methoxy-phenyl)-1,3-dihydro-indol-2-one as a white solid. (Yield 28 mg, 43%).

HRMS($ES^+$) m/z Calcd for $C_{22}H_{17}BrClNO_2$+H [$(M+H)^+$]: 442.0204. Found: 442.0204.

EXAMPLE 18 rac-6-Chloro-3-(3-fluoro-benzyl)-3-(3-methoxy-phenyl)-1,3-dihydro-indol-2-one

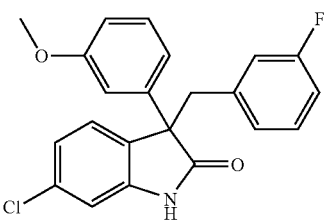

M.W. 381.838 $C_{22}H_{17}ClFNO_2$

A mixture of rac-6-chloro-3-(3-methoxy-phenyl)-1,3-dihydro-indol-2-one (50 mg, 0.18 mmol) (from Example 6b supra), 1-bromomethyl-3-fluoromethyl-benzene (41 mg, 0.21 mmol) (Aldrich), potassium iodide (36 mg, 0.21 mmol) and potassium carbonate (54 mg, 0.39 mmol) in acetone (2 mL) was heated at 60° C. for 3 hours in a capped pressure tube. After cooling, mixture was diluted with ethyl acetate and extracted with water and brine. Aqueous layers were back washed with ethyl acetate. Organic layers were combined, dried ($Na_2SO_4$), filtered and concentrated. Residue was recrystallized from dichloromethane-hexanes to give rac-6-chloro-3-(3-fluoro-benzyl)-3-(3-methoxy-phenyl)-1,3-dihydro-indol-2-one as a white solid. (Yield 25 mg, 36%).

HRMS($ES^+$) m/z Calcd for $C_{22}H_{17}ClFNO_2$+H [$(M+H)^+$]: 382.1005. Found: 382.1006.

EXAMPLE 19a rac-6-Chloro-3-cyclohexyl-3-hydroxy-1,3-dihydro-indol-2-one

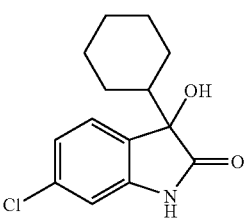

M.W. 265.74 $C_{14}H_{16}ClNO_2$

A solution of cyclohexyl magnesium bromide in ether (2.0 M, 3.10 mL, 6.25 mmol) (Aldrich) was added dropwise to a suspension of 6-chloroisatin (0.45 g, 2.5 mmol) (Crescent) in tetrahydrofuran (12.5 mL) with cooling in a −25° C. bath and magnetic stirring at such a rate that reaction temperature was kept below −10° C. Cooling bath was then removed and mixture was allowed to warm to room temperature. After stirring for an additional 2 hours, 15% aqueous ammonium chloride solution (12.5 mL) was added and mixture was extracted with ethyl acetate. Ethyl acetate layers were then washed with water, brine, combined, dried ($Na_2SO_4$), filtered and concentrated. Residue was stirred in dichloromethane at room temperature for 30 minutes and filtered to give crude rac-6-chloro-3-cyclohexyl-3-hydroxy-1,3-dihydro-indol-2-one as an off-white powder. (Yield 0.28 g, 43%).

EXAMPLE 19b rac-6-Chloro-3-cyclohexyl-1,3-dihydro-indol-2-one

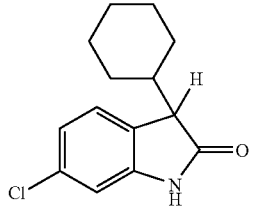

M.W. 249.74 $C_{14}H_{16}ClNO$

A suspension of rac-6-chloro-3-cyclohexyl-3-hydroxy-1, 3-dihydro-indol-2-one (0.14 g, 0.52 mmol) (from Example 19a supra) in a mixture of triethylsilane (0.25 mL, 1.58 mmol) (Aldrich) and trifluoroacetic acid (0.77 g, 7.6 mmol) (Aldrich) was heated in a 90° C. bath for 48 hours. After cooling to room temperature, mixture was diluted with ethyl acetate. Solid potassium carbonate was added and mixture stirred at room temperature for 1 hour. Mixture was filtered and concentrated. Residue was redissolved in ethyl acetate and washed with water and brine, dried ($Na_2SO_4$), filtered and concentrated. Residue was recrystallized from dichloromethane-hexanes to give rac-6-chloro-3-cyclohexyl-1,3-dihydro-indol-2-one as a grey solid. (Yield 0.11 g, 84%).

EXAMPLE 19c rac-6-Chloro-3-(3-chloro-benzyl)-3-cyclohexyl-1,3-dihydro-indol-2-one

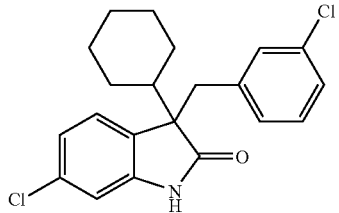

M.W. 374.314 $C_{21}H_{21}Cl_2NO$

A mixture of rac-6-chloro-3-cyclohexyl-1,3-dihydro-indol-2-one (0.11 g, 0.44 mmol) (from Example 19b supra), 3-chlorobenzyl bromide (0.11 g, 0.53 mmol) (Aldrich), potassium iodide (87 mg, 0.53 mmol) and potassium carbonate (0.13 g, 0.95 mmol) in acetone (3 mL) was heated at 60° C. for 2 days in a capped pressure tube. After cooling, mixture was diluted with ethyl acetate and extracted with water and brine. Aqueous layers were back washed with ethyl acetate. Organic layers were combined, dried ($Na_2SO_4$), filtered and concentrated. The residue was purified by chromatography (ethyl acetate-dichloromethane, 5:95, V/V) to give rac-6-chloro-3-(3-chloro-benzyl)-3-cyclohexyl-1,3-dihydro-indol-2-one as a white solid. (Yield 30 mg, 18%).

HRMS($ES^+$) m/z Calcd for $C_{21}H_{21}Cl_2NO+H$ [$(M+H)^+$]: 374.1073. Found: 374.1074.

EXAMPLE 20a rac-5-[6-Chloro-2-oxo-2,3-dihydro-1H-indol-3-yl]-3,4-dihydro-2H-pyridine-carboxylic acid tert-butyl ester

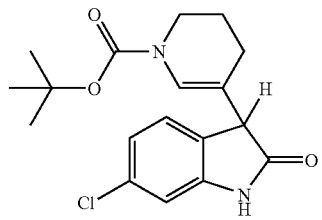

M.W. 348.83 $C_{18}H_{21}ClN_2O_3$

A suspension of 6-chlorooxindole (1.91 g, 11.4 mmol) (Cresent Chem), 1-BOC-3-piperidone (2.5 g, 12.5 mmol) (Martix Scientific), and pyrrolidine (0.1 g, 1.14 mmol) (Aldrich) in 2-propanol (30 mL) was heated at 90° C. for 2 days. The solvent was evaporated in vacuo and the residue was partitioned between ethyl acetate and water. The aqueous layer was extracted repeatedly with ethyl acetate. The organic layer was separated, combined, dried over $Na_2SO_4$ and concentrated. The residue was purified by chromatography (ethyl acetate-dichloromethane, 1:9, V/V) to give rac-5-[6-chloro-2-oxo-2,3-dihydro-1H-indol-3-yl]-3,4-dihydro-2H-pyridine-carboxylic acid tert-butyl ester as a brown solid. (Yield 2.6 g, 67%).

EXAMPLE 20b rac-5-[6-Chloro-3-(3-chloro-benzyl)-2-oxo-2,3-dihydro-1H-indol-3-yl]-3,4-dihydro-2H-pyridine-1-carboxylic acid tert-butyl ester

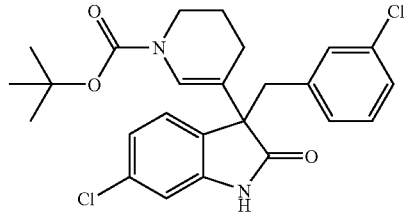

M.W. 473.404 $C_{25}H_{26}Cl_2N_2O_3$

A mixture of 5-[6-chloro-2-oxo-2,3-dihydro-1H-indol-3-yl]-3,4-dihydro-2H-pyridine-carboxylic acid tert-butyl ester (1.4 g, 4.00 mmol) (from Example 20a supra), 3-chlorobenzyl bromide (0.97 g, 4.67 mmol) (Aldrich), potassium iodide (0.79 g, 4.73 mmol) and potassium carbonate (1.2 g, 8.60 mmol) in acetone (30 mL) was heated at 60° C. for 12 hours in a capped pressure tube. After cooling, mixture was diluted with ethyl acetate and washed with water and brine. Aqueous layers were back washed with ethyl acetate. The organic layers were combined, dried over Na$_2$SO$_4$ and concentrated. The residue was purified by chromatography (ethyl acetate-dichloromethane, 1:9, V/V) to give rac-5-[6-chloro-3-(3-chloro-benzyl)-2-oxo-2,3-dihydro-1H-indol-3-yl]-3,4-dihydro-2H-pyridine-carboxylic acid tert-butyl ester as a brown solid. (Yield 1.5 g, 79%).

HRMS(ES$^+$) m/z Calcd for C$_{25}$H$_{26}$Cl$_2$N$_2$O$_3$+Na [(M+Na)$^+$]: 495.1212. Found: 495.1212.

EXAMPLE 21 rac-6-Chloro-3-(2,6-dichloro-pyridin-4-ylmethyl)-3-(3-methoxy-phenyl)-1,3-dihydro-indol-2-one

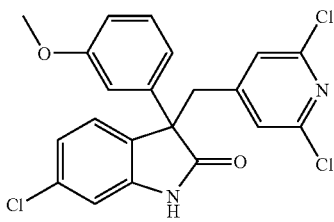

M.W. 433.725 C$_{21}$H$_{15}$Cl$_3$N$_2$O$_2$

A mixture of rac-3-(3-methoxy-phenyl)-6-chloro-1,3-dihydro-indol-2-one (82 mg, 0.3 mmol) (from Example 6b supra), 4-bromomethyl-2,6-dichloro-pyridine (85.3 mg, 0.35 mmol) (Maybridge), potassium iodide (59.2 mg, 0.35 mmol) and potassium carbonate (89.2 mg, 0.645 mmol) in acetone (3 mL) was heated at 60° C. for 3 hours in a capped pressure tube. After cooling, mixture was diluted with ethyl acetate and extracted with water and brine. Aqueous layers were back washed with ethyl acetate. Organic layers were combined, dried (Na$_2$SO$_4$), filtered and concentrated. Residue was recrystallized from dichloromethane-hexanes to give rac-6-chloro-3-(2,6-dichloro-pyridin-4-ylmethyl)-3-(3-methoxy-phenyl)-1,3-dihydro-indol-2-one as a light brown solid. (Yield 60 mg, 45%).

HRMS(ES$^+$) m/z Calcd for C$_{21}$H$_{15}$Cl$_3$N$_2$O$_2$+H [(M+H)$^+$]: 433.0272. Found: 433.0273.

EXAMPLE 22

3-[6-Chloro-3-(3-chloro-benzyl)-2-oxo-2,3-dihydro-1H-indol-3-yl]-piperidine-1-carboxylic acid tert-butyl ester

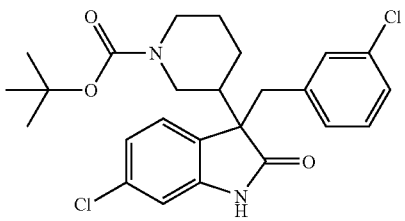

M.W. 475.420 C$_{25}$H$_{28}$Cl$_2$N$_2$O$_3$

Sodium cyanoborohydride (0.714 g, 11.4 mmol) (Aldrich) was added to a solution of rac-5-[6-chloro-3-(3-chloro-benzyl)-2-oxo-2,3-dihydro-1H-indol-3-yl]-3,4-dihydro-2H-pyridine-carboxylic acid tert-butyl ester (0.54 g, 1.14 mmol) (from Example 20b supra) in acetic acid (10 mL). The mixture was heated at 60° C. for 16 hours. After cooling, the solvent was evaporated in vacuo. To the residue was added saturated aqueous sodium bicarbonate solution, and extracted three times with ethyl acetate. The organic layers were separated, combined, dried over Na$_2$SO$_4$ and concentrated. The residue was purified by chromatography (ethyl acetate-dichloromethane, 1:9, V/V) to give rac-5-[6-chloro-3-(3-chloro-benzyl)-2-oxo-2,3-dihydro-1H-indol-3-yl]-3,4-dihydro-2H-piperidine-carboxylic acid tert-butyl ester as a white solid. (Yield 0.2 g, 37%). Further purification by recrystallization from dichloromethane-hexanes gave the product as a white solid. (Yield 0.05 g).

HRMS(ES$^+$) m/z Calcd for C$_{25}$H$_{28}$Cl$_2$N$_2$O$_3$+H [(M+H)$^+$]: 475.1550. Found: 475.1552.

EXAMPLE 23 rac-5-[6-Chloro-3-(2,6-dichloro-pyridin-4-ylmethyl)-2-oxo-2,3-dihydro-1H-indol-3-yl]-3,4-dihydro-2H-pyridine-1-carboxylic acid tert-butyl ester

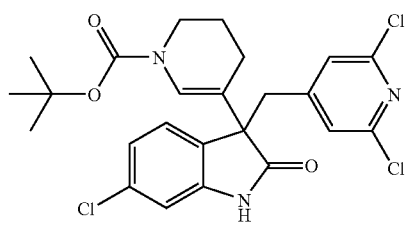

M.W. 508.836 C$_{24}$H$_{24}$Cl$_3$N$_3$O$_3$

A mixture of 5-[6-chloro-2-oxo-2,3-dihydro-1H-indol-3-yl]-3,4-dihydro-2H-pyridine-carboxylic acid tert-butyl ester (0.32 g, 0.9 mmol) (from Example 20a supra), 4-bromomethyl-2,6-dichloro-pyridine (0.26 g, 1.08 mmol) (Maybridge), potassium iodide (0.18 g, 1.08 mmol) and potassium carbonate (0.27 g, 1.97 mmol) in acetone (30 mL) was heated at 60° C. for 2 hours in a capped pressure tube. After cooling, mixture was diluted with ethyl acetate and washed with water and brine. Aqueous layers were back washed with ethyl acetate. The organic layers were combined, dried over Na$_2$SO$_4$ and concentrated. The residue was purified by chromatography (ethyl acetate-dichloromethane, 25:75, V/V) to give rac-5-[6-chloro-3-(2,6-dichloro-pyridin-4-ylmethyl)-2-oxo-2,3-dihydro-1H-indol-3-yl]-3,4-dihydro-2H-pyridine-1-carboxylic acid tert-butyl ester as a white solid. (Yield 0.28 g, 60%).

HRMS(ES$^+$) m/z Calcd for C$_{24}$H$_{24}$Cl$_3$N$_3$O$_3$+H [(M+H)$^+$]: 508.0956. Found: 508.0957.

EXAMPLE 24 rac-3-[6-Chloro-3-(2,6-dichloro-pyridin-4-ylmethyl)-2-oxo-2,3-dihydro-1H-indol-3-yl]-piperidine-1-carboxylic acid tert-butyl ester

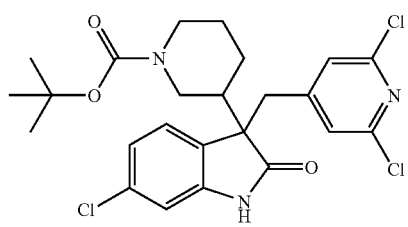

M.W. 510.852 C$_{24}$H$_{26}$Cl$_3$N$_3$O$_3$

Sodium cyanoborohydride (0.37 g, 5.89 mmol) was added to a solution of rac-5-[6-chloro-3-(2,6-dichloro-pyridin-4-ylmethyl)-2-oxo-2,3-dihydro-1H-indol-3-yl]-3,4-dihydro-2H-pyridine-1-carboxylic acid tert-butyl ester (0.3 g, 0.589 mmol) (from Example 23 supra) in acetic acid (6 mL). The mixture was heated at 60° C. for 16 hours. After cooling, the solvent was evaporated in vacuo. To the residue was added saturated aqueous sodium bicarbonate solution, and extracted three times with ethyl acetate. The organic layers were separated, combined, dried over $Na_2SO_4$ and concentrated. The residue was purified by chromatography (ethyl acetate-dichloromethane, 1:9, V/V) to give rac-5-[6-chloro-3-(2,6-dichloro-pyridin-4-ylmethyl)-2-oxo-2,3-dihydro-1H-indol-3-yl]-pyridine-1-carboxylic acid tert-butyl ester as a white solid. (Yield 0.2 g, 67%). Further purification by recrystallization from dichloromethane-hexanes gave the product as a white solid. (Yield 0.075 g).

HRMS(ES$^+$) m/z Calcd for $C_{24}H_{26}Cl_3N_3O_3$+H [(M+H)$^+$]: 510.1113. Found: 510.1117.

EXAMPLE 25a rac-6-Chloro-3-(3-chloro-benzyl)-3-piperidin-3-yl-1,3-dihydro-indol-2-one

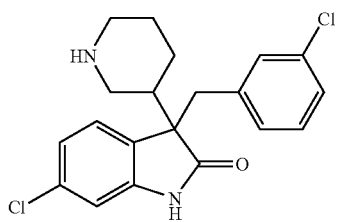

M.W. 375.301 $C_{20}H_{20}Cl_2N_2O$

This was prepared following the procedure found in Example 15a supra.

EXAMPLE 25b 3-(1-Acetyl-piperidin-3-yl)-6-chloro-3-(3-chlorobenzyl)-1,3-dihydro-indol-2-one

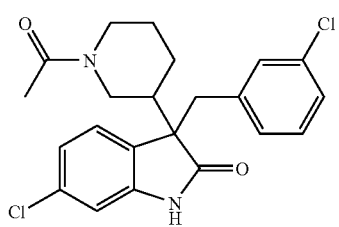

M.W. 417.339 $C_{22}H_{22}Cl_2N_2O_2$

To a solution of rac-6-chloro-3-(3-chloro-benzyl)-3-piperidin-3-yl-1,3-dihydro-indol-2-one (80 mg, 0.20 mmol) (from Example 25a supra) in tetrahydrofuran (3 mL) was added triethylamine (32 mg, 0.3 mmol) (Aldrich), followed by the addition of acetyl chloride (20 mg, 0.24 mmol) (Aldrich). The mixture was stirred at room temperature for 30 minutes. The mixture was partitioned between ethyl acetate and water. The aqueous layer was extracted with another two portions of ethyl acetate. The combined organic layers were washed with water, brine, dried over $Na_2SO_4$ and concentrated to give rac-3-(1-acetyl-piperidin-3-yl)-6-chloro-3-(3-chloro-benzyl)-1,3-dihydro-indol-2-one as a white solid. (Yield 58 mg, 66%). Further purification by precipitation from dichloromethane-hexanes gave the product as a white solid. (Yield 45 mg).

HRMS(ES$^+$) m/z Calcd for $C_{22}H_{22}Cl_2N_2O_2$+H [(M+H)$^+$]: 417.1131. Found: 417.1132.

EXAMPLE 26 rac-6-Chloro-3-(3-chloro-benzyl)-3-[1-(pyrrolidine-1-carbonyl)-piperidin-3-yl]-1,3-dihydro-indol-2-one

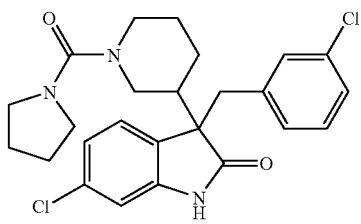

M.W. 472.419 $C_{25}H_{27}Cl_2N_3O_2$

To a solution of rac-6-chloro-3-(3-chloro-benzyl)-3-piperidin-3-yl-1,3-dihydro-indol-2-one (80 mg, 0.20 mmol) (from Example 25a supra) in tetrahydrofuran (3 mL) was added triethylamine (32 mg, 0.3 mmol) (Aldrich), followed by the addition of 1-pyrrolidinecarbonyl chloride (34 mg, 0.24 mmol) (Aldrich). The mixture was stirred at 50° C. for 1 hour, then cooled to room temperature. The mixture was partitioned between ethyl acetate and water. The aqueous layer was extracted with another two portions of ethyl acetate. The combined organic layers were washed with water, brine, dried over $Na_2SO_4$ and concentrated. The residue were triturated with dichloromethane-hexanes to give rac-6-chloro-3-(3-chloro-benzyl)-3-[1-(pyrrolidine-1-carbonyl)-piperidin-3-yl]-1,3-dihydro-indol-2-one as a white solid. (Yield 50 mg, 50%).

HRMS(ES$^+$) m/z Calcd for $C_{25}H_{27}Cl_2N_3O_2$+Na [(M+Na)$^+$]: 494.1372. Found: 494.1377.

EXAMPLE 27 rac-3-[6-Chloro-3-(3-chloro-benzyl)-2-oxo-2,3-dihydro-1H-indol-3-yl]-piperidine-1-carboxylic acid methylamide

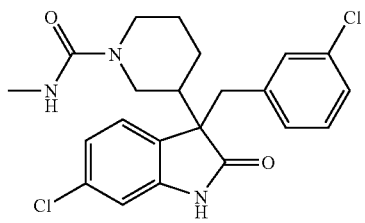

M.W. 432.354 $C_{22}H_{23}Cl_2N_3O_2$

To a solution of rac-6-chloro-3-(3-chloro-benzyl)-3-piperidin-3-yl-1,3-dihydro-indol-2-one (80 mg, 0.2 mmol) (from Example 25a supra) in dichloromethane (2 mL) was added triethylamine (32.4 mg, 0.3 mmol) (Aldrich), followed by the addition of isocyanatomethane (14.6 mg, 0.24 mmol) (Chem Service). The mixture was stirred at room temperature for 30 minutes. The mixture was then partitioned between ethyl acetate and water. The aqueous layer was extracted with another two portions of ethyl acetate. The combined organic layers were washed with water, brine, dried over Na$_2$SO$_4$ and concentrated. The residue was triturated with dichloromethane-hexanes to give rac-3-[6-chloro-3-(3-chloro-benzyl)-2-oxo-2,3-dihydro-1H-indol-3-yl]-piperidine-1-carboxylic acid methylamide as a white solid. (Yield 35 mg, 50%).

HRMS(ES$^+$) m/z Calcd for C$_{22}$H$_{23}$Cl$_2$N$_3$O$_2$+H [(M+H)$^+$]: 432.1240. Found: 432.1242.

EXAMPLE 28 rac-6-Chloro-3-(3-chloro-benzyl)-3-[1-(morpholine-4-carbonyl)-piperidin-3-yl]-1,3-dihydro-indol-2-one

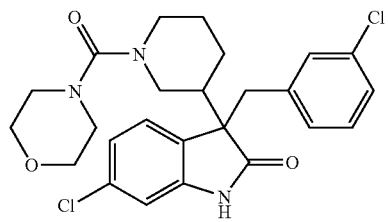

M.W. 488.418 C$_{25}$H$_{27}$Cl$_2$N$_3$O$_3$

To a solution of rac-6-chloro-3-(3-chloro-benzyl)-3-piperidin-3-yl-1,3-dihydro-indol-2-one (80 mg, 0.20 mmol) (from Example 25a supra) in tetrahydrofuran (3 mL) was added triethylamine (32 mg, 0.3 mmol), followed by the addition of morpholine-4-carbonyl chloride (38 mg, 0.24 mmol) (Aldrich). The mixture was stirred at 45° C. for 3 hours, then cooled to room temperature. The mixture was partitioned between ethyl acetate and water. The aqueous layer was extracted with another two portions of ethyl acetate. The combined organic layers were washed with water, brine, dried over Na$_2$SO$_4$ and concentrated. The residue were triturated with dichloromethane-hexanes to give rac-6-chloro-3-(3-chloro-benzyl)-3-[1-(morpholine-4-carbonyl)-piperidin-3-yl]-1,3-dihydro-indol-2-one as a white solid. (Yield 60 mg, 60%).

HRMS(ES$^+$) m/z Calcd for C$_{25}$H$_{27}$Cl$_2$N$_3$O$_3$+Na [(M+Na)$^+$]: 510.1321. Found: 510.1322.

EXAMPLE 29a rac-6-Chloro-3-(2,6-dimethoxy-pyrimidin-4-yl)-1,3-dihydro-indol-2-one

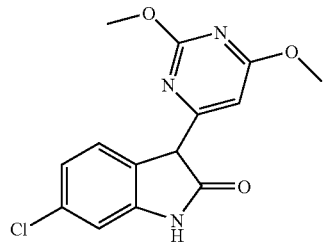

M.W. 305.72 C$_{14}$H$_{12}$ClN$_3$O$_3$

To a suspension of 6-chlorooxindole (0.94 g, 5.34 mmol) (Cresent Chem.) in N,N-dimethylformamide (20 mL) at room temperature was added lithium hydride (86 mg, 10.7 mmol) (Aldrich). The mixture was stirred at room temperature for 10 minutes, then 6-chloro-2,4-dimethoxy-pyrimidine (0.93 g, 5.34 mmol) (Aldrich) was added. The reaction mixture was heated at 110° C. for 3 hours. The mixture was cooled to room temperature. Water (100 mL) was added, and mixture was extracted with ethyl acetate (2×100 mL). The organic layers were separated, combined, washed with water, brine, dried over Na$_2$SO$_4$ and concentrated. The residue was purified by chromatography (ethyl acetate) to give rac-6-chloro-3-(2,6-dimethoxy-pyrimidin-4-yl)-1,3-dihydro-indol-2-one as a brown solid. (Yield 0.23 g, 14%).

EXAMPLE 29b rac-6-Chloro-3-(3-chloro-benzyl)-3-(2,6-dimethoxy-pyrimidin-4-yl)-1,3-dihydro-indol-2-one

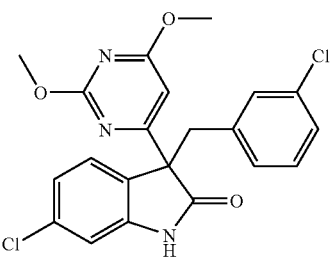

M.W. 430.294 C$_{21}$H$_{17}$Cl$_2$N$_3$O$_3$

A mixture of rac-6-chloro-3-(2,6-dimethoxy-pyrimidin-4-yl)-1,3-dihydro-indol-2-one (0.23 g, 0.75 mmol) (from Example 29a supra), 3-chlorobenzyl bromide (0.19 g, 0.9 mmol) (Aldrich), potassium iodide (0.15 g, 0.9 mmol) and potassium carbonate (0.23 g, 1.66 mmol) in acetone (20 mL) was heated at 80° C. for 30 minutes. After cooling, mixture was diluted with ethyl acetate and washed with water and brine. Aqueous layers were back washed with ethyl acetate. The organic layers were combined, dried over Na$_2$SO$_4$ and concentrated. The residue was purified by chromatography (ethyl acetate-hexanes, 1:6, V/V) to give rac-6-chloro-3-(3-chloro-benzyl)-3-(2,6-dimethoxy-pyrimidin-4-yl)-1,3-dihydro-indol-2-one as an orange solid. (Yield 0.21 g, 65%).

HRMS(ES$^+$) m/z Calcd for C$_{21}$H$_{17}$Cl$_2$N$_3$O$_3$+H [(M+H)$^+$]: 430.0720. Found: 430.0720.

EXAMPLE 30a

E/Z-6-Chloro-3-(3-chloro-benzylidene)-1,3-dihydro-indol-2-one

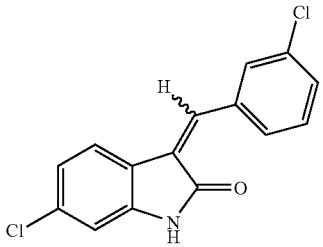

M.W. 290.15 C$_{15}$H$_9$Cl$_2$NO

To the mixture of 6-chlorooxindole (16.2 g, 92 mmol) (Crescent) and 3-chlorobenzaldehyde (12.9 g, 92 mmol) (Aldrich) in methanol (109 mL) was added pyrrolidine (6.55 g, 92 mmol) (Aldrich) dropwisely. The mixture was then heated at 70° C. for 3 hours. After cooling to 4° C., the resulting precipitate was collected and dried to give E/Z-6-chloro-3-(3-chloro-benzylidene)-1,3-dihydro-indol-2-one as a bright yellow solid. (Yield 25.2 g, 95%).

EXAMPLE 30b rac-6-Chloro-3-(3-chloro-benzyl)-1,3-dihydro-indol-2-one

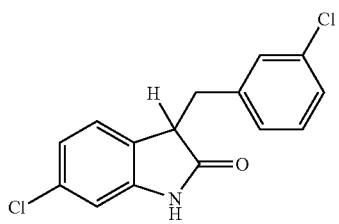

M.W. 292.17 $C_{15}H_{11}Cl_2NO$

Sodium borohydride (12.4 g, 328 mmol) (Aldrich) was added in small portions to a suspension of E/Z-6-chloro-3-(3-chloro-benzylidene)-1,3-dihydro-indol-2-one (25 g, 86 mmol) (from Example 30a supra) in methanol (400 mL) at such a rate that gas evolution was not too vigorous. When addition was complete, mixture was stirred at room temperature for 3 hours. The solvent was evaporated under reduced pressure and the residue was partitioned between ethyl acetate and water. The aqueous layer was extracted with another two portions of ethyl acetate. The combined organic layers were washed with water, brine, dried over $Na_2SO_4$ and concentrated. The residue was purified by chromatography (ethyl acetate-dichloromethane, 1:2, V/V). The resulting yellow solid was recrystallized from ethyl acetate to give rac-6-chloro-3-(3-chloro-benzyl)-1,3-dihydro-indol-2-one as a pale yellow solid. (Yield 10 g, 40%).

HRMS(ES$^+$) m/z Calcd for $C_{15}H_{11}Cl_2NO+H$ [(M+H)$^+$]: 292.0291. Found: 292.0288.

EXAMPLE 30c rac-6-Chloro-3-(3-chloro-benzyl)-3-(3-oxo-cyclohexyl)-1,3-dihydro-indol-2-one

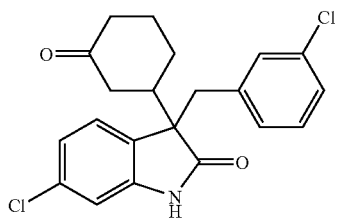

M.W. 388.297 $C_{21}H_{19}Cl_2NO_2$

A mixture of rac-6-chloro-3-(3-chloro-benzyl)-1,3-dihydro-indol-2-one (0.125 g, 0.49 mmol) (from Example 30b supra), 2-cyclohexen-1-one (0.047 g, 0.49 mmol) (Aldrich), 1,8-diazabicyclo[5.4.0]undec-7-ene (0.37 g, 2.4 mmol) (Fluka AG) in methanol (20 mL) was heated at 60° C. for 2 hours. After cooling, the mixture was concentrated, diluted with water, extracted with ethyl acetate (2×100 mL). The organic layers were separated, washed with water and brine. Aqueous layers were back washed with ethyl acetate. The organic layers were combined, dried over $Na_2SO_4$ and concentrated. The residue was purified by chromatography (ethyl acetate-hexanes, 2:3, V/V) to give rac-6-chloro-3-(3-chlorobenzyl)-3-(3-oxo-cyclohexyl)-1,3-dihydro-indol-2-one as a white solid. (Yield 0.057 g, 30%).

HRMS(ES$^+$) m/z Calcd for $C_{21}H_{19}Cl_2NO_2+Na$ [(M+Na)$^+$]: 410.0685. Found: 410.0683.

EXAMPLE 31

3-[6-Chloro-3-(3-chloro-benzyl)-2-oxo-2,3-dihydro-1H-indol-3-yl]-piperidine-1-carboxylic acid ethylamide

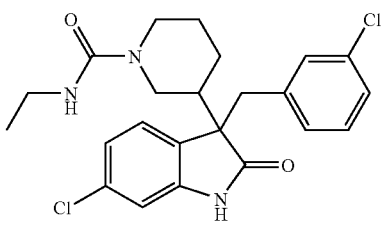

M.W. 446.381 $C_{23}H_{25}Cl_2N_3O_2$

This was prepared following the procedure found in Example 26 supra.

HRMS(ES$^+$) m/z Calcd for $C_{23}H_{25}Cl_2N_3O_2+H$ [(M+H)$^+$]: 446.1397. Found: 446.1398.

EXAMPLE 32

3-[6-Chloro-3-(3-chloro-benzyl)-2-oxo-2,3-dihydro-1H-indol-3-yl]-piperidine-1-carboxylic acid propylamide

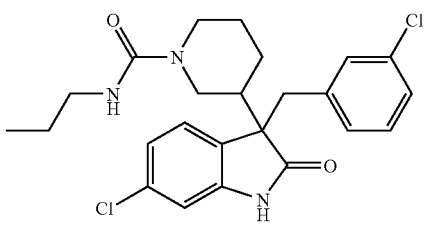

M.W. 460.408 $C_{24}H_{27}Cl_2N_3O_2$

This was prepared following the procedure found in Example 26 supra.

HRMS(ES$^+$) m/z Calcd for $C_{24}H_{27}Cl_2N_3O_2+H$ [(M+H)$^+$]: 460.1553. Found: 460.1554.

EXAMPLE 33

3-[6-Chloro-3-(3-chloro-benzyl)-2-oxo-2,3-dihydro-1H-indol-3-yl]-piperidine-1-carboxylic acid tert-butylamide

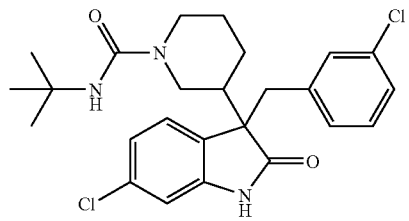

M.W. 474.435 $C_{25}H_{29}Cl_2N_3O_2$

This was prepared following the procedure found in Example 26 supra.
HRMS(ES$^+$) m/z Calcd for $C_{25}H_{29}Cl_2N_3O_2$+H [(M+H)$^+$]: 474.1710. Found: 474.1713.

EXAMPLE 34

3-[6-Chloro-3-(3-chloro-benzyl)-2-oxo-2,3-dihydro-1H-indol-3-yl]-piperidine-1-carboxylic acid (2-chloro-ethyl)-amide

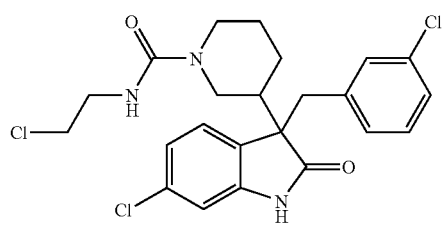

M.W. 480.826 $C_{23}H_{24}Cl_3N_3O_2$

This was prepared following the procedure found in Example 26 supra.
HRMS(ES$^+$) m/z Calcd for $C_{23}H_{24}Cl_3N_3O_2$+H [(M+H)$^+$]: 480.1007. Found: 480.1009.

EXAMPLE 35

3-[6-Chloro-3-(3-chloro-benzyl)-2-oxo-2,3-dihydro-1H-indol-3-yl]-piperidine-1-carboxylic acid phenylamide

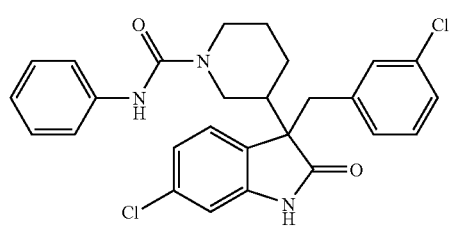

M.W. 494.425 $C_{27}H_{25}Cl_2N_3O_2$

This was prepared following the procedure found in Example 26 supra.
HRMS(ES$^+$) m/z Calcd for $C_{27}H_{25}Cl_2N_3O_2$+H [(M+H)$^+$]: 494.1397. Found: 494.1398.

EXAMPLE 36

3-[6-Chloro-3-(3-chloro-benzyl)-2-oxo-2,3-dihydro-1H-indol-3-yl]-piperidine-1-carboxylic acid isopropylamide

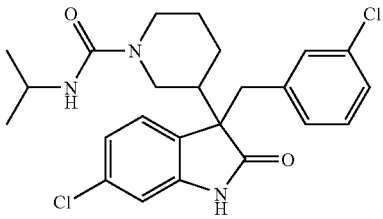

M.W. 460.408 $C_{24}H_{27}Cl_2N_3O_2$

This was prepared following the procedure found in Example 26 supra.
HRMS(ES$^+$) m/z Calcd for $C_{24}H_{27}Cl_2N_3O_2$+H [(M+H)$^+$]: 460.1553. Found: 460.1552.

EXAMPLE 37 rac-6-Chloro-3-(3-chloro-4-fluoro-benzyl)-3-(3-methoxy-phenyl)-1,3-dihydro-indol-2-one

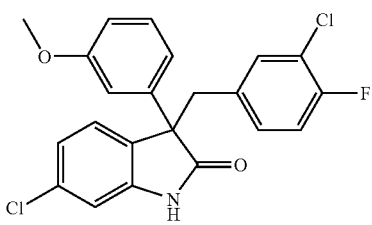

M.W. 416.283 $C_{22}H_{16}Cl_2FNO_2$

This was prepared following the procedure found in Example 6c supra.
HRMS(ES$^+$) m/z Calcd for $C_{22}H_{16}Cl_2FNO_2$+H [(M+H)$^+$]: 416.0615. Found: 416.0617.

EXAMPLE 38

3-[6-Chloro-3-(3-chloro-benzyl)-2-oxo-2,3-dihydro-1H-indol-3-yl]-piperidine-1-carboxylic acid cyclohexylamide

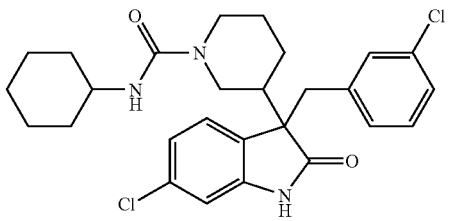

M.W. 500.473 $C_{27}H_{31}Cl_2N_3O_2$

This was prepared following the procedure found in Example 26 supra.
HRMS(ES$^+$) m/z Calcd for $C_{27}H_{31}Cl_2N_3O_2$+H [(M+H)$^+$]: 500.1866. Found: 500.1863.

EXAMPLE 39a rac-6-Chloro-3-hydroxy-3-pyridin-3-yl-1,3-dihydro-indol-2-one

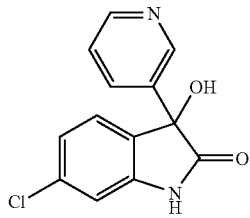

M.W. 260.68 $C_{13}H_9ClN_2O_2$

To a solution of n-butyllithium (2.0 M in hexanes, 3.45 mL, 7.5 mmol) (Aldrich) in tetrahydrofuran (3 mL) at −78° C. was added a solution of 3-bromo-pyridine (0.96 g, 8.1 mmol) (Aldrich) in tetrahydrofuran (6 mL) dropwisely. After the addition, the resulting dark solution was stirred for additional 15 minutes. A solution of 6-chloroisatin (0.5 g, 2.76 mmol) (Crescent) in tetrahydrofuran (5 mL) was added dropwisely and the crude was warmed up to room temperature and stirred at room temperature for 3 hours. The reaction was quenched with water. The mixture was extracted with ethyl acetate three times. The combined organic layers were washed with water, brine, dried over $Na_2SO_4$ and concentrated. The residue was purified by chromatography to give rac-6-Chloro-3-hydroxy-3-pyridin-3-yl-1,3-dihydro-indol-2-one as a yellow solid. (Yield 0.27 g, 37%).

EXAMPLE 39b rac-6-Chloro-3-pyridin-3-yl-1,3-dihydro-indol-2-one

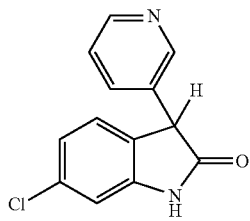

M.W. 244.68 $C_{13}H_9ClN_2O$ rac-6-Chloro-3-hydroxy-3-pyridin-3-yl-1,3-dihydro-indol-2-one (0.27 g, 1.0 mmol) (from Example 39a supra) was suspended in a mixture of triethylsilane (0.49 mL, 3.0 mmol) (Aldrich) and trifluoroacetic acid (1.77 g, 15.0 mmol) (Aldrich) and heated in an 78° C. oil bath for overweekend. After cooling to room temperature, the mixture was diluted with ethyl acetate and treated with solid sodium carbonate (1.0 g). After stirring for 30 minutes, mixture was extracted with water and brine. Aqueous layers were back washed with ethyl acetate. Organic layers were combined, dried ($Na_2SO_4$), filtered and concentrated to obtain rac-6-chloro-3-pyridin-3-yl-1,3-dihydro-indol-2-one (Yield 0.1 g, 40%) as yellow oil and carried out for the next step without further purification.

EXAMPLE 39c rac-6-Chloro-3-(3-chloro-benzyl)-3-pyridin-3-yl-1,3-dihydro-indol-2-one

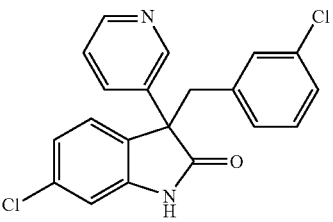

M.W. 369.25 $C_{20}H_{14}Cl_2N_2O$

A mixture of rac-6-chloro-3-pyridin-3-yl-1,3-dihydro-indol-2-one (0.081 g, 0.33 mmol) (from Example 39b supra), 3-chlorobenzyl bromide (0.080 g, 0.39 mmol) (Aldrich), potassium iodide (0.065 g, 0.39 mmol) and potassium carbonate (0.098 g, 0.72 mmol) in acetone (3 mL) was heated at 67° C. for 2 hours in a capped pressure tube. After cooling, the mixture was diluted with ethyl acetate and extracted with water and brine. Aqueous layers were back washed with ethyl acetate. Organic layers were combined, dried ($Na_2SO_4$), filtered and concentrated. The residue was purified by chromatography to give rac-6-chloro-3-(3-chloro-benzyl)-3-pyridin-3-yl-1,3-dihydro-indol-2-one as an off-white solid. (Yield, 0.05 g, 42%).

HRMS($ES^+$) m/z Calcd for $C_{20}H_{14}Cl_2N_2O+H$ $[(M+H)^+]$: 369.0556. Found: 369.0556.

EXAMPLE 40a rac-6-Chloro-3-(3,5-dimethoxy-phenyl)-3-hydroxy-1,3-dihydro-indol-2-one

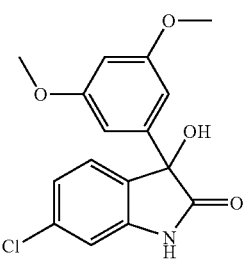

M.W. 319.75 $C_{16}H_{14}ClNO_4$

A solution of 3,5-dimethoxyphenyl magnesium bromide in tetrahydrofuran (1.0 M, 6.9 mmol) (Aldrich) was added dropwise with magnetic stirring to a suspension of 6-chloroisatin (0.5 g, 2.76 mmol) in tetrahydrofuran (14 mL) under argon with cooling in a −25° C. bath at such a rate that reaction temperature was kept below −10° C. Cooling bath was then removed and mixture was allowed to warm to room temperature. After stirring for an additional 2 hours, 15% aqueous ammonium chloride solution and water were added and mixture extracted with ethyl acetate. Ethyl acetate layers were then washed with water, brine, combined, dried (Na₂SO₄), filtered and concentrated. Residue was stirred in dichloromethane at room temperature for 15 minutes and filtered to give crude rac-6-chloro-3-(3,5-dimethoxy-phenyl)-3-hydroxy-1,3-dihydro-indol-2-one as an off-white powder. This was used in the next step without further purification.

EXAMPLE 40b rac-6-Chloro-3-(3,5-dimethoxy-phenyl)-1,3-dihydro-indol-2-one

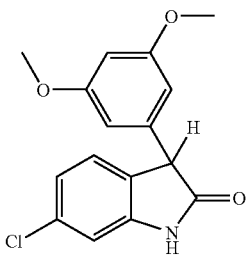

M.W. 303.75 C₁₆H₁₄ClNO₃

Crude rac-6-chloro-3-(3,5-dimethoxy-phenyl)-3-hydroxy-1,3-dihydro-indol-2-one (0.3 g, 0.94 mmol) (from Example 40a supra) was suspended in a mixture of triethylsilane (0.45 mL, 2.82 mmol) (Aldrich) and trifluoroacetic acid (1.38 g, 14.1 mmol) and heated in an 90° C. oil bath for 17 hours. After cooling to room temperature, mixture was diluted with ethyl acetate and treated with solid sodium carbonate (1 g). After stirring for 30 minutes, mixture was extracted with water and brine. Aqueous layers were back washed with ethyl acetate. Organic layers were combined, dried (Na₂SO₄), filtered and concentrated. Residue was recrystallized from dichloromethane-hexanes to give rac-6-chloro-3-(3,5-dimethoxy-phenyl)-1,3-dihydro-indol-2-one as yellow solid. (Yield 0.2 g, 71%)

EXAMPLE 40c rac-6-Chloro-3-(3-chloro-benzyl)-3-(3,5-dimethoxy-phenyl)-1,3-dihydro-indol-2-one

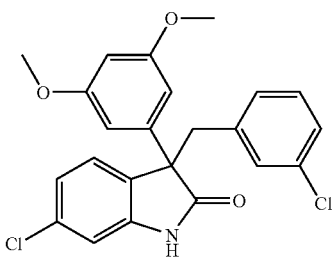

M.W. 428.32 C₂₃H₁₉Cl₂NO₃

A mixture of rac-6-chloro-3-(3,5-dimethoxy-phenyl)-1,3-dihydro-indol-2-one (0.1 g, 0.33 mmol) (from Example 40b supra), 3-chlorobenzyl bromide (0.080 g, 0.38 mmol) (Aldrich), potassium iodide (0.065 g, 0.38 mmol) and potassium carbonate (0.098 g, 0.71 mmol) in acetone (5 mL) was heated at 60° C. for 2 hours. After cooling, mixture was partitioned between ethyl acetate and water. The aqueous layer was extracted with ethyl acetate. The combined organic layer was washed with water and brine, dried (Na₂SO₄), filtered and concentrated. Residue was purified by chromatography to give rac-6-chloro-3-(3-chloro-benzyl)-3-(3,5-dimethoxy-phenyl)-1,3-dihydro-indol-2-one as a white solid. (Yield 0.1 g, 71.4%).

HRMS(ES⁺) m/z Calcd for C₂₃H₁₉Cl₂NO₃+H [(M+H)⁺]: 428.0815. Found: 428.0813.

EXAMPLE 41 rac-3-[6-Chloro-3-(3-chloro-benzyl)-2-oxo-2,3-dihydro-1H-indol-3-yl]-piperidine-1-carboxylic acid (3-methoxy-phenyl)-amide

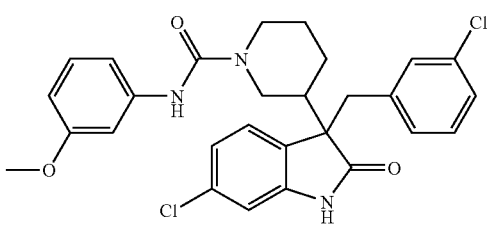

M.W. 524.45 C₂₈H₂₇Cl₂N₃O₃

To a solution of rac-6-chloro-3-(3-chloro-benzyl)-3-piperidin-3-yl-1,3-dihydro-indol-2-one (50 mg, 0.13 mmol) (from Example 25a supra) in dichloromethane (3 mL) was added triethylamine (20 mg, 0.19 mmol) (Aldrich), followed by the addition of 3-methoxyphenyl isocyanate (24 mg, 0.16 mmol) (Aldrich). The mixture was stirred at room temperature for 30 minutes. The mixture was partitioned between dichlormethane and water. The aqueous layer was extracted with dichlormethane. The combined organic layers were washed with water, brine, dried over Na₂SO₄ and concentrated. The residue was purified by chromatography to give rac-3-[6-chloro-3-(3-chloro-benzyl)-2-oxo-2,3-dihydro-1H-indol-3-yl]-piperidine-1-carboxylic acid (3-methoxy-phenyl)-amide as a white solid. (Yield 45 mg, 64%).

HRMS(ES⁺) m/z Calcd for C₂₈H₂₇Cl₂N₃O₃+H [(M+H)⁺]: 524.1502. Found: 524.1503.

EXAMPLE 42 rac-3-[6-Chloro-3-(3-chloro-benzyl)-2-oxo-2,3-dihydro-1H-indol-3-yl]-piperidine-1-carboxylic acid (4-methoxy-phenyl)-amide

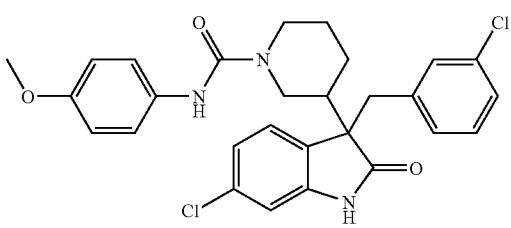

M.W. 524.45 C₂₈H₂₇Cl₂N₃O₃

To a solution of rac-6-chloro-3-(3-chloro-benzyl)-3-piperidin-3-yl-1,3-dihydro-indol-2-one (50 mg, 0.13 mmol) (from Example 25a supra) in dichloromethane (3 mL) was added triethylamine (20 mg, 0.19 mmol) (Aldrich), followed by the addition of 4-methoxyphenyl isocyanate (24 mg, 0.16 mmol) (Aldrich). The mixture was stirred at room temperature for 30 mins. The mixture was partitioned between dichlormethane and water. The aqueous layer was extracted with dichlormethane. The combined organic layers were washed with water, brine, dried over Na$_2$SO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-methoxy-phenyl)-amide as a white solid. (Yield 35 mg, 50%).

HRMS(ES$^+$) m/z Calcd for C$_{28}$H$_{27}$Cl$_2$N$_3$O$_3$+H [(M+H)$^+$]: 524.1502. Found: 524.1503.

EXAMPLE 43 rac-3-[6-Chloro-3-(3-chloro-benzyl)-2-oxo-2,3-dihydro-1H-indol-3-yl]-piperidine-1-carboxylic acid (2-methoxy-phenyl)-amide

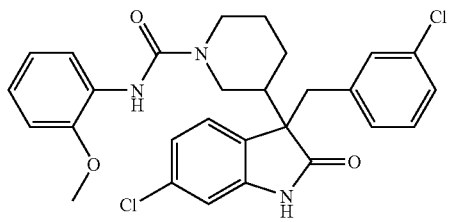

M.W. 524.45 C$_{28}$H$_{27}$Cl$_2$N$_3$O$_3$

To a solution of rac-6-chloro-3-(3-chloro-benzyl)-3-piperidin-3-yl-1,3-dihydro-indol-2-one (50 mg, 0.13 mmol) (from Example 25a supra) in dichloromethane (3 mL) was added triethylamine (20 mg, 0.19 mmol) (Aldrich), followed by the addition of 2-methoxyphenyl isocyanate (24 mg, 0.16 mmol) (Aldrich). The mixture was stirred at room temperature for 30 mins. The mixture was partitioned between dichlormethane and water. The aqueous layer was extracted with dichlormethane. The combined organic layers were washed with water, brine, dried over Na$_2$SO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (2-methoxy-phenyl)-amide as a white solid. (Yield 45 mg, 64%).

HRMS(ES$^+$) m/z Calcd for C$_{28}$H$_{27}$Cl$_2$N$_3$O$_3$+H [(M+H)$^+$]: 524.1502. Found: 524.1503.

EXAMPLE 44 rac-3-[6-Chloro-3-(3-chloro-benzyl)-2-oxo-2,3-dihydro-1H-indol-3-yl]-piperidine-1-carboxylic acid (4-chloro-phenyl)-amide

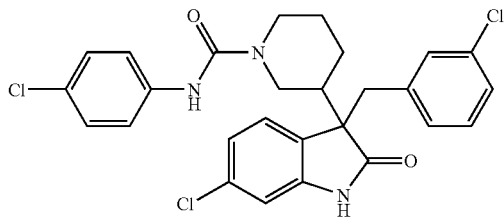

M.W. 528.86 C$_{27}$H$_{24}$Cl$_3$N$_3$O$_2$

To a solution of rac-6-chloro-3-(3-chloro-benzyl)-3-piperidin-3-yl-1,3-dihydro-indol-2-one (50 mg, 0.13 mmol) (from Example 25a supra) in dichloromethane (3 mL) was added triethylamine (20 mg, 0.19 mmol) (Aldrich), followed by the addition of 4-chloro-phenyl isocyanate (24 mg, 0.16 mmol) (Aldrich). The mixture was stirred at room temperature for 30 mins. The mixture was partitioned between dichlormethane and water. The aqueous layer was extracted with dichlormethane. The combined organic layers were washed with water, brine, dried over Na$_2$SO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-chloro-phenyl)-amide as a white solid. (Yield 42 mg, 60%).

HRMS(ES$^+$) m/z Calcd for C$_{27}$H$_{24}$Cl$_3$N$_3$O$_2$+H [(M+H)$^+$]: 528.1007. Found: 528.1008.

EXAMPLE 45 rac-3-[6-Chloro-3-(3-chloro-benzyl)-2-oxo-2,3-dihydro-1H-indol-3-yl]-piperidine-1-carboxylic acid (3-chloro-phenyl)-amide

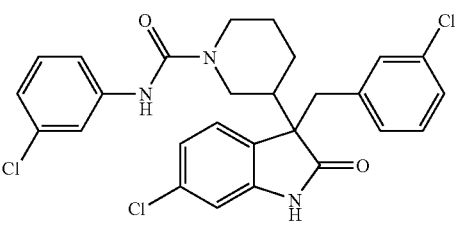

M.W. 528.86 C$_{27}$H$_{24}$Cl$_3$N$_3$O$_2$

To a solution of rac-6-chloro-3-(3-chloro-benzyl)-3-piperidin-3-yl-1,3-dihydro-indol-2-one (50 mg, 0.13 mmol) (from Example 25a supra) in dichloromethane (3 mL) was added triethylamine (20 mg, 0.19 mmol) (Aldrich), followed by the addition of 3-chloro-phenyl isocyanate (24 mg, 0.16 mmol) (Aldrich). The mixture was stirred at room temperature for 30 minutes. The mixture was partitioned between dichlormethane and water. The aqueous layer was extracted with dichlormethane. The combined organic layers were washed with water, brine, dried over Na$_2$SO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (3-chloro-phenyl)-amide as a white solid. (Yield 32 mg, 46%).

HRMS(ES$^+$) m/z Calcd for C$_{27}$H$_{24}$Cl$_3$N$_3$O$_2$+Na [(M+Na)$^+$]: 550.0826. Found: 550.0832.

EXAMPLE 46 rac-3-[6-Chloro-3-(3-chloro-benzyl)-2-oxo-2,3-dihydro-1H-indol-3-yl]-piperidine-1-carboxylic acid pyridine-3-yl-amide

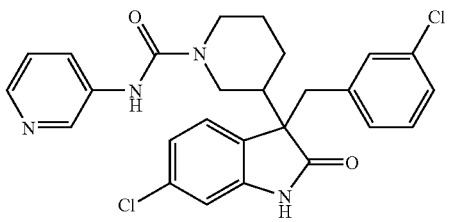

M.W. 495.41 C$_{26}$H$_{24}$Cl$_2$N$_4$O$_2$

To a solution of rac-6-chloro-3-(3-chloro-benzyl)-3-piperidin-3-yl-1,3-dihydro-indol-2-one (50 mg, 0.13 mmol) (from Example 25a supra) in dichloromethane (3 mL) was added triethylamine (20 mg, 0.19 mmol) (Aldrich), followed by the addition of 3-isocyanato-pyridine (19 mg, 0.16 mmol) (Oakwood). The mixture was stirred at room temperature for 30 minutes. The mixture was partitioned between dichlormethane and water. The aqueous layer was extracted with dichlormethane. The combined organic layers were washed with water, brine, dried over $Na_2SO_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid pyridine-3-yl-amide as a white solid. (Yield 30 mg, 45%).

HRMS(ES$^+$) m/z Calcd for $C_{26}H_{24}Cl_2N_4O_2$+H [(M+H)$^+$]: 495.1349. Found: 495.1348.

EXAMPLE 47a rac-6-Chloro-3-hydroxy-3-naphthalen-2-yl-1,3-dihydro-indol-2-one

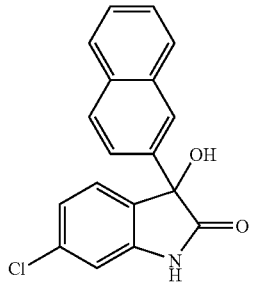

M.W. 309.75 $C_{18}H_{12}ClNO_2$

A solution of 2-naphthylmagnesium bromide in tetrahydrofuran (0.5 M, 8.26 mL, 4.13 mmol) (Aldrich) was added dropwise with magnetic stirring to a suspension of 6-chloroisatin (0.3 g, 1.67 mmol) in tetrahydrofuran (10 mL) with cooling in a –25° C. bath at such a rate that reaction temperature was kept below –10° C. Cooling bath was then removed and mixture was allowed to warm to room temperature. After stirring for an additional 4 hours, 15% aqueous ammonium chloride solution was added and mixture extracted with ethyl acetate. The combined organic layers were then washed with water, brine, combined, dried ($Na_2SO_4$), filtered and concentrated. Residue was stirred in dichloromethane at room temperature for 15 minutes and filtered to give crude rac-6-chloro-3-hydroxy-3-naphthalen-2-yl-1,3-dihydro-indol-2-one as a red solid. This was used in the next step without further purification.

EXAMPLE 47b rac-6-Chloro-3-naphthalen-2-yl-1,3-dihydro-indol-2-one

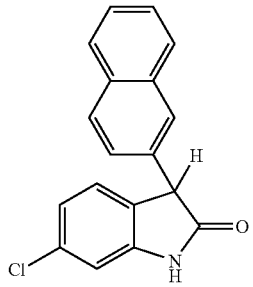

M.W. 293.76 $C_{18}H_{12}ClNO$

Crude rac-6-chloro-3-hydroxy-3-naphthalen-2-yl-1,3-dihydro-indol-2-one (0.15 g, 0.48 mmol) (from Example 47a supra) was suspended in a mixture of triethylsilane (0.23 mL, 1.44 mmol) (Aldrich) and trifluoroacetic acid (0.83 g, 7.2 mmol) and heated in an 90° C. oil bath for 17 hours. After cooling to room temperature, mixture was diluted with ethyl acetate and treated with solid sodium carbonate (1 g). After stirring for 30 minutes, mixture was extracted with water and brine. Aqueous layers were back washed with ethyl acetate. Organic layers were combined, dried (MgSO$_4$), filtered and concentrated. Residue was recrystallized from dichloromethane-hexanes to give rac-6-chloro-3-naphthalen-2-yl-1,3-dihydro-indol-2-one as brown solid. (Yield 0.08 g, 56%)

EXAMPLE 47c rac-6-Chloro-3-(3-chloro-benzyl)-3-naphthalen-2-yl-1,3-dihydro-indol-2-one

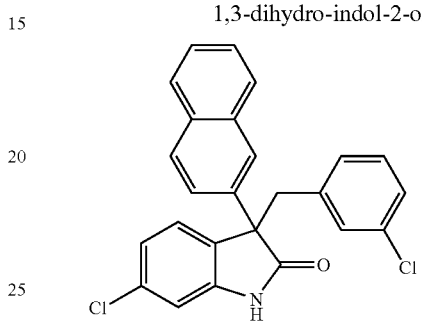

M.W. 418.33 $C_{25}H_{17}Cl_2NO$

A mixture of rac-6-chloro-3-naphthalen-2-yl-1,3-dihydro-indol-2-one (0.07 g, 0.24 mmol) (from Example 47b supra), 3-chlorobenzyl bromide (0.053 g, 0.28 mmol) (Aldrich), potassium iodide (0.047 g, 0.28 mmol) and potassium carbonate (0.071 g, 0.52 mmol) in acetone (3 mL) was heated at 65° C. for 2 hours. After cooling, mixture was partitioned between ethyl acetate and water. The aqueous layer was extracted with ethyl acetate three times. The combined organic layer was washed with water and brine, dried ($Na_2SO_4$), filtered and concentrated. Residue was purified by chromatography to give rac-6-chloro-3-(3-chloro-benzyl)-3-naphthalen-2-yl-1,3-dihydro-indol-2-one as a brown solid. (Yield 0.02 g, 20.2%).

HRMS(ES$^+$) m/z Calcd for $C_{25}H_{17}Cl_2NO$+H [(M+H)$^+$]: 418.0760. Found: 418.0762.

EXAMPLE 48a 4-(2-Morpholin-4-yl-2-oxo-ethyl)-piperazine-1-carbonyl chloride

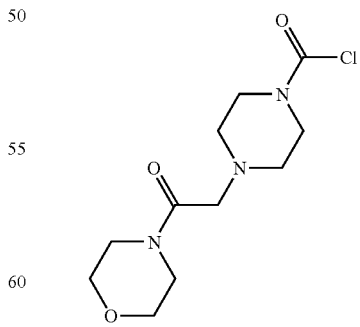

M.W. 275.74 $C_{11}H_{18}ClN_3O_3$

To the solution of 1-morpholin-4-yl-2-piperazin-1-yl-ethanone (0.5 g, 2.34 mmol) (Oakwood) in dichloromethane (15 mL) was added saturated sodium bicarbonate solution (15 mL). The reaction mixture was cooled to 0° C. and then followed by the dropwise addition of phosgene (20% in toluene, 2.22 mL, 4.21 mmol). The reaction mixture was allowed to warm up to room temperature. After stirring at room temperature for 30 minutes, the reaction mixture was extracted with dichloromethane three times. The combined organic layer was washed with water and brine, dried (Na$_2$SO$_4$), filtered and concentrated to give crude 4-(2-morpholin-4-yl-2-oxo-ethyl)-piperazine-1-carbonyl chloride as yellow oil and used for the next step without further purification.

EXAMPLE 48b rac-6-Chloro-3-(3-chloro-benzyl)-3-{1-[4-(2-Morpholin-4-yl-2-oxo-ethyl)-piperazine-1-carbonyl]-piperidine-3-yl}-1,3-dihydro-indol-2-one

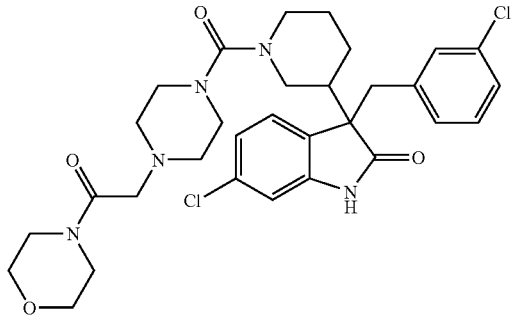

M.W. 614.58 C$_{31}$H$_{37}$Cl$_2$N$_5$O$_4$

To a solution of rac-6-chloro-3-(3-chloro-benzyl)-3-piperidin-3-yl-1,3-dihydro-indol-2-one (90 mg, 0.24 mmol) (from Example 25a supra) in tetrahydrofuron (3 mL) was added triethyl amine (60 mg, 0.60 mmol) (Aldrich), followed by the addition of 4-(2-morpholin-4-yl-2-oxo-ethyl)-piperazine-1-carbonyl chloride (99 mg, 0.36 mmol) (from Example 48a supra). The mixture was stirred at room temperature for 30 minutes. The mixture was partitioned between ethyl acetate and water. The aqueous layer was extracted with ethyl acetate. The combined organic layer was washed with water, brine, dried over Na$_2$SO$_4$ and concentrated. The residue was purified by chromatography to give rac-6-chloro-3-(3-chloro-benzyl)-3-{1-[4-(2-morpholin-4-yl-2-oxo-ethyl)-piperazine-1-carbonyl]-piperidine-3-yl}-1,3-dihydro-indol-2-one as a white solid. (Yield 70 mg, 47.6%).

HRMS(ES$^+$) m/z Calcd for C$_{31}$H$_{37}$Cl$_2$N$_5$O$_4$+H [(M+H)$^+$]: 614.2296. Found: 614.2295.

EXAMPLE 49 rac-3-(1-Butyl-piperidin-4-yl)-6-Chloro-3-(3-chloro-benzyl)-1,3-dihydro-indol-2-one

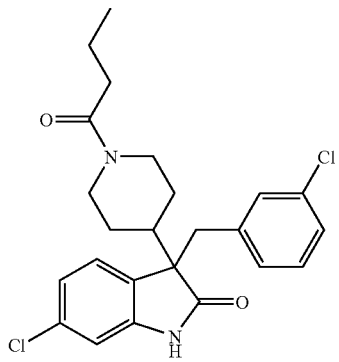

M.W. 460.402 C$_{24}$H$_{27}$Cl$_2$N$_3$O$_2$

To a solution of rac-6-chloro-3-(3-chloro-benzyl)-3-piperidin-4-yl-1,3-dihydro-indol-2-one (71 mg, 0.19 mmol) (from Example 15a supra) in dichloromethane (3 mL) was added triethylamine (28 mg, 0.29 mmol) (Aldrich), followed by the addition of 1-isocyanto-propane (19 mg, 0.23 mmol) (Aldrich). The mixture was stirred at room temperature for 30 minutes. The mixture was partitioned between dichlormethane and water. The aqueous layer was extracted with dichlormethane. The combined organic layers were washed with water, brine, dried over Na$_2$SO$_4$ and concentrated. The residue was purified by chromatography to give rac-3-(1-butyl-piperidin-4-yl)-6-Chloro-3-(3-chloro-benzyl)-1,3-dihydro-indol-2-one as a white solid. (Yield 35 mg, 40%).

HRMS(ES$^+$) m/z Calcd for C$_{24}$H$_{27}$Cl$_2$N$_3$O$_2$+H [(M+H)$^+$]: 460.1553. Found: 460.1555.

EXAMPLE 50 rac-6-Chloro-3-(3-chloro-benzyl)-3-{1-[4-(2-Morpholin-4-yl-2-oxo-ethyl)-piperazine-1-carbonyl]-piperidine-4-yl}-1,3-dihydro-indol-2-one

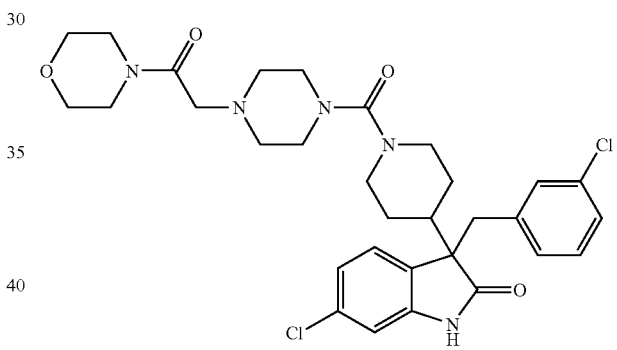

M.W. 614.58 C$_{31}$H$_{37}$Cl$_2$N$_5$O$_4$

To a solution of rac-6-chloro-3-(3-chloro-benzyl)-3-piperidin-3-yl-1,3-dihydro-indol-2-one (0.15 g, 0.4 mmol) (from Example 15a supra) in tetrahydrofuron (3 mL) was added triethyl amine (0.14 g, 1 mmol) (Aldrich), followed by the addition of 4-(2-morpholin-4-yl-2-oxo-ethyl)-piperazine-1-carbonyl chloride (0.17 g, 0.6 mmol) (from Example 48a supra). The mixture was stirred at room temperature for 30 minutes. The mixture was partitioned between ethyl acetate and water. The aqueous layer was extracted with ethyl acetate. The combined organic layer was washed with water, brine, dried over Na$_2$SO$_4$ and concentrated. The residue was purified by chromatography to give rac-6-chloro-3-(3-chloro-benzyl)-3-{1-[4-(2-Morpholin-4-yl-2-oxo-ethyl)-piperazine-1-carbonyl]-piperidine-4-yl}-1,3-dihydro-indol-2-one as a white solid. (Yield 0.12 g, 50.8%).

HRMS(ES$^+$) m/z Calcd for C$_{31}$H$_{37}$Cl$_2$N$_5$O$_4$+H [(M+H)$^+$]: 614.2296. Found: 614.2296.

EXAMPLE 51 rac-3-[6-Chloro-3-(3-chloro-benzyl)-2-oxo-2,3-dihydro-1H-indol-3-yl]-piperidine-1-carboxylic acid (3,4,5-trimethoxy-phenyl)-amide

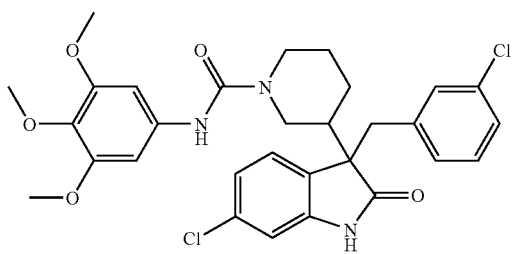

M.W. 584.497 C$_{30}$H$_{31}$Cl$_2$N$_3$O$_5$

To a solution of rac-6-chloro-3-(3-chloro-benzyl)-3-piperidin-3-yl-1,3-dihydro-indol-2-one (50 mg, 0.13 mmol) (from Example 25a supra) in dichloromethane (3 mL) was added triethylamine (20 mg, 0.20 mmol) (Aldrich), followed by the addition of 5-isocyanato-1,2,3-trimethoxy-benzene (33 mg, 0.16 mmol) (Aldrich). The mixture was stirred at room temperature for 30 minutes. The mixture was partitioned between dichlormethane and water. The aqueous layer was extracted with dichlormethane. The combined organic layers were washed with water, brine, dried over Na$_2$SO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (3,4,5-trimethoxy-phenyl)-amide (Yield 35 mg, 44.9%).

HRMS(ES$^+$) m/z Calcd for C$_{30}$H$_{31}$Cl$_2$N$_3$O$_5$+H [(M+H)$^+$]: 584.1714. Found: 584.1717.

EXAMPLE 52a rac-6-Chloro-3-(3,4-dimethyl-phenyl)-3-hydroxy-1,3-dihydro-indol-2-one

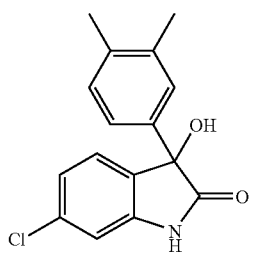

M.W. 287.75 C$_{16}$H$_{14}$ClNO$_2$

A solution of 3,4-dimethylphenyl magnesium bromide in tetrahydrofuran (0.5 M, 3.3 mL, 1.65 mmol) (Aldrich) was added dropwise with magnetic stirring to a suspension of 6-chloroisatin (0.2 g, 1.1 mmol) in tetrahydrofuran (5 mL) with cooling in a −25° C. bath. Cooling bath was then removed and mixture was allowed to warm to room temperature. After stirring for an additional 3 hours, 15% aqueous ammonium chloride solution was added and mixture extracted with ethyl acetate. The combined organic layers were then washed with water, brine, combined, dried (Na$_2$SO$_4$), filtered and concentrated. Residue was stirred in dichloromethane at room temperature for 15 minutes and filtered to give crude rac-6-chloro-3-(3,4-dimethyl-phenyl)-3-hydroxy-1,3-dihydro-indol-2-one as a yellow solid. This was used in the next step without further purification.

EXAMPLE 52b rac-6-Chloro-3-(3,4-dimethyl-phenyl)-1,3-dihydro-indol-2-one

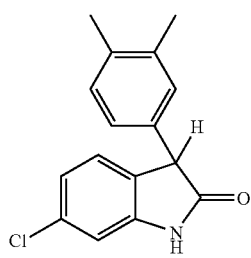

M.W. 271.75 C$_{16}$H$_{14}$ClNO

Crude rac-6-chloro-3-(3,4-dimethyl-phenyl)-3-hydroxy-1,3-dihydro-indol-2-one (0.25 g, 0.87 mmol) (from Example 52a supra) was suspended in a mixture of triethylsilane (0.41 mL, 2.61 mmol) (Aldrich) and trifluoroacetic acid (1.48 g, 13.1 mmol) and heated in an 80° C. oil bath for 17 hours. After cooling to room temperature, mixture was diluted with ethyl acetate and treated with solid sodium carbonate (1 g). After stirring for 30 minutes, mixture was extracted with water and brine. Aqueous layers were back washed with ethyl acetate. Organic layers were combined, dried (Na$_2$SO$_4$), filtered and concentrated. Residue was recrystallized from dichloromethane-hexanes to give rac-6-chloro-3-(3,4-dimethyl-phenyl)-1,3-dihydro-indol-2-one as a brown solid. (Yield 0.18 g, 78%)

EXAMPLE 52c rac-6-Chloro-3-(3-chloro-benzyl)-3-(3,4-dimethyl-phenyl)-1,3-dihydro-indol-2-one

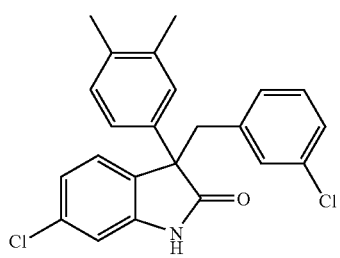

M.W. 396.32 C$_{23}$H$_{19}$Cl$_2$NO

A mixture of rac-6-chloro-3-(3,4-dimethyl-phenyl)-1,3-dihydro-indol-2-one (0.18 g, 0.66 mmol) (from Example 52b supra), 3-chlorobenzyl bromide (0.16 g, 0.77 mmol) (Aldrich), potassium iodide (0.13 g, 0.78 mmol) and potassium carbonate (0.197 g, 1.42 mmol) in acetone (5 mL) was heated at 70° C. for 4 hours. After cooling, mixture was partitioned between ethyl acetate and water. The aqueous layer was extracted with ethyl acetate three times. The combined organic layer was washed with water and brine, dried (Na$_2$SO$_4$), filtered and concentrated. Residue was purified by chromatography to give rac-6-chloro-3-(3-chloro-benzyl)-3-(3,4-dimethyl-phenyl)-1,3-dihydro-indol-2-one as yellow solid. (Yield 0.08 g, 30.8%).

HRMS(ES$^+$) m/z Calcd for C$_{23}$H$_{19}$Cl$_2$NO+H [(M+H)$^+$]: 396.0917. Found: 396.0918.

EXAMPLE 53a rac-6-Chloro-3-hydroxy-3-(4-isopropyl-phenyl)-1,3-dihydro-indol-2-one

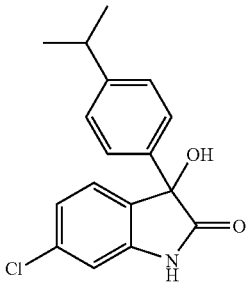

M.W. 301.78 C$_{17}$H$_{16}$ClNO$_2$

A solution of 4-isopropyl-phenyl magnesium bromide in tetrahydrofuran (0.5 M, 3.3 mL, 1.65 mmol) (Aldrich) was added dropwise with magnetic stirring to a suspension of 6-chloroisatin (0.2 g, 1.1 mmol) in tetrahydrofuran (5 mL) with cooling in a −25° C. bath. Cooling bath was then removed and mixture was allowed to warm to room temperature. After stirring for an additional 3 hours, 15% aqueous ammonium chloride solution was added and mixture extracted with ethyl acetate. The combined organic layers were then washed with water, brine, combined, dried (Na$_2$SO$_4$), filtered and concentrated. Residue was stirred in dichloromethane at room temperature for 15 minutes and filtered to give crude rac-6-chloro-3-hydroxy-3-(4-isopropyl-phenyl)-1,3-dihydro-indol-2-one as a pale yellow solid. This was used in the next step without further purification.

EXAMPLE 53b rac-6-Chloro-3-(4-isopropyl-phenyl)-1,3-dihydro-indol-2-one

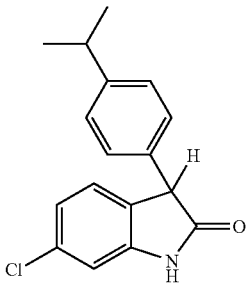

M.W. 285.78 C$_{17}$H$_{16}$ClNO

Crude rac-6-chloro-3-hydroxy-3-(4-isopropyl-phenyl)-1,3-dihydro-indol-2-one (0.13 g, 0.43 mmol) (from Example 53a supra) was suspended in a mixture of triethylsilane (0.15 g, 1.29 mmol) (Aldrich) and trifluoroacetic acid (0.73 g, 6.48 mmol) and heated in an 80° C. oil bath for 17 hours. After cooling to room temperature, mixture was diluted with ethyl acetate and treated with solid sodium carbonate (1 g). After stirring for 30 minutes, mixture was extracted with water and brine. Aqueous layers were back washed with ethyl acetate. Organic layers were combined, dried (Na$_2$SO$_4$), filtered and concentrated. Residue was recrystallized from dichloromethane-hexanes to give rac-6-chloro-3-(4-isopropyl-phenyl)-1,3-dihydro-indol-2-one as a pale yellow solid. (Yield 0.11 g, 91%)

EXAMPLE 53c rac-6-Chloro-3-(3-chloro-benzyl)-3-(4-isopropyl-phenyl)-1,3-dihydro-indol-2-one

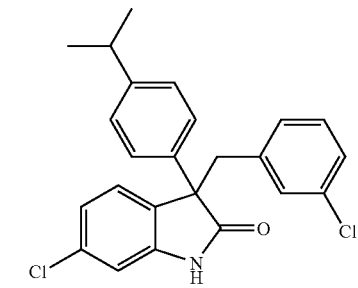

M.W. 410.342 C$_{24}$H$_{21}$Cl$_2$NO

A mixture of rac-6-chloro-3-(4-isopropyl-phenyl)-1,3-dihydro-indol-2-one (0.11 g, 0.38 mmol) (from Example 53b supra), 3-chlorobenzyl bromide (0.093 g, 0.454 mmol) (Aldrich), potassium iodide (0.0762 g, 0.44 mmol) and potassium carbonate (0.114 g, 0.82 mmol) in acetone (3 mL) was heated at 70° C. for 3 hours. After cooling, mixture was partitioned between ethyl acetate and water. The aqueous layer was extracted with ethyl acetate three times. The combined organic layer was washed with water and brine, dried (Na$_2$SO$_4$), filtered and concentrated. Residue was purified by chromatography to give rac-6-chloro-3-(3-chloro-benzyl)-3-(4-isopropyl-phenyl)-1,3-dihydro-indol-2-one as brown solid. (Yield 0.09 g, 56.9%).

HRMS(ES$^+$) m/z Calcd for C$_{24}$H$_{21}$Cl$_2$NO+H [(M+H)$^+$]: 410.1073. Found: 410.1074.

EXAMPLE 54 rac-3-[6-Chloro-3-(3-chloro-benzyl)-2-oxo-2,3-dihydro-1H-indol-3-yl]-piperidine-1-carboxylic acid (4-diomethylamino-phenyl)-amide

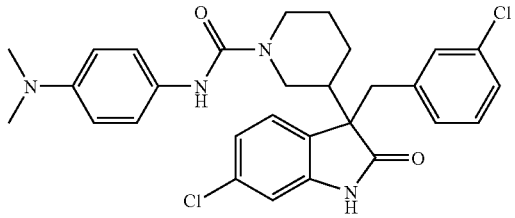

M.W. 537.488 C$_{29}$H$_{30}$Cl$_2$N$_4$O$_2$

To a solution of rac-6-chloro-3-(3-chloro-benzyl)-3-piperidin-3-yl-1,3-dihydro-indol-2-one (80 mg, 0.22 mmol) (from Example 25a supra) in dichloromethane (3 mL) was added triethylamine (74.3 ul, 0.53 mmol) (Aldrich), followed by the addition of 4-isocyanato-phenyl)-dimethyl-amine (42 mg, 0.26 mmol) (Aldrich). The mixture was stirred at room temperature for 30 minutes. The mixture was partitioned between dichloromethane and water. The aqueous layer was extracted with dichloromethane. The combined organic layers were washed with water, brine, dried over $Na_2SO_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-diomethylamino-phenyl)-amide as a white solid. (Yield 60 mg, 52.6%).

HRMS(ES$^+$) m/z Calcd for $C_{29}H_{30}Cl_2N_4O_2$+H [(M+H)$^+$]: 537.1819. Found: 537.1819.

EXAMPLE 55 rac-4-({3-[6-Chloro-3-(3-chloro-benzyl)-2-oxo-2,3-dihydro-1H-indol-3-yl]-piperidine-1-carbonyl}-amino)-benzoic acid ethyl ester

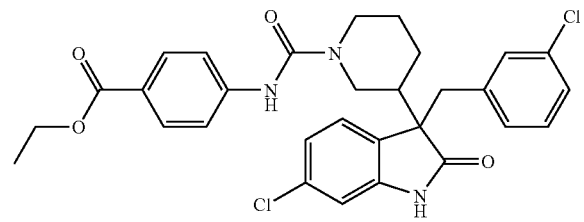

M.W. 566.482 $C_{30}H_{29}Cl_2N_3O_4$

To a solution of rac-6-chloro-3-(3-chloro-benzyl)-3-piperidin-3-yl-1,3-dihydro-indol-2-one (0.15 g, 0.40 mmol) (from Example 25a supra) in dichloromethane (3 mL) was added triethylamine (0.139 ul, 1.0 mmol) (Aldrich), followed by the addition of 4-isocyanato-benzoic acid ethyl ester (92.0 mg, 0.48 mmol) (Aldrich). The mixture was stirred at room temperature for 30 minutes. The mixture was partitioned between dichloromethane and water. The aqueous layer was extracted with dichloromethane. The combined organic layers were washed with water, brine, dried over $Na_2SO_4$ and concentrated. The residue was purified by chromatography to give rac-4-({3-[6-chloro-3-(3-chloro-benzyl)-2-oxo-2,3-dihydro-1Hindol-3-yl]-piperidine-1-carbonyl}-amino)-benzoic acid ethyl ester as a white solid. (Yield 0.14 g, 60.8%).

HRMS(ES$^+$) m/z Calcd for $C_{30}H_{29}Cl_2N_3O_4$+H [(M+H)$^+$]: 566.1608. Found: 566.1616.

EXAMPLE 56 rac-3-[6-Chloro-3-(3-chloro-benzyl)-2-oxo-2,3-dihydro-1H-indol-3-yl]-piperidine-1-carboxylic acid (4-butoxy-phenyl)-amide

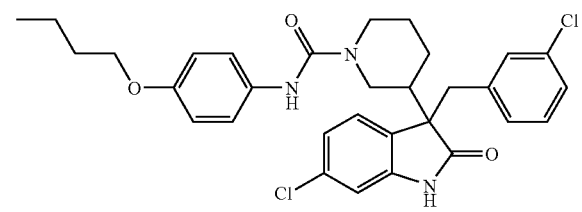

M.W. 566.526 $C_{31}H_{33}Cl_2N_3O_3$

To a solution of rac-6-chloro-3-(3-chloro-benzyl)-3-piperidin-3-yl-1,3-dihydro-indol-2-one (80 mg, 0.21 mmol) (from Example 25a supra) in dichloromethane (3 mL) was added triethylamine (74.3 ul, 0.53 mmol) (Aldrich), followed by the addition of 1-butoxy-4-isocyanato-benzene (49.0 mg, 0.26 mmol) (Aldrich). The mixture was stirred at room temperature for 30 minutes. The mixture was partitioned between dichlormethane and water. The aqueous layer was extracted with dichlormethane. The combined organic layers were washed with water, brine, dried over $Na_2SO_4$ and concentrated. The residue was purified by chromatography to give rac-3-[6-chloro-3-(3-chloro-benzyl)-2-oxo-2,3-dihydro-1H-indol 3-yl]-piperidine-1-carboxylic acid (4-butoxy-phenyl)-amide as a white solid. (Yield 0.05 g, 41.7%).

HRMS(ES$^+$) m/z Calcd for $C_{31}H_{33}Cl_2N_3O_3$+H [(M+H)$^+$]: 566.1972. Found: 566.1975.

EXAMPLE 57 rac-3-[6-Chloro-3-(3-chloro-benzyl)-2-oxo-2,3-dihydro-1H-indol-3-yl]-piperidine-1-carboxylic acid (4-trifluoromethoxy-phenyl)-amide

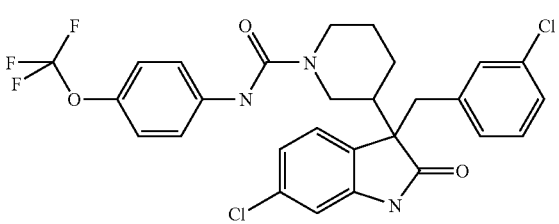

M. W. 578.416 $C_{28}H_{24}ClF_3N_3O_3$

To a solution of rac-6-chloro-3-(3-chloro-benzyl)-3-piperidin-3-yl-1,3-dihydro-indol-2-one (80 mg, 0.21 mmol) (from Example 25a supra) in dichloromethane (3 mL) was added triethylamine (74.3 ul, 0.53 mmol) (Aldrich), followed by the addition of 1-isocyanato-4-trifluoromethoxy-benzene (52.0 mg, 0.26 mmol) (Aldrich). The mixture was stirred at room temperature for 30 minutes. The mixture was partitioned between dichlormethane and water. The aqueous layer was extracted with dichlormethane. The combined organic layers were washed with water, brine, dried over $Na_2SO_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-trifluoromethoxy-phenyl)-amide as a white solid. (Yield 82 mg, 66.7%).

HRMS(ES$^+$) m/z Calcd for $C_{28}H_{24}Cl_2F_3N_3O_3$+H [(M+H)$^+$]: 578.1220. Found: 578.1221.

EXAMPLE 58a

4-Isocyanato-pyridine

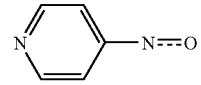

M.W. 120.11 $C_6H_4N_2O$

To a suspension of isonicotinic acid (0.369 g, 3 mmol) (Aldrich) in toluene (15 mL) was added diphenylphosphoryl azide (0.958 g, 3.5 mmol) (Aldrich), followed by the addition of triethylamine (0.35 g, 3.6 mmol) (Aldrich). The mixture was stirred at room temperature for 30 minutes and the mixture became clear. Then the mixture was heated at 80° C. for 2 hours. The mixture was cooling down to room temperature to give crude 4-isocyanato-pyridine as 0.2 M solution of toluene and used for the next step without further purification.

EXAMPLE 58b rac-3-[6-Chloro-3-(3-chloro-benzyl)-2-oxo-2,3-dihydro-1H-indol-3-yl]-piperidine-1-carboxylic acid pyridine-4-ylamide

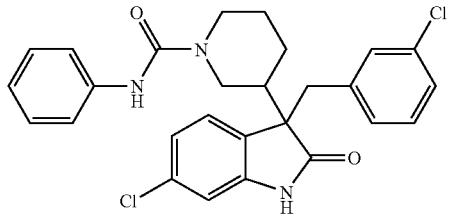

M.W. 495.408 $C_{26}H_{24}Cl_2N_4O_2$

To a solution of rac-6-chloro-3-(3-chloro-benzyl)-3-piperidin-3-yl-1,3-dihydro-indol-2-one (80 mg, 0.21 mmol) (from Example 25a supra) in dichloromethane (3 mL) was added triethylamine (74.3 ul, 0.53 mmol) (Aldrich), followed by the addition of solution of 4-isocyanato-pyridine (1.28 mL, 0.26 mmol) in toluene (from Example 58a supra). The mixture was stirred at room temperature for 30 minutes. The mixture was partitioned between dichlormethane and water. The aqueous layer was extracted with dichlormethane. The combined organic layer was washed with water, brine, dried over Na$_2$SO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid pyridine-4-ylamide as a white solid. (Yield 23 mg, 21.9%).

HRMS(ES$^+$) m/z Calcd for $C_{26}H_{24}Cl_2N_4O_2$+H [(M+H)$^+$]: 495.1349. Found: 495.1351.

EXAMPLE 59 rac-3-[6-Chloro-3-(3-chloro-benzyl)-2-oxo-2,3-dihydro-1H-indol-3-yl]-piperidine-1-carboxylic acid (2,6-dichloro-pyridin-4-yl)-amide

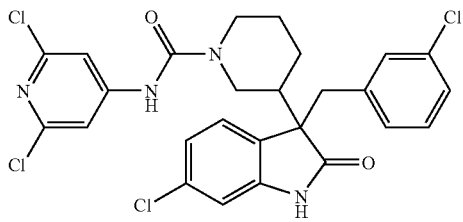

M.W. 564.298 $C_{26}H_{22}Cl_4N_4O_2$

To a solution of rac-6-chloro-3-(3-chloro-benzyl)-3-piperidin-3-yl-1,3-dihydro-indol-2-one (80 mg, 0.21 mmol) (from Example 25a supra) in dichloromethane (3 mL) was added triethylamine (53.9 mg, 0.53 mmol) (Aldrich), followed by the addition of 2,6-dichloro-4-isocyanato-pyridine (49.0 mg, 0.26 mmol) (Acros). The mixture was stirred at room temperature for 30 minutes. The mixture was partitioned between dichlormethane and water. The aqueous layer was extracted with dichlormethane. The combined organic layers were washed with water, brine, dried over Na$_2$SO$_4$ and concentrated. The residue was purified by chromatography to give rac-3-[6-chloro-3-(3-chloro-benzyl)-2-oxo-2,3-dihydro-1H-indo-3-yl]-piperidine-1-carboxylic acid (2,6-dichloro-pyridin-4-yl)-amide as a white solid. (Yield 0.055 g, 45.9%).

HRMS(ES$^+$) m/z Calcd for $C_{26}H_{22}Cl_4N_4O_2$+H [(M+H)$^+$]: 563.0570 Found: 563.0574.

EXAMPLE 60a rac-3-Bromo-6-chloro-3-(3-chloro-benzyl)-1,3-dihydro-indol-2-one

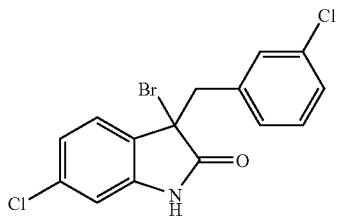

M.W. 371.06 $C_{15}H_{10}BrCl_2NO$

Pyridinium bromide perbromide (0.659 g, 2.06 mmol) (Aldrich) was added in one portion to a solution of 6-chloro-3-(3-chloro-benzyl)-1,3-dihydro-indol-2-one (0.5 g, 1.72 mmol) (from Example 30b supra) in t-BuOH (16.2 mL) and H$_2$O (74 uL) at room temperature with stirring. After stirring at room temperature for 4 hours, the crude was diluted with water, extracted with ethyl acetate three times. The combined organic layers were washed with brine, dried over MgSO$_4$. After filtration, the solvent was removed to obtain rac-3-bromo-6-chloro-3-(3-chloro-benzyl)-1,3-dihydro-indol-2-one as a pale yellow solid (yield: 0.64 g, 84%).

EXAMPLE 60b rac-6-chloro-3-(3-chloro-benzyl)-3-(4-dimethylamino-phenyl)-1,3-dihydro-indol-2-one

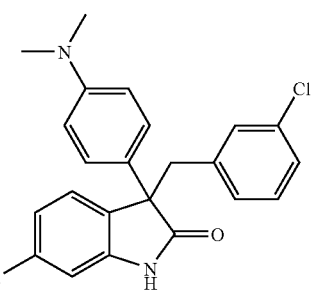

M.W. 411.33 $C_{23}H_{20}Cl_2N_2O$

To the suspension of cesium carbonate (0.147 g, 0.45 mmol) (Aldrich) in dichloromethane (2 mL) was added N,N- dimethylaniline (27.4 mg, 0.23 mmol) (Aldrich), followed by the addition of 3-bromo-6-chloro-3-(3-chloro-benzyl)-1,3-dihydro-indol-2-one (70 mg, 0.19 mmol) (from Example 60a supra) in dichloromethane (2 mL). The reaction mixture was stirred at room temperature for 24 hours. The reaction was quenched with water, extracted with dichloromethane three times. The combined organic layer was washed with water, brine, dried over MgSO$_4$. After filtration, the solvent was removed. The residue was purified by chromatography to give rac-6-chloro-3-(3-chloro-benzyl)-3-(4-dimethylamino-phenyl)-1,3-dihydro-indol-2-one as a white solid. (Yield: 35 mg, 45%).

HRMS(ES$^+$) m/z Calcd for $C_{23}H_{20}Cl_2N_2O+H$ [(M+H)$^+$]: 411.1026 Found: 411.1027.

EXAMPLE 61a 4-(6-Chloro-2-oxo-1,2-dihydro-indol-3-ylidene)-azepane-1-carboxylic acid tert-butyl ester

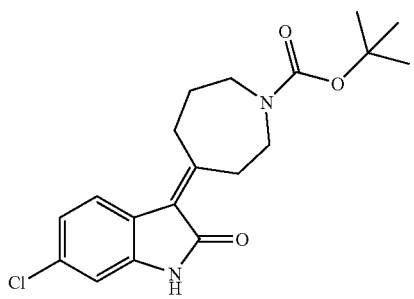

M.W. 362.86 $C_{19}H_{23}ClN_2O_3$

A suspension of 6-chlorooxindole (0.71 g, 4.24 mmol) (Cresent Chem.), (3-oxo-butyl)-propyl-carbamic acid tert-butyl ester (1 g, 4.69 mmol) (Tyger Sci.), and pyrrolidine (0.1 g) (Aldrich) in 2-propanol (15 mL) was heated at 90° C. for 2 days. The mixture was allowed to cool to room temperature. The solvent was removed and the residue was purified by chromatography to give 4-(6-chloro-2-oxo-1,2-dihydro-in-dol-3-ylidene)-azepane-1-carboxylic acid tert-butyl ester as a brown solid. (Yield: 1.36 g, 88%).

EXAMPLE 61b rac-4-(6-Chloro-2-oxo-2,3-dihydro-1H-indol-3-yl)-azepane-1-carboxylic acid tert-butyl ester

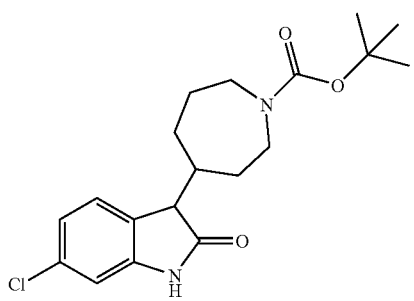

M.W. 364.88. $C_{19}H_{25}ClN_2O_3$

Sodium borohydride (1.42 g, 37.5 mmol) (Aldrich) was added in small portions to a solution of rac-4-(6-chloro-2-oxo-1,2-dihydro-indol-3-ylidene)-azepane-1-carboxylic acid tert-butyl ester (1.36 g, 3.75 mmol) (from Example 61a supra) in methanol (25 mL) and water (0.5 mL). After stirring at room temperature for 30 minutes, the reaction mixture was concentrated. The residue was partitioned between ethyl acetate and water. The aqueous layer was extracted with ethyl acetate three times. The combined organic layers were washed with water, brine, dried over Na$_2$SO$_4$ and concentrated to give rac-4-(6-chloro-2-oxo-2,3-dihydro-1H-indol-3-yl)-azepane-1-carboxylic acid tert-butyl ester as a white solid (Yield 1.37 g, 100%).

EXAMPLE 61c rac-4-[6-Chloro-3-(3-chloro-benzyl)-2-oxo-2,3-dihydro-1H-indol-3-yl]-azepane-1-carboxylic acid tert-butyl ester

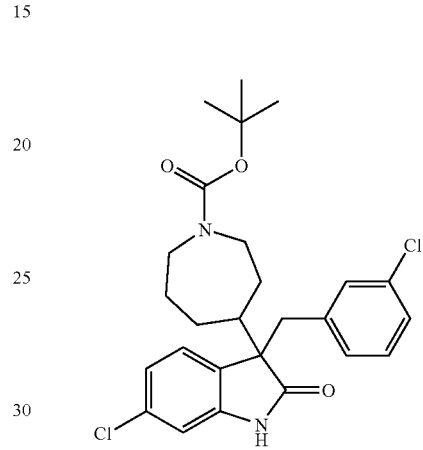

M.W. 489.44 $C_{26}H_{30}Cl_2N_2O_3$

A mixture of rac-4-(6-chloro-2-oxo-2,3-dihydro-1H-in-dol-3-yl)-azepane-1-carboxylic acid tert-butyl ester (0.3 g, 0.82 mmol) (from Example 61b supra), 3-chlorobenzyl bromide (0.20 g, 0.97 mmol) (Aldrich), potassium iodide (0.16 g, 0.98 mmol) and potassium carbonate (0.24 g, 1.77 mmol) in acetone (5 mL) was heated at 50° C. for overnight The solvent was removed. The residue was purified by chromatography to give rac-4-[6-chloro-3-(3-chloro-benzyl)-2-oxo-2,3-dihy-dro-1H-indol-3-yl]-azepane-1-carboxylic acid tert-butyl ester as white solid. (Yield 50 mg, 12.5%).

HRMS(ES$^+$) m/z Calcd for $C_{26}H_{30}Cl_2N_2O_3+H$ [(M+H)$^+$]: 489.1706. Found: 489.1707.

EXAMPLE 62a

5-Isocyanato-2-methoxy-pyridine

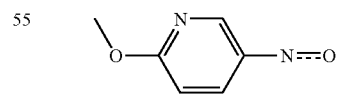

M.W. 150.14 $C_7H_6N_2O_2$

To a suspension of 6-methoxy-nicotinic acid (0.459 g, 3 mmol) (Matrix) in toluene (15 mL) was added diphenylphosphoryl azide (0.958 g, 3.5 mmol) (Aldrich), followed by the addition of triethylamine (0.35 g, 3.6 mmol) (Aldrich). The mixture was stirred at room temperature for 30 minutes and the mixture became clear. Then the mixture was heated at 80°

C. for 2 hours. The mixture was cooling down to room temperature to give crude 5-isocyanato-2-methoxy-pyridine as 0.2 M solution of toluene and used for the next step without further purification.

EXAMPLE 62b rac-3-[6-Chloro-3-(3-chloro-benzyl)-2-oxo-2,3-dihydro-1H-indol-3-yl]-piperidine-1-carboxylic acid (6-methoxy-pyridin-3-yl)-amide

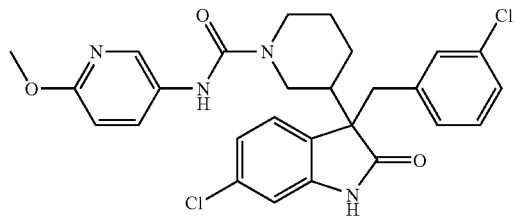

M.W. 525.44 $C_{27}H_{26}Cl_2N_4O_3$

To a solution of rac-6-chloro-3-(3-chloro-benzyl)-3-piperidin-3-yl-1,3-dihydro-indol-2-one (80 mg, 0.21 mmol) (from Example 25a supra) in dichloromethane (3 mL) was added triethylamine (74.3 ul, 0.53 mmol) (Aldrich), followed by the addition of solution of 5-isocyanato-2-methoxy-pyridine (1.28 mL, 0.26 mmol) in toluene (from Example 62a supra). The mixture was stirred at room temperature for 30 minutes. The mixture was partitioned between dichlormethane and water. The aqueous layer was extracted with dichlormethane. The combined organic layer was washed with water, brine, dried over $Na_2SO_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (6-methoxy-pyridin-3-yl)-amide as a white solid. (Yield 55 mg, 49.1%).

HRMS(ES$^+$) m/z Calcd for $C_{27}H_{26}Cl_2N_4O_3$+H [(M+H)$^+$]: 525.1455. Found: 525.1456.

EXAMPLE 63 rac-4-({3-[6-Chloro-3-(3-chloro-benzyl)-2-oxo-2,3-dihydro-1H-indol-3-yl]-piperidine-1-carbonyl}-amino)-benzoic acid methyl ester

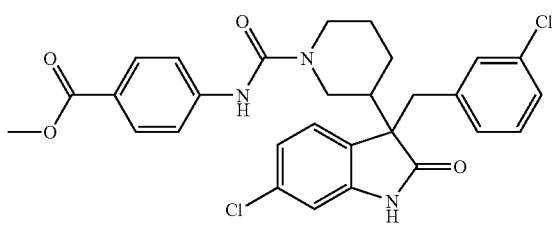

M.W. 552.455 $C_{29}H_{27}Cl_2N_3O_4$

To a solution of rac-6-chloro-3-(3-chloro-benzyl)-3-piperidin-3-yl-1,3-dihydro-indol-2-one (0.25 g, 0.67 mmol) (from Example 25a supra) in dichloromethane (3 mL) was added triethylamine (0.168 g, 1.67 mmol) (Aldrich), followed by the addition of 4-isocyanato-benzoic acid methyl ester (0.142 g, 0.80 mmol) (Aldrich). The mixture was stirred at room temperature for 30 minutes. The mixture was partitioned between dichlormethane and water. The aqueous layer was extracted with dichlormethane. The combined organic layers were washed with water, brine, dried over $Na_2SO_4$ and concentrated. The residue was purified by chromatography to give rac-4-({3-[6-chloro-3-(3-chloro-benzyl)-2-oxo-2,3-dihydro-1H-indol-3-yl]-piperidine-1-carbonyl}-amino)-benzoic acid methyl ester as a white solid. (Yield 0.3 g, 82%).

HRMS(ES$^+$) m/z Calcd for $C_{29}H_{27}Cl_2N_3O_4$+H [(M+H)$^+$]: 552.1452. Found: 552.1447.

EXAMPLE 64 rac-4-({3-[6-Chloro-3-(3-chloro-benzyl)-2-oxo-2,3-dihydro-1H-indol-3-yl]-piperidine-1-carbonyl}-amino)-benzoic acid

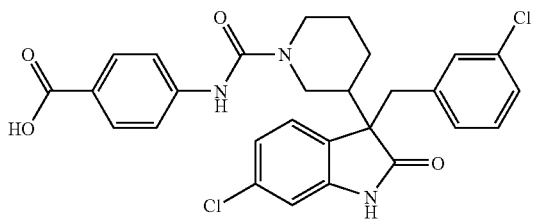

M.W. 538.428 $C_{28}H_{25}Cl_2N_3O_4$

To a solution of rac-4-({3-[6-chloro-3-(3-chloro-benzyl)-2-oxo-2,3-dihydro-1H-indol-3-yl]-piperidine-1-carbonyl}-amino)-benzoic acid methyl ester (0.24 g, 0.44 mmol) (from Example 63 supra) in tetrahydro furan (2.5 mL) was added the suspension of lithium hydroxide monohydrate (0.18 g, 4.4 mmol) (Aldrich). The mixture was stirred at room temperature for overnight. The solvent was removed and the residue was partitioned between ethyl acetate and water. The aqueous layer was acidified to pH<5 with dilute HCl, then extracted with ethyl acetate several times. The combined organic layer was washed with water, brine, dried over $MgSO_4$ and concentrated to give rac-4-({3-[6-chloro-3-(3-chloro-benzyl)-2-oxo-2,3-dihydro-1H-indol-3-yl]-piperidine-1-carbonyl}-amino)-benzoic acid as a white solid.

(Yield 0.2 g, 85.8%).

HRMS(ES$^+$) m/z Calcd for $C_{28}H_{25}Cl_2N_3O_4$+H [(M+H)$^+$]: 538.1295. Found: 538.1298.

EXAMPLE 65 rac-3-(1-Benzyl-piperidin-3-yl)-6-chloro-3-(3-chloro-benzyl)-1,3-dihydro-indol-2-one

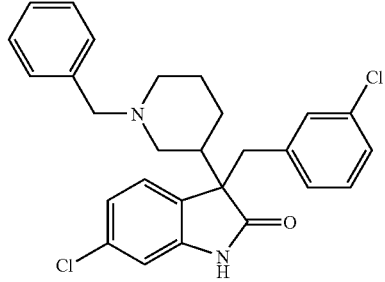

M. W. 465.421 $C_{27}H_{26}Cl_2N_2O$

To a solution of rac-6-chloro-3-(3-chloro-benzyl)-3-piperidin-3-yl-1,3-dihydro-indol-2-one (0.1 g, 0.27 mmol)

(from Example 25a supra) in acetone (3 mL) was added potassium carbonate (92 mg, 0.68 mmol) (Aldrich), followed by the addition of bromomethyl-benzene (54.7 mg, 0.32 mmol) (Aldrich). The mixture was stirred at room temperature for 3 hours. The solvent was removed and the residue was partitioned between ethyl acetate and water. The aqueous layer was extracted with ethyl acetate. The combined organic layer was washed with water, brine, dried over Na$_2$SO$_4$ and concentrated. The residue was purified by chromatography to give rac-3-(1-benzyl-piperidin-3-yl)-6-chloro-3-(3-chloro-benzyl)-1,3-dihydro-indol-2-one as a white solid. (Yield 45 mg, 36.3%).

HRMS(ES$^+$) m/z Calcd for C$_{27}$H$_{26}$Cl$_2$N$_2$O+H [(M+H)$^+$]: 465.1495. Found: 465.1491.

EXAMPLE 66a

2-Chloro-5-Isocyanato-pyridine

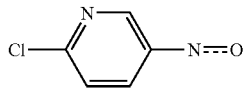

M.W. 154.56 C$_6$H$_3$ClN$_2$O

To a suspension of 6-chloro-nicotinic acid (0.468 g, 3 mmol) (Aldrich) in toluene (15 mL) was added diphenylphosphoryl azide (0.958 g, 3.5 mmol) (Aldrich), followed by the addition of triethylamine (0.35 g, 3.6 mmol) (Aldrich). The mixture was stirred at room temperature for 30 minutes and the mixture became clear. Then the mixture was heated at 80° C. for 2 hours. The mixture was cooling down to room temperature to give crude 2-chloro-5-Isocyanato-pyridine as 0.2 M solution of toluene and used for the next step without further purification.

EXAMPLE 66b rac-3-[6-Chloro-3-(3-chloro-benzyl)-2-oxo-2,3-dihydro-1H-indol-3-yl]-piperidine-1-carboxylic acid (6-chloro-pyridin-3-yl)-amide

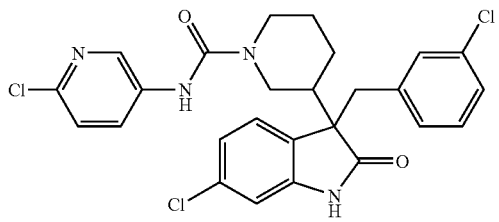

M.W. 529.853 C$_{26}$H$_{23}$Cl$_3$N$_4$O$_2$

To a solution of rac-6-chloro-3-(3-chloro-benzyl)-3-piperidin-3-yl-1,3-dihydro-indol-2-one (80 mg, 0.21 mmol) (from Example 25a supra) in dichloromethane (3 mL) was added triethylamine (74.3 ul, 0.53 mmol) (Aldrich), followed by the addition of solution of 2-chloro-5-isocyanato-pyridine (1.28 mL, 0.26 mmol) in toluene (from Example 66a supra). The mixture was stirred at room temperature for 30 minutes. The mixture was partitioned between dichlormethane and water. The aqueous layer was extracted with dichlormethane. The combined organic layer was washed with water, brine, dried over Na$_2$SO$_4$ and concentrated. The residue was purified by chromatography to give rac-3-[6-Chloro-3-(3-chloro-benzyl)-2-oxo-2,3-dihydro-1H-indol-3-yl]-piperidine-1-carboxylic acid (6-chloro-pyridin-3-yl)-amide as a white solid. (Yield 32 mg, 28.3%).

HRMS(ES$^+$) m/z Calcd for C$_{26}$H$_{23}$Cl$_3$N$_4$O$_2$+H [(M+H)$^+$]: 529.0960. Found: 529.0959.

EXAMPLE 67 rac-3-[6-Chloro-3-(3-chloro-benzyl)-2-oxo-2,3-dihydro-1H-indol-3-yl]-piperidine-1-carboxylic acid (4-carbamoyl-phenyl)-amide

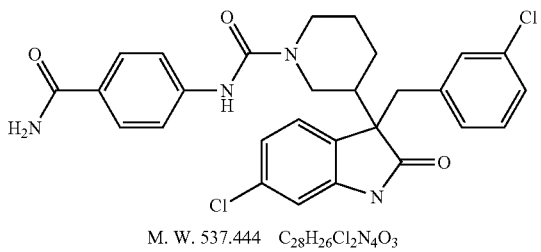

M. W. 537.444   C$_{28}$H$_{26}$Cl$_2$N$_4$O$_3$

To a solution of rac-4-({3-[6-chloro-3-(3-chloro-benzyl)-2-oxo-2,3-dihydro-1H-indol-3-yl]-piperidine-1-carbonyl}-amino)-benzoic acid (50 mg, 0.093 mmol) (from Example 64 supra) in DMF (1.5 mL) was added diisopropyl ethylamine (48.0 mg, 0.37 mmol) (Aldrich), followed by the addition N-(3-dimethylaminopropyl)-N'-ethylcarbodiimide hydrochloride (35.5 mg, 0.18 mmol) (Aldrich), 1-hydroxybenzotriazole (25.0 mg, 0.18 mmol) (Aldrich) and ammonium chloride (9.8 mg, 0.18 mmol) (Aldrich). The mixture was stirred at room temperature for 2 hours and then heated at 60° C. for 2 hours. The mixture was partitioned between ethyl acetate and water. The aqueous layer was extracted with ethyl acetate. The combined organic layers were washed with water, brine, dried over MgSO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-carbamoyl-phenyl)-amide as a white solid. (Yield 25 mg, 50%).

HRMS(ES$^+$) m/z Calcd for C$_{28}$H$_{26}$Cl$_2$N$_4$O$_3$+H [(M+H)$^+$]: 537.1455. Found: 537.1449.

EXAMPLE 68 rac-3-({3-[6-Chloro-3-(3-chloro-benzyl)-2-oxo-2,3-dihydro-1H-indol-3-yl]-piperidine-1-carbonyl}-amino)-benzoic acid methyl ester

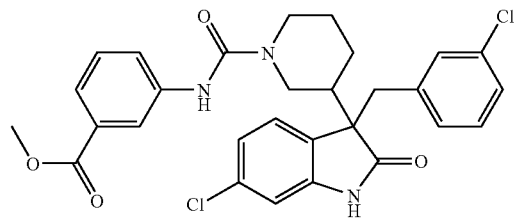

M.W. 552.455 C$_{29}$H$_{27}$Cl$_2$N$_3$O$_4$

To a solution of rac-6-chloro-3-(3-chloro-benzyl)-3-piperidin-3-yl-1,3-dihydro-indol-2-one (70 mg, 0.19 mmol) (from Example 25a supra) in dichloromethane (3 mL) was added triethylamine (64.9 uL, 0.48 mmol) (Aldrich), followed by the addition of 3-isocyanato-benzoic acid methyl ester (39.7 mg, 0.22 mmol) (Aldrich). The mixture was stirred at room temperature for 30 minutes. The mixture was partitioned between dichlormethane and water. The aqueous layer was extracted with dichlormethane. The combined organic layer was washed with water, brine, dried over MgSO$_4$ and concentrated. The residue was purified by chromatography to give rac-3-({3-[6-chloro-3-(3-chloro-benzyl)-2-oxo-2,3-dihydro-1H-indol-3-yl]-piperidine-1-carbonyl}-amino)-benzoic acid methyl ester as a white solid. (Yield 70 mg, 68%).

HRMS(ES$^+$) m/z Calcd for C$_{29}$H$_{27}$Cl$_2$N$_3$O$_4$+H [(M+H)$^+$]: 552.1452. Found: 552.1450.

EXAMPLE 69 rac-3-({3-[6-Chloro-3-(3-chloro-benzyl)-2-oxo-2,3-dihydro-1H-indol-3-yl]-piperidine-1-carbonyl}-amino)-benzoic acid

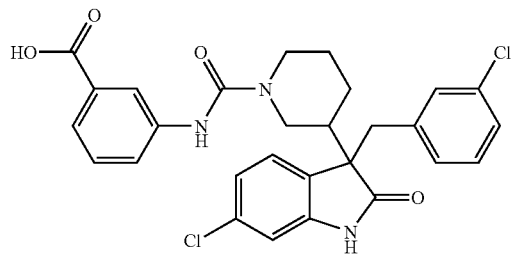

M.W. 538.428 C$_{28}$H$_{25}$Cl$_2$N$_3$O$_4$

To a solution of rac-3-({3-[6-chloro-3-(3-chloro-benzyl)-2-oxo-2,3-dihydro-1H-indol-3-yl]-piperidine-1-carbonyl}-amino)-benzoic acid methyl ester (50 mg, 0.090 mmol) (from Example 68 supra) in tetrahydro furan (2 mL) was added the suspension of lithium hydroxide monohydrate (38 mg, 0.9 mmol) (Aldrich). The mixture was stirred at room temperature for 2 days. The solvent was removed and the residue was partitioned between ethyl acetate and water. The aqueous layer was acidified to pH<5 with dilute HCl, then extracted with ethyl acetate several times. The combined organic layer was washed with water, brine, dried over MgSO$_4$ and concentrated. The rsidue was triturated with Dichloromethane-Hexane to give rac-3-({3-[6-chloro-3-(3-chloro-benzyl)-2-oxo-2,3-dihydro-1H-indol-3-yl]-piperidine-1-carbonyl}-amino)-benzoic acid as a white solid. (Yield 40 mg, 81.6%).

HRMS(ES$^+$) m/z Calcd for C$_{28}$H$_{25}$Cl$_2$N$_3$O$_4$+H [(M+H)$^+$]: 538.1295. Found: 538.1290.

EXAMPLE 70 rac-3-[6-Chloro-3-(3-chloro-benzyl)-2-oxo-2,3-dihydro-1H-indol-3-yl]-piperidine-1-carboxylic acid (4-fluoro-phenyl)-amide

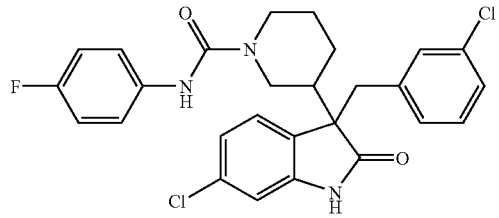

M.W. 512.41 C$_{27}$H$_{24}$Cl$_2$FN$_3$O$_2$

To a solution of rac-6-chloro-3-(3-chloro-benzyl)-3-piperidin-3-yl-1,3-dihydro-indol-2-one (50 mg, 0.13 mmol) (from Example 25a supra) in dichloromethane (3 mL) was added triethylamine (33.6 mg, 0.33 mmol) (Aldrich), followed by the addition of 1-fluoro-4-isocyanato-benzene (39.7 mg, 0.22 mmol) (Aldrich). The mixture was stirred at room temperature for 30 minutes. The mixture was partitioned between dichlormethane and water. The aqueous layer was extracted with dichlormethane. The combined organic layer was washed with water, brine, dried over MgSO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-fluoro-phenyl)-amide as a white solid (Yield 40 mg, 59%).

HRMS(ES$^+$) m/z Calcd for C$_{27}$H$_{24}$Cl$_2$FN$_3$O$_2$+H [(M+H)$^+$]: 512.1303. Found: 512.1298.

EXAMPLE 71a

5-Isocyanato-2-methyl-pyridine

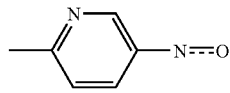

M.W. 134.14 C$_7$H$_6$N$_2$O

To a suspension of 6-methyl-nicotinic acid (0.41 g, 3 mmol) (Aldrich) in toluene (15 mL) was added diphenylphosphoryl azide (0.958 g, 3.5 mmol) (Aldrich), followed by the addition of triethylamine (0.35 g, 3.6 mmol) (Aldrich). The mixture was stirred at room temperature for 30 minutes and the mixture became clear. Then the mixture was heated at 80° C. for 2 hours. The mixture was cooling down to room temperature to give crude 5-isocyanato2-methyl-pyridine as 0.2 M solution of toluene and used for the next step without further purification.

EXAMPLE 71b rac-3-[6-Chloro-3-(3-chloro-benzyl)-2-oxo-2,3-dihydro-1H-indol-3-yl]-piperidine-1-carboxylic acid (6-methyl-pyridine-3-yl)-amide

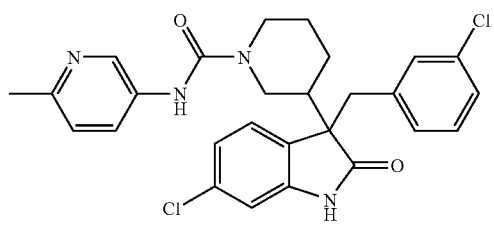

M.W. 509.434 C$_{27}$H$_{26}$Cl$_2$N$_4$O$_2$

To a solution of rac-6-chloro-3-(3-chloro-benzyl)-3-piperidin-3-yl-1,3-dihydro-indol-2-one (80 mg, 0.21 mmol) (from Example 25a supra) in dichloromethane (3 mL) was added triethylamine (74.3 ul, 0.53 mmol) (Aldrich), followed by the addition of solution of 5-Isocyanato-2-methyl-pyridine (1.26 mL, 0.25 mmol) in toluene (from Example 71a supra). The mixture was stirred at room temperature for 30 minutes. The mixture was partitioned between dichlormethane and water. The aqueous layer was extracted with dichlormethane. The combined organic layer was washed with water, brine, dried over MgSO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (6-methyl-pyridine-3-yl)-amide as a white solid. (Yield 52 mg, 48.1%).

HRMS(ES⁺) m/z Calcd for $C_{27}H_{26}Cl_2N_4O_2$+H [(M+H)⁺]: 509.1506. Found: 509.1502.

EXAMPLE 72 rac-6-Chloro-3-(3-chloro-benzyl)-3-{1-(pyridine-4-carbonyl)-piperidin-4-yl}-1,3-dihydro-indol-2-one

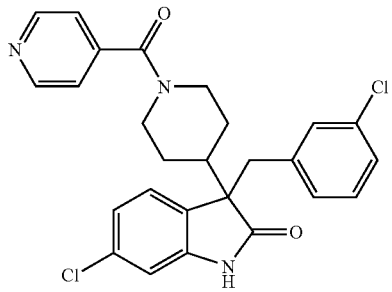

M.W. 480.393 $C_{26}H_{23}Cl_2N_3O_2$

To a solution of rac-6-chloro-3-(3-chloro-benzyl)-3-piperidin-3-yl-1,3-dihydro-indol-2-one (50 mg, 0.13 mmol) (from Example 25a supra) in tetrahydrofuron (2 mL) was added triethyl amine (20.2 mg, 0.19 mmol) (Aldrich), followed by the addition of isonicotinoyl chloride (28.5 mg, 0.16 mmol) (Aldrich). The mixture was heated at 60° C. for 14 hours and then cooled down to room temperature. The solvent was removed and the residue was partitioned between ethyl acetate and water. The aqueous layer was extracted with ethyl acetate. The combined organic layer was washed with water, brine, dried over MgSO₄ and concentrated. The residue was purified by chromatography to give rac-6-chloro-3-(3-chloro-benzyl)-3-{1-(pyridine-4-carbonyl)-piperidin-4-yl}-1,3-dihydro-indol-2-one as a white solid. (Yield 31 mg, 48.4%).

HRMS(ES⁺) m/z Calcd for $C_{26}H_{23}Cl_2N_3O_2$+H [(M+H)⁺]: 480.1240. Found: 480.1235.

EXAMPLE 73 rac-6-Chloro-3-(3-chloro-benzyl)-3-{1-(pyridazine-4-carbonyl)-piperidin-4-yl}-1,3-dihydro-indol-2-one

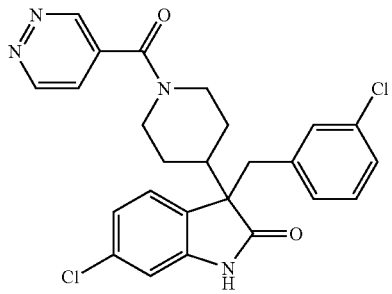

M.W. 481.381 $C_{25}H_{22}Cl_2N_4O_2$

EXAMPLE 74 rac-3-[6-Chloro-3-(3-chloro-benzyl)-2-oxo-2,3-dihydro-1H-indol-3-yl]-piperidine-1-carboxylic acid pyridazin-4-ylamide

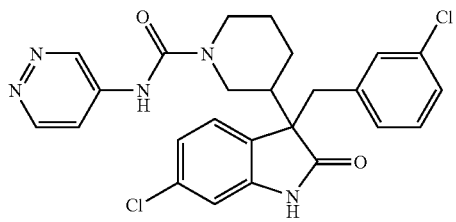

M.W. 496.40 $C_{25}H_{23}Cl_2N_5O_2$

To a suspension of pyridazine-4-carboxylic acid (0.37 g, 3 mmol) (Aldrich) in toluene (15 mL) was added diphenylphosphoryl azide (0.958 g, 3.5 mmol) (Aldrich), followed by the addition of triethylamine (0.35 g, 3.6 mmol) (Aldrich). The mixture was stirred at room temperature for 30 minutes and the mixture became clear. Then the mixture was heated at 80° C. for 2 hours. After cooling to room temperature, the crude (0.8 mL, 0.16 mmol) was added to a solution of rac-6-chloro-3-(3-chloro-benzyl)-3-piperidin-3-yl-1,3-dihydro-indol-2-one (50 mg, 0.13 mmol) (from Example 25a supra) in dichloromethane (3 mL), followed by the addition of triethylamine (46 ul, 0.32 mmol) (Aldrich). The mixture was stirred at room temperature for 30 minutes. The mixture was partitioned between dichlormethane and water. The aqueous layer was extracted with dichlormethane. The combined organic layer was washed with water, brine, dried over MgSO₄ and concentrated. The residue was purified by chromatography to give rac-6-chloro-3-(3-chloro-benzyl)-3-{1-(pyridazine-4-carbonyl)-piperidin-4-yl}-1,3-dihydro-indol-2-one as fraction one and a white solid. (Yield 32 mg, 50%).

HRMS(ES⁺) m/z Calcd for $C_{25}H_{22}Cl_2N_4O_2$+H [(M+H)⁺]: 481.1193. Found: 481.1192. and give rac-3-[6-chloro-3-(3-chloro-benzyl)-2-oxo-2,3-dihydro-1H-indol-3-yl]-piperidine-1-carboxylic acid pyridazin-4-ylamide as fraction two and a white solid. (Yield 30 mg, 45.4%).

HRMS(ES⁺) m/z Calcd for $C_{25}H_{23}Cl_2N_5O_2$+H [(M+H)⁺]: 496.1302. Found: 496.1303.

EXAMPLE 75 rac-3-[6-Chloro-3-(3-chloro-benzyl)-2-oxo-2,3-dihydro-1H-indol-3-yl]-piperidine-1-carboxylic acid (4-cyano-phenyl)-amide

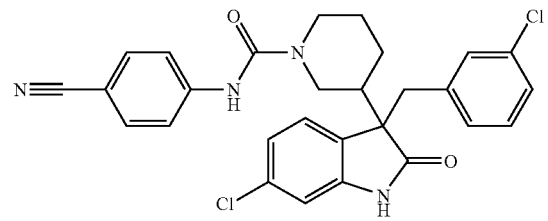

M.W. 519.43 $C_{28}H_{24}Cl_2N_4O_2$

To a solution of rac-6-chloro-3-(3-chloro-benzyl)-3-piperidin-3-yl-1,3-dihydro-indol-2-one (50 mg, 0.13 mmol)

(from Example 25a supra) in dichloromethane (3 mL) was added triethylamine (33.6 mg, 0.33 mmol) (Aldrich), followed by the addition of 1-cyano-4-isocyanato-benzene (23.0 mg, 0.16 mmol) (Aldrich). The mixture was stirred at room temperature for 30 minutes. The mixture was partitioned between dichlormethane and water. The aqueous layer was extracted with dichlormethane. The combined organic layer was washed with water, brine, dried over MgSO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-cyano-phenyl)-amide as a white solid (Yield 40 mg, 58%).

HRMS(ES$^+$) m/z Calcd for C$_{28}$H$_{24}$Cl$_2$N$_4$O$_2$+H [(M+H)$^+$]: 519.1349. Found: 519.1351.

EXAMPLE 76a rac-3-[6-Chloro-3-(3-chloro-benzyl)-2-oxo-2,3-dihydro-1H-indol-3-yl]-piperidine-1-carboxylic acid (4-nitro-phenyl)-amide

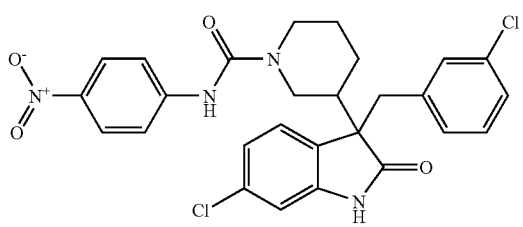

M.W. 539.42 C$_{27}$H$_{24}$Cl$_2$N$_4$O$_4$

To a solution of rac-6-chloro-3-(3-chloro-benzyl)-3-piperidin-3-yl-1,3-dihydro-indol-2-one (0.2 g, 0.54 mmol) (from Example 25a supra) in dichloromethane (3 mL) was added triethylamine (0.135 g, 1.34 mmol) (Aldrich), followed by the addition of 1-nitro-4-isocyanato-benzene (0.105 g, 0.64 mmol) (Aldrich). The mixture was stirred at room temperature for 30 minutes. The mixture was partitioned between ethyl acetate and water. The aqueous layer was extracted with wthyl acetate. The combined organic layer was washed with water, brine, dried over MgSO$_4$ and concentrated to give rac-3-[6-chloro-3-(3-chloro-benzyl)-2-oxo-2,3-dihydro-1H-indol-3-yl]-piperidine-1-carboxylic acid (4-nitro-phenyl)-amide as a yellow solid (Yield 0.19 g, 68%).

EXAMPLE 76b rac-3-[6-Chloro-3-(3-chloro-benzyl)-2-oxo-2,3-dihydro-1H-indol-3-yl]-piperidine-1-carboxylic acid (4-amino-phenyl)-amide

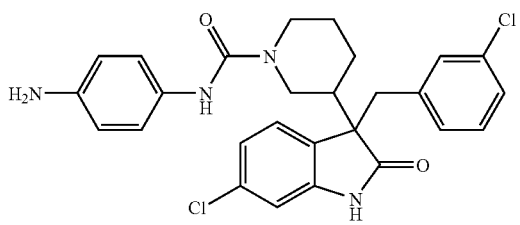

M.W. 509.434 C$_{27}$H$_{26}$Cl$_2$N$_4$O$_2$

To a suspension of rac-3-[6-chloro-3-(3-chloro-benzyl)-2-oxo-2,3-dihydro-1H-indol-3-yl]-piperidine-1-carboxylic acid (4-nitro-phenyl)-amide (0.15 g, 0.28 mmol) (from Example 76a supra) in ethanol (15 mL) was added Rani-nickel, followed by the addition of hydrazine (35 mg, 0.84 mmol) (Aldrich). The mixture was stirred at room temperature for 20 minutes. The crude was filtered through the celite pad. The filtrate was concentrated and the residue was purified by chromatography to give rac-3-[6-chloro-3-(3-chloro-benzyl)-2-oxo-2,3-dihydro-1H-indol-3-yl]-piperidine-1-carboxylic acid (4-amino-phenyl)-amide as a white solid (Yield 90 mg, 64%).

HRMS(ES$^+$) m/z Calcd for C$_{27}$H$_{26}$Cl$_2$N$_4$O$_2$+H [(M+H)$^+$]: 509.1506. Found: 509.1505.

EXAMPLE 77 rac-3-[6-Chloro-3-(3-chloro-benzyl)-2-oxo-2,3-dihydro-1H-indol-3-yl]-piperidine-1-carboxylic acid (4-acetylamino-phenyl)-amide

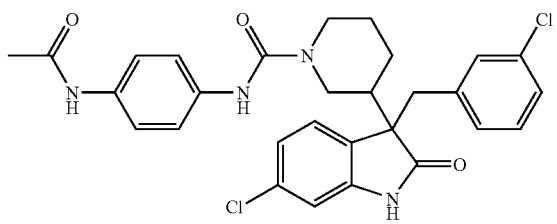

M.W. 551.471 C$_{29}$H$_{28}$Cl$_2$N$_4$O$_3$

To a solution of rac-3-[6-chloro-3-(3-chloro-benzyl)-2-oxo-2,3-dihydro-1H-indol-3-yl]-piperidine-1-carboxylic acid (4-amino-phenyl)-amide (55 mg, 0.11 mmol) (from Example 76b supra) in tetrahydrofuran (2 mL) was added triethylamine (16 mg, 0.16 mmol) (Aldrich), followed by the addition of acetyl chloride (10 mg, 0.13 mmol) (Aldrich). The mixture was stirred at room temperature for 20 minutes. The crude was quenched with water. The aqueous layer was extracted with ethyl acetate. The combined organic layer was washed with water, brine, dried over MgSO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-acetylamino-phenyl)-amide as a white solid (Yield 30 mg, 50%).

RMS(ES$^+$) m/z Calcd for C$_{29}$H$_{28}$Cl$_2$N$_4$O$_3$+H [(M+H)$^+$]: 551.1611. Found: 551.1611.

EXAMPLE 78a

4-Isocyanato-phenol

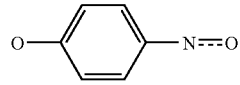

M.W. 135.12 C$_7$H$_5$NO$_2$

To a stirred solution of phosgene (20% in Toluene, 24 mL, 45.9 mmol) (Aldrich) in ethyl acetate (25 mL) at 0° C. was added aminophenol (0.5 g, 4.59 mmol) (Aldrich). The reaction mixture was stirred at 0° C. for 30 minutes and then heated at 80° C. for 3 hours. The mixture was cooling down to room temperature to give crude 4-isocyanato-phenol as 0.18 M solution in toluene and used for the next step without further purification.

EXAMPLE 78b rac-3-[6-Chloro-3-(3-chloro-benzyl)-2-oxo-2,3-dihydro-1H-indol-3-yl]-piperidine-1-carboxylic acid (4-hydroxy-phenyl)-amide

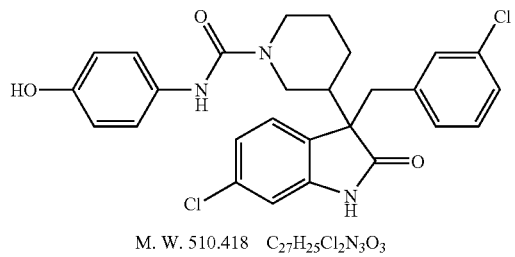

M. W. 510.418  $C_{27}H_{25}Cl_2N_3O_3$

To a solution of rac-6-chloro-3-(3-chloro-benzyl)-3-piperidin-3-yl-1,3-dihydro-indol-2-one (0.1 g, 0.27 mmol) (from Example 25a supra) in dichloromethane (2 mL) was added triethyl amine (67.5 mg, 0.68 mmol) (Aldrich), followed by the addition of solution of 4-isocyanato-phenol (1.8 mL, 0.32 mmol) in toluene (from Example 78a supra). The mixture was stirred at room temperature for 30 minutes. The mixture was partitioned between dichlormethane and water. The aqueous layer was extracted with dichlormethane. The combined organic layer was washed with water, brine, dried over MgSO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-hydroxy-phenyl)-amide as a white solid. (Yield 15 mg, 11%).

HRMS(ES$^+$) m/z Calcd for $C_{27}H_{25}Cl_2N_3O_3$+H [(M+H)$^+$]: 510.1346. Found: 510.1343.

EXAMPLE 79 rac-3-[6-Chloro-3-(3-chloro-benzyl)-2-oxo-2,3-dihydro-1H-indol-3-yl]-piperidine-1-carboxylic acid (4-acetyl-phenyl)-amide

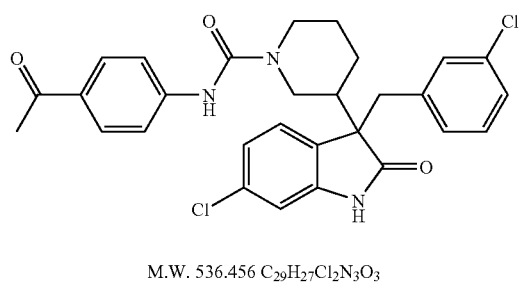

M.W. 536.456  $C_{29}H_{27}Cl_2N_3O_3$

To a solution of rac-6-chloro-3-(3-chloro-benzyl)-3-piperidin-3-yl-1,3-dihydro-indol-2-one (80 mg, 0.21 mmol) (from Example 25a supra) in dichloromethane (2 mL) was added triethylamine (53.8 mg, 0.525 mmol) (Aldrich), followed by the addition of 1-(4-isocyanato-phenyl)-ethanone (41.2 mg, 0.25 mmol) (Aldrich). The mixture was stirred at room temperature for 30 minutes. The mixture was partitioned between dichlormethane and water. The aqueous layer was extracted with dichlormethane. The combined organic layer was washed with water, brine, dried over MgSO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-acetyl-phenyl)-amide as a white solid (Yield 45 mg, 39%).

HRMS(ES$^+$) m/z Calcd for $C_{29}H_{27}Cl_2N_3O_3$+H [(M+H)$^+$]: 536.1502. Found: 536.1500.

EXAMPLE 80 rac-3-[6-Chloro-3-(3-chloro-benzyl)-2-oxo-2,3-dihydro-1H-indol-3-yl]-piperidine-1-carboxylic acid (4-methylsulfanyl-phenyl)-amide

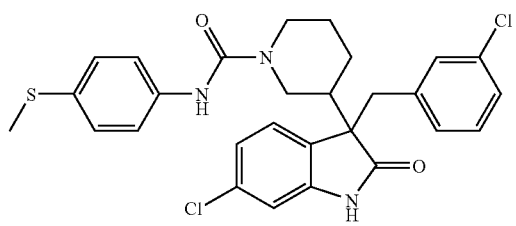

M.W. 540.512  $C_{28}H_{27}Cl_2N_3O_2S$

To a solution of rac-6-chloro-3-(3-chloro-benzyl)-3-piperidin-3-yl-1,3-dihydro-indol-2-one (112 mg, 0.3 mmol) (from Example 25a supra) in dichloromethane (3 mL) was added triethylamine (45.5 mg, 0.45 mmol) (Aldrich), followed by the addition of 1-isocyanato-4-methylsulfanyl-benzene (59.4 mg, 0.36 mmol) (Aldrich). The mixture was stirred at room temperature for 30 minutes. The mixture was partitioned between dichlormethane and water. The aqueous layer was extracted with dichlormethane. The combined organic layer was washed with water, brine, dried over MgSO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-methylsulfanyl-phenyl)-amide as a white solid (Yield 0.13 g, 80%).

HRMS(ES$^+$) m/z Calcd for $C_{28}H_{27}Cl_2N_3O_2S$+H [(M+H)$^+$]: 540.1274. Found: 540.1271.

EXAMPLE 81 rac-3-[6-Chloro-3-(3-chloro-benzyl)-2-oxo-2,3-dihydro-1H-indol-3-yl]-piperidine-1-carboxylic acid (4-methanesulfinyl-phenyl)-amide

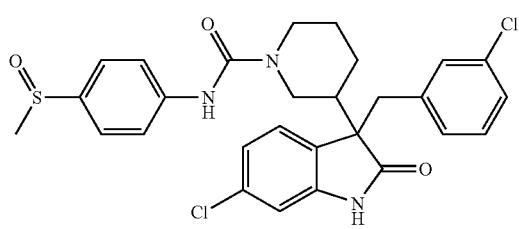

M.W. 556.511  $C_{28}H_{27}Cl_2N_3O_3S$

To the suspension of rac-3-[6-chloro-3-(3-chloro-benzyl)-2-oxo-2,3-dihydro-1H-indol-3-yl]-piperidine-1-carboxylic acid (4-methylsulfanyl-phenyl)-amide (0.28 g, 0.52 mmol) (from Example 80 supra) in dichloromethane (5 mL) was added the suspension of 3-chloro-benzenecarboperoxoic acid (133 mg, 0.78 mmol) (Aldrich) in dichloromethane (2 mL). The mixture was stirred at room temperature for 30 minutes. The mixture was partitioned between dichlormethane and water. The aqueous layer was extracted with dichlormethane. The combined organic layer was washed with 10% of sodium sulfite solution, saturated sodium bicarbonate, brine, dried over MgSO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-methanesulfinyl-phenyl)-amide as a grey solid (Yield 0.16 g, 57%).

HRMS(ES$^+$) m/z Calcd for $C_{28}H_{27}Cl_2N_3O_3S+H$ [(M+H)$^+$]: 556.1223. Found: 556.1224.

EXAMPLE 82 rac-3-[6-Chloro-3-(3-chloro-benzyl)-2-oxo-2,3-dihydro-1H-indol-3-yl]-piperidine-1-carboxylic acid (4-methanesulfonyl-phenyl)-amide

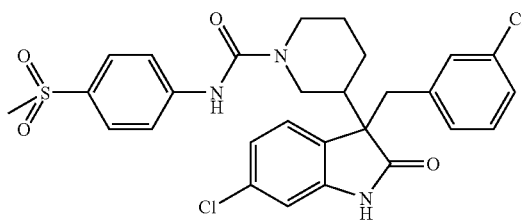

M.W. 572.51 $C_{28}H_{27}Cl_2N_3O_4S$

To a solution of rac-3-[6-chloro-3-(3-chloro-benzyl)-2-oxo-2,3-dihydro-1H-indol-3-yl]-piperidine-1-carboxylic acid (4-methanesulfinyl-phenyl)-amide (85 mg, 0.15 mmol) (from Example 81 supra) in dichloromethane (4 mL) was added 3-chloro-benzenecarboperoxoic acid (52.6 mg, 0.3 mmol) (Aldrich). The mixture was stirred at room temperature for 1 hour. The mixture was partitioned between dichlormethane and water. The aqueous layer was extracted with dichlormethane. The combined organic layer was washed with 2% of sodium sulfite solution, saturated sodium bicarbonate, brine, dried over MgSO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid (4-methanesulfonyl-phenyl)-amide as a pale yellow solid. (Yield 81 mg, 93%).

HRMS(ES$^+$) m/z Calcd for $C_{28}H_{27}Cl_2N_3O_4S+H$ [(M+H)$^+$]: 572.1172. Found: 572.1172.

EXAMPLE 83a

Pyridine-2,5-dicarboxylic acid-2-methyl ester

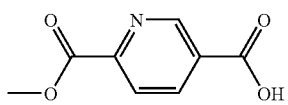

M.W. 181.15 $C_8H_7NO_4$

To a suspension of pyridine-2,5-dicarboxylic acid (4.2 g, 25.1 mmol) (Aldrich) in methanol (50 mL) was added concentrated sulfuric acid (1.5 g, 15.3 mmol) (Aldrich). The mixture was heated at refluxing for 2 hours. The crude was cooled down to room temperature and poured into water (250 mL). The precipitate formed was collected and washed with methanol to give pyridine-2,5-dicarboxylic acid-2-methyl ester as a grey solid. (Yield 1.5 g, 33%).

EXAMPLE 83b

5-Azidocarbonyl-pyridine-2-carboxylic acid methyl ester

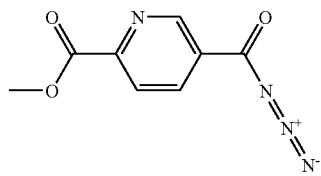

M.W. 206.16 $C_8H_6N_4O_3$

To a solution of pyridine-2,5-dicarboxylic acid-2-methyl ester (0.5 g, 2.76 mmol)) (from Example 83a supra) at −10° C. in acetone (9.16 mL) was added triethylamine (0.385 mL, 2.76 mmol) (Aldrich), followed by the addition of ethyl chloroformate (0.265 mL, 2.76 mmol). (Aldrich). After the mixture was stirred at −10° C. for 30 minutes, an aqueous solution of sodium azide (0.53 g, 8.28 mmol) in water (10 mL) was added. The mixture was warmed up and stirred at room temperature for 1 hour, then concentrated to half volume, extracted with dichlormethane. The combined organic layer was washed with water, brine, dried over MgSO$_4$ and concentrated to give 5-azidocarbonyl-pyridine-2-carboxylic acid methyl ester as a white solid (Yield 0.47 g, 83%).

EXAMPLE 83c

5-Isocyanato-pyridine-2-carboxylic acid methyl ester

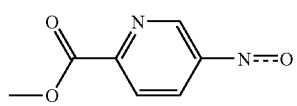

M.W. 178.15 $C_8H_6N_2O_3$

A solution of 5-azidocarbonyl-pyridine-2-carboxylic acid methyl ester (100 mg, 0.32 mmol) (from Example 83b supra) in toluene (2 mL) was heated at 100° C. for 2.5 hours. The mixture was cooling down to room temperature to give crude 5-isocyanato-pyridine-2-carboxylic acid methyl ester and used for the next step without further purification.

EXAMPLE 83d rac-5-({3-[6-Chloro-3-(3-chloro-benzyl)-2-oxo-2,3-dihydro-1H-indol-3-yl]-piperidine-1-carbonyl}-amino)-pyridine-2-carboxylic acid methyl ester

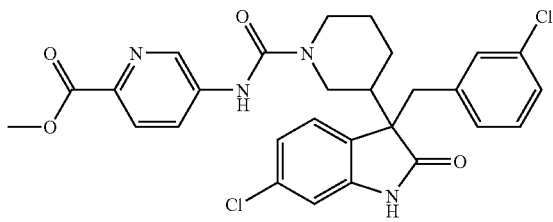

M.W. 553.433 $C_{28}H_{26}Cl_2N_4O_4$

To a solution of rac-6-chloro-3-(3-chloro-benzyl)-3-piperidin-3-yl-1,3-dihydro-indol-2-one (100 mg, 0.27 mmol) (from Example 25a supra) in dichloromethane (3 mL) was added triethylamine (67.8 mg, 0.67 mmol) (Aldrich), followed by the addition of solution of 5-isocyanato-pyridine-2-carboxylic acid methyl ester in toluene (from Example 83c supra). The mixture was stirred at room temperature for 30 minutes. The mixture was partitioned between dichlormethane and water. The aqueous layer was extracted with dichlormethane. The combined organic layer was washed with water, brine, dried over MgSO$_4$ and concentrated. The residue was purified by chromatography to give rac-5-({3-[6-chloro-3-(3-chloro-benzyl)-2-oxo-2,3-dihydro-1H-indol-3-yl]-piperidine-1-carbonyl}-amino)-pyridine-2-carboxylic acid methyl ester as a white solid. (Yield 83 mg, 56.1%).

HRMS(ES$^+$) m/z Calcd for $C_{28}H_{26}Cl_2N_4O_4$+H [(M+H)$^+$]: 553.1404. Found: 553.1399.

EXAMPLE 84 rac-5-({3-[6-Chloro-3-(3-chloro-benzyl)-2-oxo-2,3-dihydro-1H-indol-3-yl]-piperidine-1-carbonyl}amino)-pyridine-2-carboxylic acid

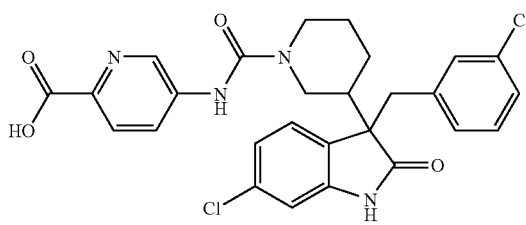

M.W. 539.417 $C_{27}H_{24}Cl_2N_4O_4$

To a solution of rac-5-({3-[6-chloro-3-(3-chloro-benzyl)-2-oxo-2,3-dihydro-1H-indol-3-yl]-piperidine-1-carbonyl}-amino)-pyridine-2-carboxylic acid methyl ester (67 mg, 0.12 mmol) (from Example 83 d supra) in tetrahydrofuran (2 mL) was added the suspension of lithium hydroxide monohydrate (51 mg, 1.2 mmol) (Aldrich) in water (2 mL). The mixture was stirred at room temperature for overnight. The solvent was removed and the residue was partitioned between ethyl acetate and water. The aqueous layer was acidified to "pH"<5 with dilute HCl, then extracted with ethyl acetate several times. The combined organic layer was washed with water, brine, dried over MgSO$_4$ and concentrated to give rac-5-({3-[6-chloro-3-(3-chloro-benzyl)-2-oxo-2,3-dihydro-1H-indol-3-yl]-piperidine-1-carbonyl}-amino)-pyridine-2-carboxylic acid as a white solid. (Yield 45 mg, 69.2%).

HRMS(ES$^+$) m/z Calcd for $C_{27}H_{24}Cl_2N_4O_4$+H[(M+H)$^+$]: 539.1248. Found: 539.1242.

EXAMPLE 85 rac-3-[6-Chloro-3-(3-chloro-benzyl)-2-oxo-2,3-dihydro-1H-indol-3-yl]-piperidine-1-carboxylic acid [4-(2,5-dioxo-2,5-dihydro-pyrrol-1-yl)-phenyl]-amide

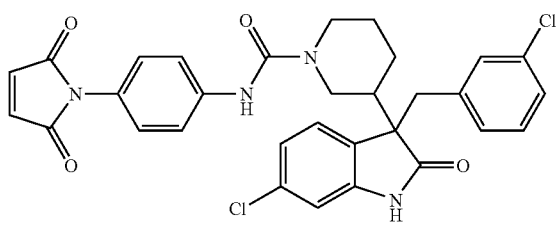

M. W. 589.476 $C_{31}H_{26}Cl_2N_4O_4$

To a solution of rac-6-chloro-3-(3-chloro-benzyl)-3-piperidin-3-yl-1,3-dihydro-indol-2-one (80 mg, 0.21 mmol) (from Example 25a supra) in dichloromethane (3 mL) was added triethylamine (32.4 mg, 0.32 mmol) (Aldrich), followed by the addition of 1-(4-isocyanato-phenyl)-pyrrole-2, 5-dione (50 mg, 0.23 mmol) (Fluka). The mixture was stirred at room temperature for 0.5 hour. The mixture was partitioned between dichlormethane and water. The aqueous layer was extracted with dichlormethane. The combined organic layer was washed with water, brine, dried over MgSO$_4$ and concentrated. The residue was purified by chromatography to give rac-3-[6-chloro-3-(3-chloro-benzyl)-2-oxo-2,3-dihydro-1H-indol-3-yl]-piperidine-1-carboxylic acid [4-(2,5-dioxo-2,5-dihydro-pyrrol-1-yl)-phenyl]-amide as a white solid (Yield 35 mg, 28%).

HRMS(ES$^+$) m/z Calcd for $C_{31}H_{26}Cl_2N_4O_4$+H [(M+H)$^+$]: 589.1404. Found: 589.1401.

EXAMPLE 86 rac-5-{3-[6-Chloro-3-(3-chloro-benzyl)-2-oxo-2,3-dihydro-1H-indol-3-yl]-piperidine-1-carbonyl}-pyridine-2-carboxylic acid methyl ester

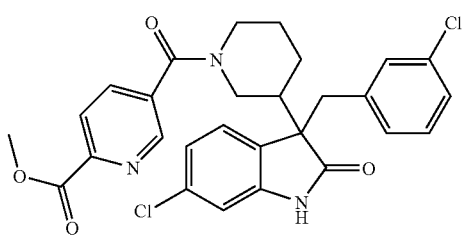

M.W. 538.428 $C_{28}H_{25}Cl_2N_3O_4$

To a suspension of pyridine-2,5-dicarboxylic acid-2-methyl ester (0.54 g, 3.0 mmol) (from Example 83 a supra) in toluene (15 mL) was added diphenylphosphoryl azide (0.958 g, 3.5 mmol) (Aldrich), followed by the addition of triethylamine (0.35 g, 3.6 mmol) (Aldrich). The mixture was stirred at room temperature for 0.5 hour and the mixture became clear. Then the mixture was heated at 80° C. for 2 hours. After cooling to room temperature, the crude (0.21 mL, 0.38 mmol) was added to a solution of rac-6-chloro-3-(3-chloro-benzyl)-3-piperidin-3-yl-1,3-dihydro-indol-2-one (120 mg, 0.32 mmol) (from Example 25a supra) in dichloromethane (3 mL), followed by the addition of triethylamine (0.11 mL, 0.80 mmol) The mixture was stirred at room temperature for 0.5 hour. The mixture was partitioned between dichlormethane and water. The aqueous layer was extracted with dichloromethane. The combined organic layer was washed with water, brine, dried over MgSO$_4$ and concentrated. The residue was purified by chromatography to give rac-5-{3-[6-chloro-3-(3-chloro-benzyl)-2-oxo-2,3-dihydro-1H-indol-3-yl]-piperidine-1-carbonyl}-pyridine-2-carboxylic acid methyl ester as a white solid. (Yield 65 mg, 36.5%).

HRMS(ES$^+$) m/z Calcd for $C_{28}H_{25}Cl_2N_3O_4$+H [(M+H)$^+$]: 538.1295. Found: 538.1292.

EXAMPLE 87 rac-6-chloro-3-(3-chloro-benzyl)-3-(3-oxo-cycloheptyl)-1,3-dihydro-indol-2-one

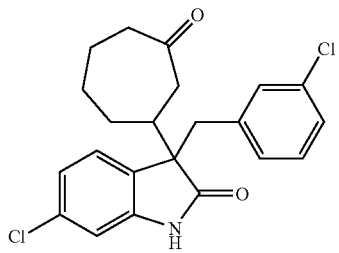

M.W. 402.32 $C_{22}H_{21}Cl_2NO_2$

A mixture of rac-6-chloro-3-(3-chloro-benzyl)-1,3-dihydro-indol-2-one (0.23 g, 0.90 mmol) (from Example 30b supra), 2-cyclohept-2-enone (0.25 g, 1.80 mmol) (Aldrich), 1,8-diazabicyclo[5.4.0]undec-7-ene (0.68 g, 4.48 mmol) (Fluka AG) in methanol (20 mL) was heated at 100° C. for 0.5 hour. After cooling, the mixture was concentrated, diluted with water, extracted with ethyl acetate. The organic layers were separated, dried over Na$_2$SO$_4$ and concentrated. The residue was purified by chromatography (EtOAc:hexanes=1:2, V/V) to give rac-6-chloro-3-(3-chloro-benzyl)-3-(3-oxo-cycloheptyl)-1,3-dihydro-indol-2-one (Yield 0.31 g, 97%).

HRMS(ES$^+$) m/z Calcd for $C_{22}H_{21}Cl_2NO_2$+Na [(M+Na)$^+$]: 424.0841. Found: 424.0844.

EXAMPLE 88

In Vitro Assay

In a cell based assay, the ability of the compounds to inhibit the interaction between p53 and MDM2 proteins was measured.

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

| Example | IC$_{50}$ (μM) |
|---|---|
| 3C | 5.38 |
| 6C | 9.49 |
| 9 | 0.46 |
| 13 | 0.28 |

What is claimed is:
1. A compound of the formula I

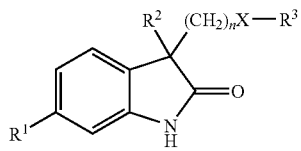

or the pharmaceutically acceptable salts thereof
wherein
X is a bond, O or N;
R$^1$ is halogen;
R$^2$ is selected from the group consisting of substituted aryl, substituted heteroaryl, substituted cycloalkyl and substituted heterocycle,
R$^3$ is substituted aryl or substituted heteroaryl and
n is 1-3.

2. The compound of claim 1 wherein R$^1$ is halogen, R$^2$ is substituted aryl, substituted heteroaryl, substituted cycloalkyl or substituted heterocycle, R$^3$ is substituted aryl or substituted heteroaryl, n is 1 and X is a bond.

3. The compound of claim 1 wherein R$^1$ is halogen, R$^2$ is substituted aryl, substituted heteroaryl, substituted cycloalkyl or substituted heterocycle, R$^3$ is a meta halogen substituted phenyl, n is 1 and X is a bond.

4. The compound of claim 1 selected from the group consisting of:
rac-6-Chloro-3-(3-chloro-benzyl)-3-(1-methyl-1H-pyrazol-4-yl)-1,3-dihydro-indol-2-one;
rac-3-(1-Acetyl-piperidin-4-yl)-6-chloro-3-(3-chloro-benzyl)-1,3-dihydro-indol-2-one;

rac-4-[6-Chloro-3-(3-chloro-benzyl)-2-oxo-2,3-dihydro-1H-indol-3-yl]-piperidine-1-carboxylic acid methylamide;
rac-3-(3-Bromo-benzyl)-6-chloro-3-(3-methoxy-phenyl)-1,3-dihydro-indol-2-one;
rac-6-Chloro-3-(3-fluoro-benzyl)-3-(3-methoxy-phenyl)-1,3-dihydro-indol-2-one;
rac-6-Chloro-3-(3-chloro-benzyl)-3-cyclohexyl-1,3-dihydro-indol-2-one;
rac-5-[6-Chloro-3-(3-chloro-benzyl)-2-oxo-2,3-dihydro-1H-indol-3-yl]-3,4-dihydro-2H-pyridine-1-carboxylic acid tert-butyl ester and
rac-6-Chloro-3-(2,6-dichloro-pyridin-4-ylmethyl)-3-(3-methoxy-phenyl)-1,3-dihydro-indol-2-one.

5. The compound of claim 1 selected from the group consisting of:
3-[6-Chloro-3-(3-chloro-benzyl)-2-oxo-2,3-dihydro-1H-indol-3-yl]-piperidine-1-carboxylic acid tert-butyl ester;
rac-5-[6-Chloro-3-(2,6-dichloro-pyridin-4-ylmethyl)-2-oxo-2,3-dihydro-1H-indol-3-yl]-3,4-dihydro-2H-pyridine-1-carboxylic acid tert-butyl ester;
3-(1-Acetyl-piperidin-3-yl)-6-chloro-3-(3-chloro-benzyl)-1,3-dihydro-indol-2-one;
6-Chloro-3-(3-chloro-benzyl)-3-[1-(pyrrolidine-1-carbonyl)-piperidin-3-yl]-1,3-dihydro-indol-2-one;
3-[6-Chloro-3-(3-chloro-benzyl)-2-oxo-2,3-dihydro-1H-indol-3-yl]-piperidine-1-carboxylic acid methylamide;
6-Chloro-3-(3-chloro-benzyl)-3-[1-(morpholine-4-carbonyl)-piperidin-3-yl]-1,3-dihydro-indol-2-one;
rac-6-Chloro-3-(3-chloro-benzyl)-3-(2,6-dimethoxy-pyrimidin-4-yl)-1,3-dihydro-indol-2-one, rac-6-Chloro-3-(3-chloro-benzyl)-3-(3-oxo-cyclohexyl)-1,3-dihydro-indol-2-one,
3-[6-Chloro-3-(3-chloro-benzyl)-2-oxo-2,3-dihydro-1H-indol-3-yl]-piperidine-1-carboxylic acid ethylamide,
3-[6-Chloro-3-(3-chloro-benzyl)-2-oxo-2,3-dihydro-1H-indol-3-yl]-piperidine-1-carboxylic acid propylamide,
3-[6-Chloro-3-(3-chloro-benzyl)-2-oxo-2,3-dihydro-1H-indol-3-yl]-piperidine-1-carboxylic acid tert-butylamide,
3-[6-Chloro-3-(3-chloro-benzyl)-2-oxo-2,3-dihydro-1H-indol-3-yl]-piperidine-1-carboxylic acid (2-chloro-ethyl)-amide,
3-[6-Chloro-3-(3-chloro-benzyl)-2-oxo-2,3-dihydro-1H-indol-3-yl]-piperidine-1-carboxylic acid phenylamide,
3-[6-Chloro-3-(3-chloro-benzyl)-2-oxo-2,3-dihydro-1H-indol-3-yl]-piperidine-1-carboxylic acid isopropylamide,
rac-6-Chloro-3-(3-chloro-4-fluoro-benzyl)-3-(3-methoxy-phenyl)-1,3-dihydro-indol-2-one, and
3-[6-Chloro-3-(3-chloro-benzyl)-2-oxo-2,3-dihydro-1H-indol-3-yl]-piperidine-1-carboxylic acid cyclohexylamide.

6. The compound of claim 1 selected from the group consisting of
rac-6-Chloro-3-(3-chloro-benzyl)-3-pyridin-3-yl-1,3-dihydro-indol-2-one,
rac-6-Chloro-3-(3-chloro-benzyl)-3-(3,5-dimethoxy-phenyl)-1,3-dihydro-indol-2-one,
rac-3-[6-Chloro-3-(3-chloro-benzyl)-2-oxo-2,3-dihydro-1H-indol-3-yl]-piperidine-1-carboxylic acid (3-methoxy-phenyl)-amide,
rac-3-[6-Chloro-3-(3-chloro-benzyl)-2-oxo-2,3-dihydro-1H-indol-3-yl]-piperidine-1-carboxylic acid (4-methoxy-phenyl)-amide,
rac-3-[6-Chloro-3-(3-chloro-benzyl)-2-oxo-2,3-dihydro-1H-indol-3-yl]-piperidine-1-carboxylic acid (2-methoxy-phenyl)-amide,
rac-3-[6-Chloro-3-(3-chloro-benzyl)-2-oxo-2,3-dihydro-1H-indol-3-yl]-piperidine-1-carboxylic acid (4-chloro-phenyl)-amide,
rac-3-[6-Chloro-3-(3-chloro-benzyl)-2-oxo-2,3-dihydro-1H-indol-3-yl]-piperidine-1-carboxylic acid (3-chloro-phenyl)-amide,
rac-3-[6-Chloro-3-(3-chloro-benzyl)-2-oxo-2,3-dihydro-1H-indol-3-yl]-piperidine-1-carboxylic acid pyridine-3-yl-amide,
rac-6-Chloro-3-(3-chloro-benzyl)-3-naphthalen-2-yl-1,3-dihydro-indol-2-one and
rac-6-Chloro-3-(3-chloro-benzyl)-3-{1-[4-(2-Morpholin-4-yl-2-oxo-ethyl)-piperazine-1-carbonyl]-piperidine-3-yl}-1,3-dihydro-indol-2-one.

7. The compound of claim 1 selected from the group consisting of
rac-3-(1-Butyl-piperidin-4-yl)-6-Chloro-3-(3-chloro-benzyl)-1,3-dihydro-indol-2-one,
rac-6-Chloro-3-(3-chloro-benzyl)-3-{1-[4-(2-Morpholin-4-yl-2-oxo-ethyl)-piperazine-1-carbonyl]-piperidine-4-yl}-1,3-dihydro-indol-2-one,
rac-3-[6-Chloro-3-(3-chloro-benzyl)-2-oxo-2,3-dihydro-1H-indol-3-yl]-piperidine-1-carboxylic acid (3,4,5-trimethoxy-phenyl)-amide,
rac-6-Chloro-3-(3-chloro-benzyl)-3-(3,4-dimethyl-phenyl)-1,3-dihydro-indol-2-one,
rac-6-Chloro-3-(3-chloro-benzyl)-3-(4-isopropyl-phenyl)-1,3-dihydro-indol-2-one,
rac-3-[6-Chloro-3-(3-chloro-benzyl)-2-oxo-2,3-dihydro-1H-indol-3-yl]-piperidine-1-carboxylic acid (4-diomethylamino-phenyl)-amide,
rac-4-({3-[6-Chloro-3-(3-chloro-benzyl)-2-oxo-2,3-dihydro-1H-indol-3-yl]-piperidine-1-carbonyl}-amino)-benzoic acid ethyl ester,
rac-3-[6-Chloro-3-(3-chloro-benzyl)-2-oxo-2,3-dihydro-1H-indol-3-yl]-piperidine-1-carboxylic acid (4-butoxy-phenyl)-amide and
rac-3-[6-Chloro-3-(3-chloro-benzyl)-2-oxo-2,3-dihydro-1H-indol-3-yl]-piperidine-1-carboxylic acid (4-trifluoromethoxy-phenyl)-amide.

8. The compound of claim 1 selected from the group consisting of
rac-3-[6-Chloro-3-(3-chloro-benzyl)-2-oxo-2,3-dihydro-1H-indol-3-yl]-piperidine-1-carboxylic acid pyridine-4-ylamide,
rac-3-[6-Chloro-3-(3-chloro-benzyl)-2-oxo-2,3-dihydro-1H-indol-3-yl]-piperidine-1-carboxylic acid (2,6-dichloro-pyridin-4-yl)-amide,
rac-6-chloro-3-(3-chloro-benzyl)-3-(4-dimethylamino-phenyl)-1,3-dihydro-indol-2-one,
rac-4-[6-Chloro-3-(3-chloro-benzyl)-2-oxo-2,3-dihydro-1H-indol-3-yl]-azepane-1-carboxylic acid tert-butyl ester,
rac-3-[6-Chloro-3-(3-chloro-benzyl)-2-oxo-2,3-dihydro-1H-indol-3-yl]-piperidine-1-carboxylic acid (6-methoxy-pyridin-3-yl)-amide,
rac-4-({3-[6-Chloro-3-(3-chloro-benzyl)-2-oxo-2,3-dihydro-1H-indol-3-yl]-piperidine-1-carbonyl}-amino)-benzoic acid methyl ester,
rac-4-({3-[6-Chloro-3-(3-chloro-benzyl)-2-oxo-2,3-dihydro-1H-indol-3-yl]-piperidine-1-carbonyl}-amino)-benzoic acid,
rac-3-Azepan-1-yl-6-chloro-3-(3-chloro-benzyl)-1,3-dihydro-indol-2-one, rac-3-(1-Benzyl-piperidin-3-yl)-6-chloro-3-(3-chloro-benzyl)-1,3-dihydro-indol-2-one and rac-3-[6-Chloro-3-(3-chloro-benzyl)-2-oxo-2,3-dihydro-1H-indol-3-yl]-piperidine-1-carboxylic acid (6-chloro-pyridin-3-yl)-amide.

9. The compound of claim 1 selected from the group consisting of rac-3-[6-Chloro-3-(3-chloro-benzyl)-2-oxo-2,3-dihydro-1H-indol-3-yl]-piperidine-1-carboxylic acid (4-carbamoyl-phenyl)-amide, 3-[6-Chloro-3-(3-chloro-benzyl)-2-oxo-2,3-dihydro-1H-indol-3-yl]-piperidine-1-carboxylic acid phenylamide, rac-3-({3-[6-Chloro-3-(3-chloro-benzyl)-2-oxo-2,3-dihydro-1H-indol-3-yl]-piperidine-1-carbonyl}-amino)-benzoic acid methyl ester, rac-3-({3-[6-Chloro-3-(3-chloro-benzyl)-2-oxo-2,3-dihydro-1H-indol-3-yl]-piperidine-1-carbonyl}-amino)-benzoic acid, rac-3-[6-Chloro-3-(3-chloro-benzyl)-2-oxo-2,3-dihydro-1H-indol-3-yl]-piperidine-1-carboxylic acid (4-fluoro-phenyl)-amide, rac-3-[6-Chloro-3-(3-chloro-benzyl)-2-oxo-2,3-dihydro-1H-indol-3-yl]-piperidine-1-carboxylic acid (6-methyl-pyridine-3-yl)-amide, rac-6-Chloro-3-(3-chloro-benzyl)-3-{1-(pyridine-4-carbonyl)-piperidin-4-yl}-1,3-dihydro-indol-2-one, rac-6-Chloro-3-(3-chloro-benzyl)-3-{1-(pyridazine-4-carbonyl)-piperidin-4-yl}-1,3-dihydro-indol-2-one, rac-3-[6-Chloro-3-(3-chloro-benzyl)-2-oxo-2,3-dihydro-1H-indol-3-yl]-piperidine-1-carboxylic acid pyridazin-4-ylamide and 3-[6-Chloro-3-(3-chloro-benzyl)-2-oxo-2,3-dihydro-1H-indol-3-yl]-piperidine-1-carboxylic acid tert-butyl ester.

10. The compound of claim 1 selected from the group consisting of rac-3-[6-Chloro-3-(3-chloro-benzyl)-2-oxo-2,3-dihydro-1H-indol-3-yl]-piperidine-1-carboxylic acid (4-cyano-phenyl)-amide, rac-3-[6-Chloro-3-(3-chloro-benzyl)-2-oxo-2,3-dihydro-1H-indol-3-yl]-piperidine-1-carboxylic acid (4-nitro-phenyl)-amide, rac-3-[6-Chloro-3-(3-chloro-benzyl)-2-oxo-2,3-dihydro-1H-indol-3-yl]-piperidine-1-carboxylic acid (4-amino-phenyl)-amide, rac-3-[6-Chloro-3-(3-chloro-benzyl)-2-oxo-2,3-dihydro-1H-indol-3-yl]-piperidine-1-carboxylic acid (4-acetylamino-phenyl)-amide, rac-3-[6-Chloro-3-(3-chloro-benzyl)-2-oxo-2,3-dihydro-1H-indol-3-yl]-piperidine-1-carboxylic acid (4-hydroxy-phenyl)-amide, rac-3-[6-Chloro-3-(3-chloro-benzyl)-2-oxo-2,3-dihydro-1H-indol-3-yl]-piperidine-1-carboxylic acid (4-acetyl-phenyl)-amide, rac-3-[6-Chloro-3-(3-chloro-benzyl)-2-oxo-2,3-dihydro-1H-indol-3-yl]-piperidine-1-carboxylic acid (4-methylsulfanyl-phenyl)-amide, rac-3-[6-Chloro-3-(3-chloro-benzyl)-2-oxo-2,3-dihydro-1H-indol-3-yl]-piperidine-1-carboxylic acid (4-methanesulfinyl-phenyl)-amide, rac-3-[6-Chloro-3-(3-chloro-benzyl)-2-oxo-2,3-dihydro-1H-indol-3-yl]-piperidine-1-carboxylic acid (4-methanesulfonyl-phenyl)-amide and rac-5-({3-[6-Chloro-3-(3-chloro-benzyl)-2-oxo-2,3-dihydro-1H-indol-3-yl]-piperidine-1-carbonyl}-amino)-pyridine-2-carboxylic acid methyl ester.

11. The compound of claim 1 selected from the group consisting of rac-5-({3-[6-Chloro-3-(3-chloro-benzyl)-2-oxo-2,3-dihydro-1H-indol-3-yl]-piperidine-1-carbonyl}-amino)-pyridine-2-carboxylic acid, rac-3-[6-Chloro-3-(3-chloro-benzyl)-2-oxo-2,3-dihydro-1H-indol-3-yl]-piperidine-1-carboxylic acid [4-(2,5-dioxo-2,5-dihydro-pyrrol-1-yl)-phenyl]-amide, 4-({3-[6-Chloro-3-(3-chloro-benzyl)-2-oxo-2,3-dihydro-1H-indol-3-yl]-piperidine-1-carbonyl}-amino)-benzoic acid, rac-5-{3-[6-Chloro-3-(3-chloro-benzyl)-2-oxo-2,3-dihydro-1H-indol-3-yl]-piperidine-1-carbonyl}-pyridine-2-carboxylic acid methyl ester, 3-[6-Chloro-3-(3-chloro-benzyl)-2-oxo-2,3-dihydro-1H-indol-3-yl]-piperidine-1-carboxylic acid (4-acetyl-phenyl)-amide, 3-[6-Chloro-3-(3-chloro-benzyl)-2-oxo-2,3-dihydro-1H-indol-3-yl]-piperidine-1-carboxylic acid (4-methanesulfonyl-phenyl)-amide, rac-6-chloro-3-(3-chloro-benzyl)-3-(3-oxo-cycloheptyl)-1,3-dihydro-indol-2-one, rac-6-chloro-3-(3-chloro-benzyl)-3-cyclopentylmethyl-1,3-dihydro-indol-2-one, rac-6-chloro-3-(3-chloro-benzyl)-3-(3,3-dimethyl-butyl)-1,3-dihydro-indol-2-one and rac-3-benzyl-6-chloro-3-(3-chloro-benzyl)-1,3-dihydro-indol-2-one.

12. A pharmaceutical preparation comprising a compound of the formula I

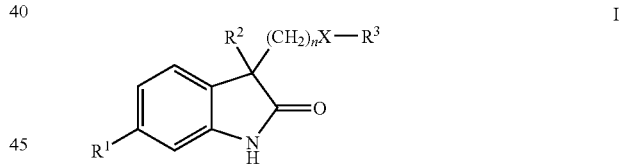

or the pharmaceutically acceptable salts thereof
wherein
X is a bond, O or N;
$R^1$ is halogen;
$R^2$ is selected from the group consisting of substituted aryl, substituted heteroaryl, substituted cycloalkyl and, substituted heterocycle
$R^3$ is substituted aryl or substituted heteroaryl and
n is 1-3
together with a pharmaceutically acceptable excipient.

* * * * *